US007402418B2

(12) United States Patent
Osumi et al.

(10) Patent No.: US 7,402,418 B2
(45) Date of Patent: Jul. 22, 2008

(54) GENES PARTICIPATING IN THE SYNTHESIS OF FATTY ACID HAVING TRANS-11-,CIS-13-CONJUGATED DOUBLE BOND AND UTILIZATION THEREOF

(75) Inventors: Mari Osumi, Machida (JP); Junko Murase, Yokohama (JP); Jun Imamura, Machida (JP)

(73) Assignees: Plantech Research Institute, Tokyo (JP); Incorporated Administrative Agency, National Agriculture & Bio-oriented Research Organization, Ibaraki (JP)

( * ) Notice: Subject to any disclaimer, the term of this patent is extended or adjusted under 35 U.S.C. 154(b) by 0 days.

(21) Appl. No.: 10/490,299

(22) PCT Filed: Sep. 20, 2002

(86) PCT No.: PCT/JP02/09683

§ 371 (c)(1),
(2), (4) Date: Oct. 13, 2004

(87) PCT Pub. No.: WO03/027296

PCT Pub. Date: Apr. 3, 2003

(65) Prior Publication Data

US 2005/0108788 A1 May 19, 2005

(30) Foreign Application Priority Data

| Sep. 20, 2001 | (JP) | ............................. 2001-286390 |
| Apr. 30, 2002 | (JP) | ............................. 2002-127810 |
| Aug. 2, 2002 | (JP) | ............................. 2002-226386 |
| Aug. 2, 2002 | (JP) | ............................. 2002-226387 |

(51) Int. Cl.
*A01H 1/00* (2006.01)
*C12N 15/82* (2006.01)
*C12N 9/04* (2006.01)
*C12N 5/04* (2006.01)
*C07H 21/04* (2006.01)
*C12P 7/64* (2006.01)
*A23D 7/005* (2006.01)

(52) U.S. Cl. ...................... 435/190; 435/134; 435/419; 435/468; 800/281; 536/23.2

(58) Field of Classification Search ........................ None
See application file for complete search history.

(56) References Cited

U.S. PATENT DOCUMENTS

| 2,293,674 | A |   | 8/1942 | Lindsay |
| 2,421,157 | A |   | 5/1947 | Myers et al. |
| 4,686,191 | A |   | 8/1987 | Itoh et al. |
| 4,939,094 | A |   | 7/1990 | Kuga et al. |
| 5,160,735 | A |   | 11/1992 | Yasumura et al. |
| 5,850,026 | A | * | 12/1998 | DeBonte et al. ............. 800/281 |
| 6,593,514 | B1 |   | 7/2003 | Cahoon et al. |

FOREIGN PATENT DOCUMENTS

| CA | 2454372 | 2/2003 |
| EP | 1175901 | 1/2002 |
| JP | 2000-355538 | 12/2000 |
| JP | 2002/238566 | 8/2002 |
| WO | 00/11176 | 3/2000 |
| WO | 00/62772 | 10/2000 |

(Continued)

OTHER PUBLICATIONS

Edgar B. Cahoon, et al. Formation of Conjugated Δ 8, Δ 10-Double Bonds by Δ 12-Oleic-acid Desaturase-related Enzymes. Jan. 26, 2001. J. Biol. Chem., vol. 276, Issue 4, 2637-2643.*

(Continued)

*Primary Examiner*—Robert B. Mondesi
*Assistant Examiner*—Kagnew Gebreyesus
(74) *Attorney, Agent, or Firm*—Greenblum & Bernstein, P.L.C.

(57) ABSTRACT

An object of the present invention is to clone a gene which is involved in synthesis of fatty acid having trans-11-, cis-13-conjugated double bonds from fatty acid having a double bone at position Δ12. The present invention provides a gene having any one of the following nucleotide sequences:

(A) a nucleotide sequence encoding an amino acid sequence shown in SEQ ID NO: 1 or 12;

(B) a nucleotide sequence encoding an amino acid sequence comprising a deletion, addition or substitution of one or several amino acids with respect to the amino acid sequence shown in SEQ NO: 1 or 12, and having an ability of synthesizing fatty acid having trans-11-, cis-13-conjugated double bonds from fatty acid having a double bond at position Δ12;

(C) a nucleotide sequence shown in SEQ ID NO: 2 or 13;

(D) a nucleotide sequence comprising a deletion, addition or substitution of one or several nucleotides with respect to the nucleotide sequence shown in SEQ ID NO: 2 or 13, and encoding a protein having an ability of synthesizing fatty acid having trans-11-, cis-13-conjugated double bonds from fatty acid having a double bond at position Δ12; and (E) a nucleotide sequence hybridizing with the nucleotide sequence shown in SEQ ID NO: 2 or 13 or a complementary sequence thereof under stringent conditions, and encoding a protein having an ability of synthesizing fatty acid having trans-11-, cis-13-conjugated double bonds from fatty acid having a double bond at position Δ12.

20 Claims, 12 Drawing Sheets

FOREIGN PATENT DOCUMENTS

| | | |
|---|---|---|
| WO | 01/12800 | 2/2001 |
| WO | 01/16362 | 3/2001 |
| WO | 03/012094 | 2/2003 |

OTHER PUBLICATIONS

Schubert et al (1999). Antioxidant and eicosanoid enzyme inhibition properties of pomegranate seed oil J Ethnopharmacol. Jul. 1999;66(1):11-7.*

Wieboldt et al , Reduce your bird's food bill, Winged Wisdom, Pet Bird Magazine, Jan. 2000.*

I. Ikeda, The Journal of Japan Oil Chemists' Society, vol. 48, No. 10, pp. 21-28, 1999.

M. Igarashi et al., Cancer Letters, vol. 148, pp. 173-179, 2000.

The Journal of Japan Society for Bioscience, Biotechnology, and Agrochemistry, vol. 74, pp. 70, 2000.

R. Suzuki et al., Lipids, vol. 36, No. 5, pp. 477-482, 2001.

E. Cahoon et al., The Journal of Biological Chemistry, vol. 276, No. 4, pp. 2637-2643, 2001.

X. Qiu et al., Plant Physiology, Feb. 2001, vol. 125, pp. 847-855.

English Language Abstract of JP 2002-238566.

E. Hornung et al., Eur. J. Biochem., vol. 269, pp. 4852-4859, 2002.

J. Jaworski et al., Curr. Opin. Plant Bio., vol. 6, pp. 178-184, 2003.

C.D. Carpenter et al., Methods in Molecular biology, vol. 82, pp. 85-89.

E.G. Bligh et al., Canadian Journal of Biochemistry and Physiology, vol. 37, No. 8, pp. 911-917, Aug. 1959.

C. Uematsu et al., Plant Cell Reports, vol. 10, pp. 286-290, 1991.

L.G. Josefsson et al., The Journal of Biological Chemistry, vol. 262, No. 25, Sep. 15, 1987, pp. 12196-12201.

Junko Kohno-Murase et al., "Effects of an Antisense Napin Gene on Seed Storage Compounds in Transgenic *Brassica napus* Seeds", Plant Molecular Biology, vol. 26, pp. 1115-1124 (1994).

* cited by examiner

A

B

SEQUENCE LISTING

<160> NUMBER OF SEQ ID NOS: 24

<210> SEQ ID NO 1
<211> LENGTH: 387
<212> TYPE: PRT
<213> ORGANISM: Trichosanthes kirilowii

<400> SEQUENCE: 1

```
Met Gly Gly Gly Glu Gly Ile Glu Val Arg Ser Gly Ser Ser Ser Thr
 1               5                  10                  15

Lys Leu Ala Phe Gly Glu Arg Ile Thr His Ala Lys Pro Pro Phe Ser
             20                  25                  30

Ile Ser Gln Ile Lys Lys Ala Ile Pro Pro His Cys Phe Gln Arg Ser
         35                  40                  45

Leu Tyr Arg Ser Phe Ser Tyr Val Ile Phe Asp Phe Ile Phe Ala Ser
     50                  55                  60

Thr Phe Tyr His Ile Ala Ala Thr Asn Phe His Arg Leu Pro His Pro
 65                  70                  75                  80

Leu His Tyr Leu Ala Trp Pro Leu Tyr Trp Phe Cys Gln Gly Ser Val
                 85                  90                  95

Phe Thr Gly Leu Trp Val Ile Ala His Glu Cys Gly His Arg Ala Phe
            100                 105                 110

Ser Asp Tyr Gln Leu Val Asp Asp Val Val Gly Phe Leu Leu His Thr
        115                 120                 125

Ser Phe Leu Ile Pro Tyr Phe Ser Phe Lys Ile Ser His Arg Arg His
    130                 135                 140

His Ser Asn Thr Ala Ser Leu Glu Arg Asp Glu Val Phe Val Pro Lys
145                 150                 155                 160

Pro Lys Ala Lys Met Pro Trp Tyr Phe Lys His Leu Thr Asn Pro Pro
                165                 170                 175

Ala Arg Val Leu Ile Ile Phe Ile Thr Leu Thr Leu Gly Trp Pro Met
            180                 185                 190

Tyr Leu Ala Phe Asn Ile Ser Gly Arg Phe Tyr Glu Arg Phe Thr Ser
        195                 200                 205

His Phe Asp Pro Asn Ser Pro Ile Phe Ser Glu Asn Glu Trp Leu Gln
    210                 215                 220

Val His Ile Ser Asn Ala Gly Ile Val Ala Val Trp Tyr Leu Leu Tyr
225                 230                 235                 240
```

```
Lys Leu Ala Ala Ala Lys Gly Ile Ala Trp Val Ile Arg Met Tyr Val
                245                 250                 255

Val Pro Val Thr Ile Met Asn Ala Phe Val Leu Ile Thr Ser Leu
            260                 265                 270

Gln His Thr His Pro Ser Phe Pro Tyr Tyr Asp Ser Thr Glu Trp Asn
        275                 280                 285

Trp Leu Arg Gly Asn Leu Val Thr Leu Asp Arg Asp Tyr Gly Ile Leu
    290                 295                 300

Asn Lys Val Phe His Asn Ile Thr Asp Thr His Val His His Leu
305                 310                 315                 320

Phe Pro Ser Met Pro His Tyr Asn Ala Met Glu Ala Thr Arg Ala Val
                325                 330                 335

Lys Gln Val Leu Gly Glu Tyr Tyr His Phe Asp Gly Thr Pro Ile Phe
            340                 345                 350

Lys Ala Ala Trp Arg Glu Phe Arg Glu Cys Ile Tyr Val Glu Pro Asp
        355                 360                 365

Asn Asp Glu Gly Ala Ser Ser Ser Lys Gly Val Phe Trp Phe Arg
    370                 375                 380

Asn Lys Leu
385

<210> SEQ ID NO 2
<211> LENGTH: 1287
<212> TYPE: DNA
<213> ORGANISM: Trichosanthes kirilowii

<400> SEQUENCE: 2 tca ctt caa aga gag aag aga tcg aga atg gga ggt ggt gaa gga ata        48
                                Met Gly Gly Gly Glu Gly Ile
                                  1               5 gaa gtg cgc agc gga agc tca tca acc aaa ttg gcg ttt ggc gag cgc        96
Glu Val Arg Ser Gly Ser Ser Ser Thr Lys Leu Ala Phe Gly Glu Arg
        10                  15                  20 att aca cat gct aag cct ccc ttc agc att agt caa atc aag aaa gcc       144
Ile Thr His Ala Lys Pro Pro Phe Ser Ile Ser Gln Ile Lys Lys Ala
    25                  30                  35 att cct ccc cac tgc ttc caa cga tcc ctc tac cgt tct ttt tcc tac       192
Ile Pro Pro His Cys Phe Gln Arg Ser Leu Tyr Arg Ser Phe Ser Tyr
40                  45                  50                  55 gtt atc ttt gac ttc atc ttc gcc tct acc ttt tat cac atc gct gcc       240
Val Ile Phe Asp Phe Ile Phe Ala Ser Thr Phe Tyr His Ile Ala Ala
                60                  65                  70 acc aat ttc cac cgc ctt ccc cat cca ctg cac tac ctc gcc tgg cct       288
Thr Asn Phe His Arg Leu Pro His Pro Leu His Tyr Leu Ala Trp Pro
            75                  80                  85 ctt tat tgg ttt tgt caa ggc agc gtc ttc acc ggc ctc tgg gtc atc       336
Leu Tyr Trp Phe Cys Gln Gly Ser Val Phe Thr Gly Leu Trp Val Ile
        90                  95                 100 gct cac gag tgc ggc cat cgc gcc ttt agt gat tac caa ttg gta gac       384
Ala His Glu Cys Gly His Arg Ala Phe Ser Asp Tyr Gln Leu Val Asp
    105                 110                 115 gac gtc gtt ggc ttc ctc ctc cac act tct ttt ctc atc cct tac ttc       432
Asp Val Val Gly Phe Leu Leu His Thr Ser Phe Leu Ile Pro Tyr Phe
120                 125                 130                 135 tct ttc aaa atc agc cac cgc cgc cac cac tcc aac acc gca tcc ctc       480
Ser Phe Lys Ile Ser His Arg Arg His His Ser Asn Thr Ala Ser Leu
                140                 145                 150 gag cgg gac gag gtc ttt gtc ccc aag ccc aag gcc aaa atg ccc tgg       528
```

```
                                         Glu Arg Asp Glu Val Phe Val Pro Lys Pro Lys Ala Lys Met Pro Trp
                                                     155                 160                 165 tat ttc aag cac ttg acc aac cca ccc gct aga gtc ctc atc att ttc         576
Tyr Phe Lys His Leu Thr Asn Pro Pro Ala Arg Val Leu Ile Ile Phe
            170                 175                 180 atc acc ctt act cta ggc tgg cca atg tac tta gcc ttc aac att tct         624
Ile Thr Leu Thr Leu Gly Trp Pro Met Tyr Leu Ala Phe Asn Ile Ser
            185                 190                 195 ggc cga ttc tat gaa aga ttc acc agc cat ttc gat cca aat agc ccc         672
Gly Arg Phe Tyr Glu Arg Phe Thr Ser His Phe Asp Pro Asn Ser Pro
200                 205                 210                 215 ata ttc agc gaa aac gag tgg ctt cag gtt cac atc tcc aat gct ggg         720
Ile Phe Ser Glu Asn Glu Trp Leu Gln Val His Ile Ser Asn Ala Gly
                220                 225                 230 att gtg gcc gtg tgg tat ttg ctt tac aaa ttg gca gct gca aaa ggg         768
Ile Val Ala Val Trp Tyr Leu Leu Tyr Lys Leu Ala Ala Ala Lys Gly
                235                 240                 245 atc gct tgg gtc atc cgc atg tat gta gta ccc gta act att atg aat         816
Ile Ala Trp Val Ile Arg Met Tyr Val Val Pro Val Thr Ile Met Asn
            250                 255                 260 gcg ttt gta gtt ttg atc aca tcc ttg caa cac acc cac cct tca ttc         864
Ala Phe Val Val Leu Ile Thr Ser Leu Gln His Thr His Pro Ser Phe
265                 270                 275 cca tac tac gat tcc acg gaa tgg aat tgg cta aga gga aat ttg gtg         912
Pro Tyr Tyr Asp Ser Thr Glu Trp Asn Trp Leu Arg Gly Asn Leu Val
280                 285                 290                 295 aca ctg gat aga gat tat ggg att ttg aat aaa gtg ttt cat aat ata         960
Thr Leu Asp Arg Asp Tyr Gly Ile Leu Asn Lys Val Phe His Asn Ile
                300                 305                 310 acg gac acg cat gtg gtt cac cat ttg ttc cct tcg atg ccg cac tac        1008
Thr Asp Thr His Val Val His His Leu Phe Pro Ser Met Pro His Tyr
            315                 320                 325 aac gcc atg gag gcc acg aga gca gta aaa caa gtc ttg gga gag tac        1056
Asn Ala Met Glu Ala Thr Arg Ala Val Lys Gln Val Leu Gly Glu Tyr
            330                 335                 340 tac cat ttt gat ggg acg cct att ttc aag gct gcg tgg agg gag ttc        1104
Tyr His Phe Asp Gly Thr Pro Ile Phe Lys Ala Ala Trp Arg Glu Phe
            345                 350                 355 aga gag tgt att tat gtg gag cca gat aat gac gag ggc gct tcg tcc        1152
Arg Glu Cys Ile Tyr Val Glu Pro Asp Asn Asp Glu Gly Ala Ser Ser
360                 365                 370                 375 agt agt aag gga gtc ttc tgg ttt cgt aac aag ctc tga ata acc tct        1200
Ser Ser Lys Gly Val Phe Trp Phe Arg Asn Lys Leu ***
                380                 385 tgg ttt cat gat atc atc atc ttg att cca cat taa tca gtc atg aat        1248 aat cac ata tac caa taa ata tga tga aag aaa aaa tag                    1287

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: Synthetic
      DNA
<220> FEATURE:
<222> LOCATION: (6), (15)
<223> OTHER INFORMATION: n represents a, g, c or t

<400> SEQUENCE: 3
tgyggncayc aygcnttyag ygaytaycar t                                      31
```

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
     DNA
<220> FEATURE:
<222> LOCATION: (9), (12)
<223> OTHER INFORMATION: n represents a, g, c or t

<400> SEQUENCE: 4
agycaycgnc gncaccaytc caacac                                        26

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
     DNA
<220> FEATURE:
<222> LOCATION: (6), (15), (18), (21)
<223> OTHER INFORMATION: n represents a, g, c or t

<400> SEQUENCE: 5
ggrtgngtrt gytgnarnkm ngt                                           23

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
     DNA

<400> SEQUENCE: 6
atgggaggtg gtgaaggaat ag                                            22

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
     DNA

<400> SEQUENCE: 7
gatgatatca tgaaaccaag agg                                           23

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
     DNA

<400> SEQUENCE: 8
aaagagaagt aagggatgag aaa                                           23

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
     DNA

<400> SEQUENCE: 9
atgagaaaag aagtgtggag                                              20

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 10
gcagctgcaa aagggatcgc t                                            21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 11
atcgcttggg tcatccgcat g                                            21

<210> SEQ ID NO 12
<211> LENGTH: 395
<212> TYPE: PRT
<213> ORGANISM: Punica granatum

<400> SEQUENCE: 12

Met Gly Ala Asp Gly Thr Met Ser Pro Val Leu Thr Lys Arg Arg Pro
1               5                   10                  15

Asp Gln Glu Ile Asn Lys Leu Asp Ile Lys Pro Asn His Glu Val Asp
            20                  25                  30

Ile Ala Arg Arg Ala Pro His Ser Lys Pro Pro Phe Thr Leu Ser Asp
        35                  40                  45

Leu Arg Ser Ala Ile Pro Pro His Cys Phe His Arg Ser Leu Leu Met
    50                  55                  60

Ser Ser Ser Tyr Leu Ile Arg Asp Phe Ala Leu Ala Phe Leu Phe Tyr
65                  70                  75                  80

His Ser Ala Val Thr Tyr Ile Pro Leu Leu Pro Lys Pro Leu Ala Cys
                85                  90                  95

Met Ala Trp Pro Val Tyr Trp Phe Leu Gln Gly Ser Asn Met Leu Gly
            100                 105                 110

Ile Trp Val Ile Ala His Glu Cys Gly His Gln Ala Phe Ser Asn Tyr
        115                 120                 125

Gly Trp Val Asn Asp Ala Val Gly Phe Phe Leu His Thr Ser Leu Leu
    130                 135                 140

Val Pro Tyr Phe Pro Phe Lys Tyr Ser His Arg Arg His Ser Asn
145                 150                 155                 160

Thr Asn Ser Val Glu His Asp Glu Val Phe Val Pro Arg His Lys Asp
                165                 170                 175

Gly Val Gln Trp Tyr Tyr Arg Phe Phe Asn Asn Thr Pro Gly Arg Val
            180                 185                 190

Leu Thr Leu Thr Leu Thr Leu Leu Val Gly Trp Pro Ser Tyr Leu Ala
        195                 200                 205

Phe Asn Ala Ser Gly Arg Pro Tyr Asp Gly Phe Ala Ser His Tyr Asn

```
                210                 215                 220
Pro Asn Ala Gln Ile Phe Asn Leu Arg Glu Arg Phe Trp Val His Val
225                 230                 235                 240

Ser Asn Ile Gly Ile Leu Ala Ile Tyr Tyr Ile Leu Tyr Arg Leu Ala
                245                 250                 255

Thr Thr Lys Gly Leu Pro Trp Leu Leu Ser Ile Tyr Gly Val Pro Val
                260                 265                 270

Leu Ile Leu Asn Ala Phe Val Val Leu Ile Thr Phe Leu Gln His Ser
                275                 280                 285

His Pro Ala Leu Pro His Tyr Asn Ser Asp Glu Trp Asp Trp Leu Arg
                290                 295                 300

Gly Ala Leu Ala Thr Val Asp Arg Asp Tyr Gly Phe Leu Asn Glu Val
305                 310                 315                 320

Phe His Asp Ile Thr Asp Thr His Val Ile His His Leu Phe Pro Thr
                325                 330                 335

Met Pro His Tyr Asn Ala Lys Glu Ala Thr Val Ser Ile Arg Pro Ile
                340                 345                 350

Leu Lys Asp Tyr Tyr Lys Phe Asp Arg Thr Pro Ile Trp Arg Ala Leu
                355                 360                 365

Trp Arg Glu Ala Lys Glu Cys Leu Tyr Val Glu Ala Asp Gly Thr Gly
                370                 375                 380

Ser Lys Gly Val Leu Trp Phe Lys Ser Lys Phe
385                 390                 395

<210> SEQ ID NO 13
<211> LENGTH: 1374
<212> TYPE: DNA
<213> ORGANISM: Punica granatum

<400> SEQUENCE: 13
agagagctct gccggaaagt gctttttccaa cggcggagat caaggaaaag tggcaaagtg     60
gaaagcacct actactacac ccaaaaac atg gga gct gat gga aca atg tct cct    114
                                 Met Gly Ala Asp Gly Thr Met Ser Pro
                                  1               5 gtc cta acc aaa aga agg ccc gac caa gag atc aac aaa ctc gac ata        162
Val Leu Thr Lys Arg Arg Pro Asp Gln Glu Ile Asn Lys Leu Asp Ile
 10              15                  20                  25 aag cct aac cat gag gtc gac att gcc cga aga gcc cct cac tcg aag        210
Lys Pro Asn His Glu Val Asp Ile Ala Arg Arg Ala Pro His Ser Lys
                 30                  35                  40 ccg ccc ttc acc ttg agc gac ctc cgg agc gca atc ccg ccg cac tgc        258
Pro Pro Phe Thr Leu Ser Asp Leu Arg Ser Ala Ile Pro Pro His Cys
             45                  50                  55 ttc cac cgc tcg ctc ctc atg tcc tca tcg tac ctc atc cgc gac ttc        306
Phe His Arg Ser Leu Leu Met Ser Ser Ser Tyr Leu Ile Arg Asp Phe
         60                  65                  70 gcc cta gcc ttc ctc ttt tac cac tct gcc gtc act tac atc ccg ctc        354
Ala Leu Ala Phe Leu Phe Tyr His Ser Ala Val Thr Tyr Ile Pro Leu
     75                  80                  85 ctt ccg aaa cca ctt gcc tgc atg gct tgg ccg gtc tac tgg ttc ttg        402
Leu Pro Lys Pro Leu Ala Cys Met Ala Trp Pro Val Tyr Trp Phe Leu
 90                  95                 100                 105 cag gga tcg aac atg ctc ggc atc tgg gtc att gcc cac gag tgc ggc        450
Gln Gly Ser Asn Met Leu Gly Ile Trp Val Ile Ala His Glu Cys Gly
                110                 115                 120 cac cag gct ttc agc aat tac ggc tgg gta aat gat gca gtg ggc ttc        498
His Gln Ala Phe Ser Asn Tyr Gly Trp Val Asn Asp Ala Val Gly Phe
```

```
ttc ctc cac aca tcg ctc ctc gtc cca tac ttt cca ttt aag tac agc    546
Phe Leu His Thr Ser Leu Leu Val Pro Tyr Phe Pro Phe Lys Tyr Ser
            140                 145                 150 cac cgt cgc cac cac tcc aac acc aac tcc gtc gag cat gac gag gta    594
His Arg Arg His His Ser Asn Thr Asn Ser Val Glu His Asp Glu Val
    155                 160                 165 ttt gtc ccg agg cac aag gat ggt gtc cag tgg tat tac agg ttc ttc    642
Phe Val Pro Arg His Lys Asp Gly Val Gln Trp Tyr Tyr Arg Phe Phe
170                 175                 180                 185 aac aac acc cct ggc cga gtt cta acc cta acg ctg act cta ctg gtg    690
Asn Asn Thr Pro Gly Arg Val Leu Thr Leu Thr Leu Thr Leu Leu Val
                190                 195                 200 ggc tgg cca tca tac ctg gca ttc aat gcg tcg ggt agg ccc tat gat    738
Gly Trp Pro Ser Tyr Leu Ala Phe Asn Ala Ser Gly Arg Pro Tyr Asp
            205                 210                 215 ggc ttc gca tcc cat tac aac ccc aat gct cag ata ttc aac ttg aga    786
Gly Phe Ala Ser His Tyr Asn Pro Asn Ala Gln Ile Phe Asn Leu Arg
        220                 225                 230 gag cgg ttc tgg gtc cac gtc tcg aat atc ggg att tta gcc atc tac    834
Glu Arg Phe Trp Val His Val Ser Asn Ile Gly Ile Leu Ala Ile Tyr
    235                 240                 245 tac atc ctc tac cgg cta gcc acc acg aaa ggc ctc cca tgg ctt ctc    882
Tyr Ile Leu Tyr Arg Leu Ala Thr Thr Lys Gly Leu Pro Trp Leu Leu
250                 255                 260                 265 agc atc tac gga gtc cca gtc ctc ata tta aat gca ttc gtg gtg tta    930
Ser Ile Tyr Gly Val Pro Val Leu Ile Leu Asn Ala Phe Val Val Leu
                270                 275                 280 ata acc ttc ctt caa cac tct cat cct gca ctc ccc cac tac aac tca    978
Ile Thr Phe Leu Gln His Ser His Pro Ala Leu Pro His Tyr Asn Ser
            285                 290                 295 gac gaa tgg gac tgg ctg aga ggg gca cta gcc aca gtt gat cga gat   1026
Asp Glu Trp Asp Trp Leu Arg Gly Ala Leu Ala Thr Val Asp Arg Asp
        300                 305                 310 tac ggt ttt cta aac gag gtt ttc cac gac ata aca gac act cac gtg   1074
Tyr Gly Phe Leu Asn Glu Val Phe His Asp Ile Thr Asp Thr His Val
    315                 320                 325 atc cat cac ctc ttc cca aca atg ccc cat tac aat gcc aag gag gct   1122
Ile His His Leu Phe Pro Thr Met Pro His Tyr Asn Ala Lys Glu Ala
330                 335                 340                 345 act gtg tcc ata agg cca atc ttg aag gac tac tac aag ttt gat agg   1170
Thr Val Ser Ile Arg Pro Ile Leu Lys Asp Tyr Tyr Lys Phe Asp Arg
                350                 355                 360 acg ccc att tgg aga gca ttg tgg agg gag gcc aag gag tgt ttg tac   1218
Thr Pro Ile Trp Arg Ala Leu Trp Arg Glu Ala Lys Glu Cys Leu Tyr
            365                 370                 375 gta gaa gct gat ggc act ggc agc aaa ggg gtg cta tgg ttc aag agc   1266
Val Glu Ala Asp Gly Thr Gly Ser Lys Gly Val Leu Trp Phe Lys Ser
        380                 385                 390 aag ttc tga atgagtgtta ttagaatcga acctaatatc gagccagtcg agatatgagt 1325
Lys Phe
    395 tcataggttc aagggtccaa ctaaggttca atggatcaaa ccgtatgtt             1374
```

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Synthetic DNA
<220> FEATURE:
<222> LOCATION: (6), (12), (15), (21)
<223> OTHER INFORMATION: n represents a, g, c or t

<400> SEQUENCE: 14
tgyggncaym rngcnttyws ngaytaycar                              30

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA
<220> FEATURE:
<222> LOCATION: (9), (12)
<223> OTHER INFORMATION: n represents a, g, c or t

<400> SEQUENCE: 15
agycaycgnc gncaccaytc caacac                                  26

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      DNA
<220> FEATURE:
<222> LOCATION: (3), (6), (9)
<223> OTHER INFORMATION: n represents a, g, c or t

<400> SEQUENCE: 16
kynccnckna rccartycca ytc                                     23

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 17
atgggagctg atggaacaat gtctc                                   25

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 18
ctcgatatta ggttcgattc taataac                                 27

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 19
agagagctct gccggaaagt gc                                      22

```
<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 20
aacatacggt ttgatccatt gaacc                                              25

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 21
ggagcgatgt gtggaggaag aa                                                 22

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 22
tggaggaaga agcccactgc a                                                  21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 23
taccggctag ccaccacgaa a                                                  21

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 24
cccatggctt ctcagcatct ac                                                 22
```

GENES PARTICIPATING IN THE SYNTHESIS OF FATTY ACID HAVING TRANS-11-,CIS-13-CONJUGATED DOUBLE BOND AND UTILIZATION THEREOF

TECHNICAL FIELD

The present invention relates to a gene involved in synthesis of fatty acid having trans-11-, cis-13-conjugated double bonds, a vector and a transformant comprising the gene, and a use thereof.

1. Background Art

In general, it has been known that, among conjugated fatty acids, diene fatty acids, especially, conjugated linoleic acid has various pharmacological effects (Ikuo Ikeda, The Journal of Japan Oil Chemists' Society, Vol. 48, No. 10, pp. 21-28, 1999). However, with regard to triene fatty acids, it has only been known that eleostearic acid has an antitumor action against cancer cultured tissues (Cancer Lett 2000 Feb. 1; 148(2): 173-9), and that seed oil of *Catalpa ovata*, *Punica granatum* and *Aleurites fordii* containing triene fatty acids exhibits lethal activity against tumor cells (The Journal of Japan Society for Bioscience, Biotechnology, and Agrochemistry, Vol. 74, p. 70, 2000; Lipids, Vol. 36, No. 5, 477-482, 2001).

As a mechanism to produce conjugated triene fatty acids from linoleic acid in a plant, the mechanism by a conjugase that is a certain type of desaturating enzyme has been known. However, the majority of plants only have a desaturating enzyme which produces linolenic acid that is unconjugated triene fatty acid, and very few numbers of plants have a conjugase which produces conjugated triene fatty acid. The term "conjugase" used herein means an enzyme that introduces a conjugated unsaturated bond into fatty acid.

As an example of reports regarding a conjugase gene, International Publication WO00/11176 describes that a certain sequence and sequences showing homology of 45% or more thereto have a function of producing conjugated double bonds. More specifically, genes are reported which are involved in synthesis of eleostearic acid (18:3 (9c, 11t, 13t)) (wherein the first value represents the number of carbon atoms, the second value represents the number of unsaturated bonds, the value immediately after the number of unsaturated bonds in the parenthesis represents the position of the unsaturated bond, and c and t represent cis and trans, respectively) and parinaric acid (18:4 (9c, 11t, 13t, 15c)). In addition, there has also been reported a gene which is involved in synthesis of calendic acid (18:3 (8t, 10t, 12c)) that is a conjugated triene fatty acid (J. Biol. Chem. Vol. 276, No. 4, pp. 2637-2643, 2001; AF310155 AF310156; International Publication WO01/12800; Plant Physiology, February 2001, Vol. 125, pp. 847-855; AF343064). However, there have been no reports of genes which produces conjugated triene fatty acids other than those described above.

2. Disclosure of the Invention

As stated above, as genes involved in synthesis of conjugated triene fatty acids, only the genes of the enzyme which are involved in synthesis of eleostearic acid, parinaric acid and calendic acid have been isolated. Other conjugated triene fatty acids known to be accumulated in plant seeds (e.g., punicic acid, 18:3 (9c, 11t, 13c)) have not been developed for industrial applications, for the reasons that the ratio contained in seeds is low, that the amount of oil recovered from seeds is low, and that it is difficult to obtain a sufficient amount of seeds. Moreover, cloning of a gene involved in synthesis of punicic acid has not been reported.

Accordingly, an object to be solved by the present invention is to clone a gene which is involved in synthesis of fatty acid having trans-11-, cis-13-conjugated double bonds from fatty acid having double bond at position Δ12. Another object to be solved by the present invention is to introduce the above gene into a plant so as to allow the plant to produce and accumulate fatty acid having trans-11-, cis-13-conjugated double bonds such as punicic acid, thereby achieving industrial application of such conjugated fatty acid.

The present inventors have intensively studied to isolate a gene of an enzyme which is involved in synthesis of punicic acid from *Trichosanthes kirilowii* and *Punica granatum* that are known to accumulate punicic acid in seeds thereof. As a result, they have found that conjugases exist in *Trichosanthes kirilowii* and *Punica granatum*, and they have isolated the genes and then determined nucleotide sequences thereof. Moreover, the present inventors have introduced the isolated genes into yeast cells and plants to make it express therein, and they have analyzed fatty acids contained in such transformants, and have confirmed the production of punicic acid. The present invention has been completed based on these findings.

Thus, the present invention provides a gene having any one of the following nucleotide sequences:

(A) a nucleotide sequence encoding an amino acid sequence shown in SEQ ID NO: 1 or 12;

(B) a nucleotide sequence encoding an amino acid sequence comprising a deletion, addition or substitution of one or several amino acids with respect to the amino acid sequence shown in SEQ NO: 1 or 12, and having an ability of synthesizing fatty acid having trans-11-, cis-13-conjugated double bonds from fatty acid having a double bond at position Δ12;

(C) a nucleotide sequence shown in SEQ ID NO: 2 or 13;

(D) a nucleotide sequence comprising a deletion, addition or substitution of one or several nucleotides with respect to the nucleotide sequence shown in SEQ ID NO: 2 or 13, and encoding a protein having an ability of synthesizing fatty acid having trans-11-,cis-13-conjugated double bonds from fatty acid having a double bond at position Δ12; and (E) a nucleotide sequence hybridizing with the nucleotide sequence shown in SEQ ID NO: 2 or 13 or a complementary sequence thereof under stringent conditions, and encoding a protein having an ability of synthesizing fatty acid having trans-11-,cis-13-conjugated double bonds from fatty acid having a double bond at position Δ12.

In another aspect of the present invention, there is provided a protein having any one of the following amino acid sequences:

(A) an amino acid sequence shown in SEQ ID NO: 1 or 12; or (B) an amino acid sequence comprising a deletion, addition or substitution of one or several amino acids with respect to the amino acid sequence shown in SEQ ID NO: 1 or 12, and having an ability of synthesizing fatty acid having trans-11-, cis-13-conjugated double bonds from fatty acid having a double bond at position Δ12.

The ability of synthesizing fatty acid having trans-11-, cis-13-conjugated double bonds from fatty acid having a double bond at position Δ12 is preferably an ability of synthesizing punicic acid from linoleic acid.

In another aspect of the present invention, there is provided a vector comprising the gene of the present invention as mentioned above.

In another aspect of the present invention, there is provided a transformed host cell having the gene or vector of the present invention as mentioned above.

The transformed host cell is preferably a transformed plant cell.

In another aspect of the present invention, there is provided a method for producing fatty acid having trans-11-, cis-13-conjugated double bonds from fatty acid having a double bond at position Δ12, wherein the above protein of the present invention is used.

In another aspect of the present invention, there is provided a method for producing fatty acid having trans-11-, cis-13-conjugated double bonds, wherein the above transformed host cell of the present invention is cultured, and fatty acid having trans-11-, cis-13-conjugated double bonds which is produced by the above transformed host cell is collected.

In another aspect of the present invention, there is provided a method for increasing the amount of fatty acid having trans-11-, cis-13-conjugated double bonds produced by host cells, wherein a host cell is transformed with the above gene or vector of the present invention, and the transformed host cell producing an increased amount of fatty acid having trans-11-, cis-13-conjugated double bonds as compared with the untransformed host cell is selected.

In another aspect of the present invention, there is provided a primer set consisting of a combination of a primer having a nucleotide sequence shown in SEQ ID NO: 3 or 4 and a primer having a nucleotide sequence shown in SEQ ID NO: 5.

In another aspect of the present invention, there is provided a primer set consisting of a combination of primers having nucleotide sequences shown in SEQ ID NOS: 6 and 7.

In another aspect of the present invention, there is provided a primer set consisting of a combination of a primer having a nucleotide sequence shown in SEQ ID NO: 14 or 15 and a primer having a nucleotide sequence shown in SEQ ID NO: 16.

In another aspect of the present invention, there is provided a primer set consisting of a combination of a primer having a nucleotide sequence shown in SEQ ID NO: 17 or 19 and a primer having a nucleotide sequence shown in SEQ ID NO: 18 or 20.

In another aspect of the present invention, there is provided an oligonucleotide selected from a group consisting of: a sense oligonucleotide having the same sequence as a sequence corresponding to 5 to 100 contiguous nucleotides in any one of the nucleotide sequences (A) to (E) as described above; an antisense oligonucleotide having a sequence complementary to the above sense nucleotide; and an oligonucleotide derivative of the above sense or antisense oligonucleotide.

In another aspect of the present invention, there are provided seeds obtained from the transformed plant of the present invention as mentioned above.

In another aspect of the present invention, there is provided a seed oil obtained from the seeds of the present invention as mentioned above.

In another aspect of the present invention, there is provided a method for increasing the content of fatty acids having trans-11-, cis-13-conjugated double bonds and/or a derivative thereof in a host cell, which comprises the steps of: (a) transforming a host cell with a gene encoding a protein having an ability of synthesizing fatty acid having trans-11-, cis-13-conjugated double bonds from fatty acid having a double bond at position Δ12; (b) allowing the host cell to grow under appropriate conditions to allow the above gene to be expressed; and (c) selecting host cells comprising an increased amount of fatty acids having trans-11-, cis-13-conjugated double bonds and/or derivatives thereof.

In another aspect of the present invention, there is provided a method for increasing the content of fatty acid having trans-11-, cis-13-conjugated double bonds and/or derivatives thereof in a host cell, which comprises the steps of: (a) transforming a host cell with a gene encoding the above protein of the present invention; (b) allowing the host cell to grow under appropriate conditions to allow the above gene to be expressed; and (c) selecting host cells comprising an increased amount of fatty acids having trans-11-, cis-13-conjugated double bonds and/or derivatives thereof.

In another aspect of the present invention, there is provided a method for producing a seed oil, which comprises the steps of: (a) transforming a plant cell with a gene encoding a protein having an ability of synthesizing fatty acid having trans-11-, cis-13-conjugated double bonds from fatty acid having a double bond at position Δ12; (b) growing a plant body having fertility from the obtained transformed plant cell; (c) obtaining progeny seeds from the obtained plant body having fertility, and selecting from the obtained progeny seeds, those comprising an increased amount of fatty acids having trans-11-, cis-13-conjugated double bonds and/or derivatives thereof; and (d) obtaining oil comprising an increased amount of fatty acids having trans-11-, cis-13-conjugated double bonds and/or derivatives thereof from the obtained progeny seeds.

In another aspect of the present invention, there is provided a method for producing a seed oil, which comprises the steps of: (a) transforming a plant cell with a gene encoding the above protein of the present invention; (b) growing a plant body having fertility from the obtained transformed plant cell; (c) obtaining progeny seeds from the obtained plant body having fertility, and selecting from the obtained progeny seeds, those comprising an increased amount of fatty acids having trans-11-, cis-13-conjugated double bonds and/or derivatives thereof; and (d) obtaining oil comprising an increased amount of fatty acids having trans-11-, cis-13-conjugated double bonds and/or derivatives thereof from the obtained progeny seeds.

In another aspect of the present invention, there is provided a seed oil which is obtained by the above method for producing a seed oil according to the present invention.

In another aspect of the present invention, there is provided functional health beverage and food comprising the above seeds of the present invention or a treated product thereof, or the seed oil of the present invention or a treated product thereof.

In another aspect of the present invention, there is provided an animal feed comprising the above seed of the present invention or a treated product thereof, or the seed oil of the present invention or a treated product thereof.

In another aspect of the present invention, there is provided cis-9-, trans-11-,cis-13-hexadecatrienoic acid.

In another aspect of the present invention, there is provided cis-11-, trans-13-,cis-15-eicosatrienoic acid.

BEST MODE FOR CARRYING OUT THE INVENTION

Figure 1:
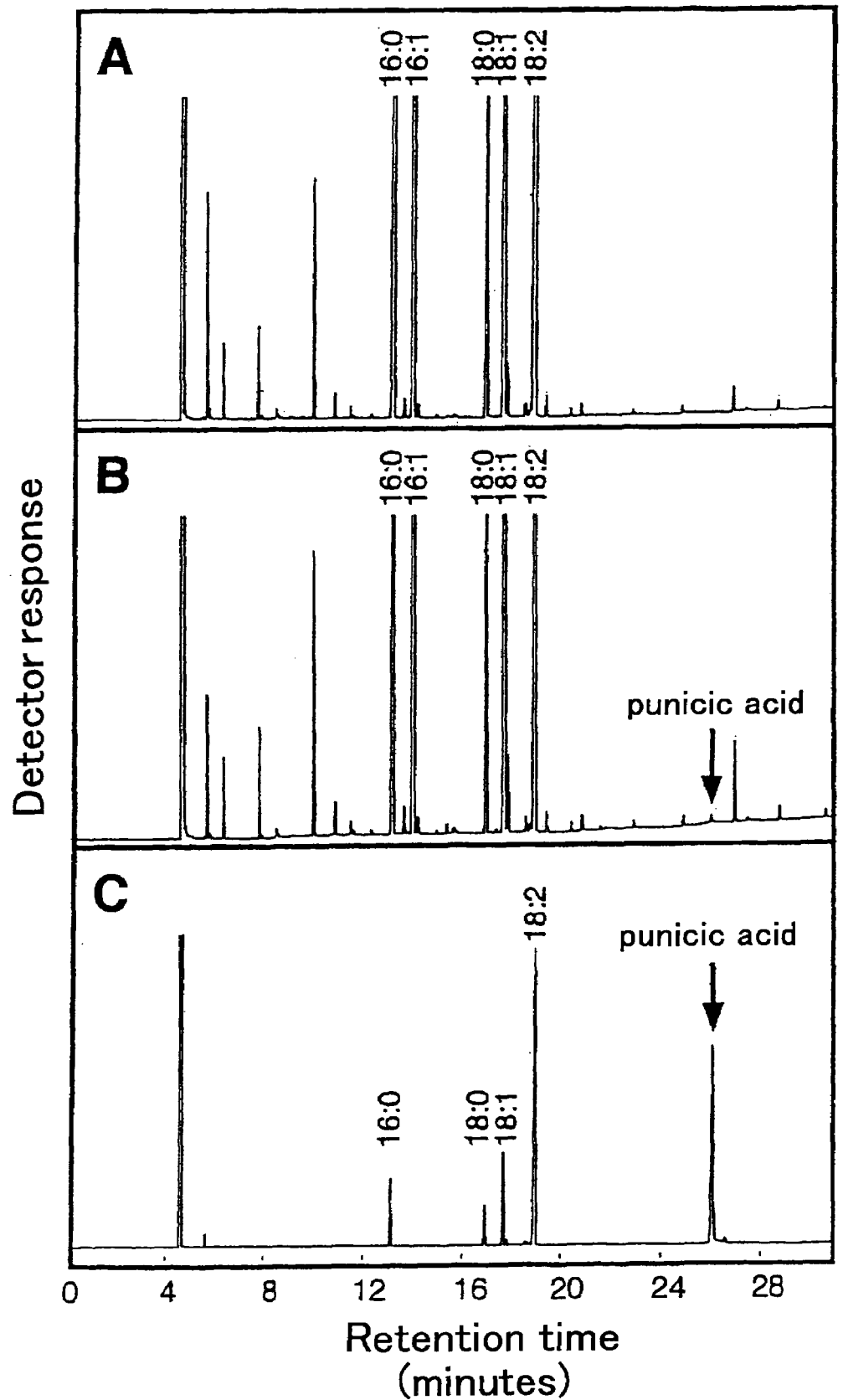
FIG. 1 shows results obtained by GC analyses of fatty acid methyl esters prepared from each of yeast cells (A) into which pYES2 was introduced, yeast cells (B) into which pYES2/TkFac was introduced, and immature seeds (C) of *Trichosanthes kirilowii*. The yeast cells were cultured in a medium to which linoleic acid was added.

The embodiments of the present invention and the methods for carrying out the present invention will be described in detail below.

(1) Gene and Protein of the Present Invention

The present invention relates to a gene having any one of the following nucleotide sequences:

(A) a nucleotide sequence encoding an amino acid sequence shown in SEQ ID NO: 1 or 12;

(B) a nucleotide sequence encoding an amino acid sequence comprising a deletion, addition or substitution of one or several amino acids with respect to the amino acid sequence shown in SEQ NO: 1 or 12, and having an ability of synthesizing fatty acid having trans-11-, cis-13-conjugated double bonds from fatty acid having a double bond at position Δ12;

(C) a nucleotide sequence shown in SEQ ID NO: 2 or 13;

(D) a nucleotide sequence comprising a deletion, addition or substitution of one or several nucleotides with respect to the nucleotide sequence shown in SEQ ID NO: 2 or 13, and encoding a protein having an ability of synthesizing fatty acid having trans-11-, cis-13-conjugated double bonds from fatty acid having a double bond at position Δ12; and (E) a nucleotide sequence hybridizing with the nucleotide sequence shown in SEQ ID NO: 2 or 13 or a complementary sequence thereof under stringent conditions, and encoding a protein having an ability of synthesizing fatty acid having trans-11-, cis-13-conjugated double bonds from fatty acid having a double bond at position Δ12.

Moreover, the present invention relates to a protein having either one of the following amino acid sequences:

(A) an amino acid sequence shown in SEQ ID NO: 1 or 12; or (B) an amino acid sequence comprising a deletion, addition or substitution of one or several amino acids with respect to the amino acid sequence shown in SEQ ID NO: 1 or 12, and having an ability of synthesizing fatty acid having trans-11-, cis-13-conjugated double bonds from fatty acid having a double bond at position Δ12.

In the present specification, the phrase "an amino acid sequence comprising a deletion, addition or substitution of one or several amino acids" is used to mean an amino acid sequence comprising a deletion, addition or substitution of any number of, for example 1 to 20, preferably 1 to 15, more preferably 1 to 10, and further more preferably 1 to 5 of amino acids.

In the present specification, the phrase "a nucleotide sequence comprising a deletion, addition or substitution of one or several nucleotides" is used to mean a nucleotide sequence comprising a deletion, addition or substitution of any number of, for example 1 to 20, preferably 1 to 15, more preferably 1 to 10, and further more preferably 1 to 5 of nucleotides.

In the present specification, the phrase "a nucleotide sequence hybridizing with . . . under stringent conditions" is used to mean the nucleotide sequence of DNA obtained by the colony hybridization method, the plaque hybridization method, the southern hybridization method, or the like using DNA as a probe. An example of such DNA may include DNA which is obtained by using a filter to which DNA derived from a colony or plaque, or a fragment thereof is fixed, subjecting the filter to hybridization at 65° C. in the presence of 0.7 to 1.0 M NaCl, and washing the filter at 65° C. with a 0.1 to 2×SSC solution (1×SSC consisting of 150 mM sodium chloride and 15 mM sodium citrate), so that the DNA can be identified. Hybridization can be carried out according to the method described in Molecular Cloning; A laboratory Manual, $2^{nd}$ Ed., Cold Spring Harbor Laboratory, Cold Spring Harbor, N.Y., 1989 (hereinafter abbreviated to as "Molecular Cloning $2^{nd}$ Ed."), and the like.

An example of DNA hybridizing under stringent conditions may include DNA having a certain degree of homology with the nucleotide sequence of DNA used as a probe. The term "a certain degree of homology" used herein means, for example 70% or more, preferably 80% or more, more preferably 90% or more, further more preferably 93% or more, particularly preferably 95% or more, and most preferably 98% or more.

The phrase "having an ability of synthesizing fatty acid having trans-11-, cis-13-conjugated double bonds from fatty acid having a double bond at position Δ12" used in the present specification means that fatty acid having trans-11-, cis-13-conjugated double bonds is synthesized from fatty acid having a double bond at position Δ12 by allowing the gene to be expressed in a host. One of examples thereof may include an ability of synthesizing punicic acid from unconjugated dienes. A particularly preferred example may include an ability of synthesizing punicic acid from linoleic acid.

The type of a host is not particularly limited, but preferred examples may include bacteria, yeasts or plants. Such a description that fatty acid having trans-11-, cis-13-conjugated double bonds is synthesized from fatty acid having a double bond at position Δ12 by allowing the gene to be expressed in a host, means, more specifically, that a host having the above gene produces a larger amount of fatty acid having trans-11-, cis-13-conjugated double bonds than a host not having the above gene does.

A method for obtaining the gene of the present invention is not particularly limited. An appropriate probe or primers are prepared on the basis of the information on the amino acid sequences or nucleotide sequences of SEQ ID NOS: 1, 2, 12 and 13 disclosed in the present specification, and using them, a cDNA library in which the present gene is predicted to exist is screened, and thus a gene of interest can be isolated.

Specifically, according to common methods, a cDNA library is prepared from an appropriate plant origin in which the gene of the present invention is expressed, such as *Trichosanthes kirilowii* (Kikarasuuri) or *Punica granatum* (Zakuro), which is known that punicic acid exists in their seeds and from which the gene of the present invention was isolated, or *Cyclanthera explodens* (Bakudanuri) or *Cayaponia Africana* (Japanese name: unknown), which is known that punicic acid exists therein. Subsequently, a desired clone is selected from the prepared cDNA library using an appropriate probe that is specific for the gene of the present invention.

In the above description, examples of the origin of cDNA may include various cells or tissues derived from the aforementioned plants. A preferred example may include immature seed embryos.

In addition, isolation of total RNA from these plant origins, isolation or purification of mRNA, obtainment of cDNA, and cloning thereof, can be all carried out according to common methods.

The gene of the present invention can be screened from a cDNA library by a method commonly used by a person skilled in the art, such as the method described in Molecular Cloning $2^{nd}$ Ed., 8.3-8.86, 1989.

As a probe used in the screening of the gene of the present invention, DNA chemically synthesized on the basis of the information on the nucleotide sequence of the gene of the present invention can be generally used, but the gene of the present invention or a fragment thereof that had already been obtained may also be used. Moreover, a sense primer and an antisense primer that are designed on the basis of the information of the nucleotide sequence of the gene of the present invention may also be used as a probe for screening. Any portion of the nucleotide sequence of the gene of the present invention can be used as such a primer. However, from the viewpoint of the size of a fragment amplified by PCR or homology with other conjugase genes, it is preferable to use a primer having the nucleotide sequence shown in SEQ ID NO: 3 or 4 and a primer having the nucleotide sequence shown in SEQ ID NO: 5 in combination, or to use a primer having the nucleotide sequence shown in SEQ ID NO: 14 or 15 and a primer having the nucleotide sequence shown in SEQ ID NO: 16 in combination.

Each of the symbols used in the sequence listing of the present specification means the following:
k represents G or T.
m represents A or C.
n represents any given nucleotide (A, C, G or T).
r represents A or G.
s represents C or G.
w represents A or T.
y represents C or T.

Considering the fact that multiple nucleotide sequences encode a single amino acid, it is desired that used primers be given in consideration of degeneracy.

A primer having a desired nucleotide sequence such as one shown in SEQ ID NO: 3, 4, 5, 14, 15 or 16 can be easily synthesized using a DNA synthesizer.

An example of a nucleotide sequence used as the aforementioned probe may include a partial nucleotide sequence corresponding to the gene of the present invention, which has at least 15 contiguous nucleotides, preferably 20 or more contiguous nucleotides, more preferably 30 or more contiguous nucleotides, and most preferably 50 or more contiguous nucleotides. Otherwise, a positive clone having the above nucleotide may be directly used as a probe.

To obtain the gene of the present invention, a DNA/RNA amplification method using PCR may also be applied. This is to say, cDNA is synthesized with reverse transcriptase, using RNA as a template. The thus synthesized cDNA is then subjected to PCR using an appropriate primer set, so as to obtain a partial fragment of a gene sequence of interest (RT-PCR method). Based on the information on the nucleotide sequence of the obtained partial fragment, the entire nucleotide sequence of a gene of interest is determined by the 5'- and 3'-RACE method. Thereafter, primers having nucleotide sequences of the 3'- and 5'-ends of the gene are synthesized, and the full length of the gene can then be isolated. Primers used in such a PCR method can be appropriately designed based on the information of the nucleotide sequence of the gene of the present invention, which was determined by the present invention, and the primers can be synthesized by common methods. The amplified DNA/RNA fragment can be isolated and purified by common methods such as gel electrophoresis.

Moreover, the gene of the present invention or various types of DNA fragments obtained by the aforementioned methods can be sequenced by common methods.

An example of the thus obtained gene of the present invention may include a gene having a nucleotide sequence encoding a protein consisting of amino acids shown in SEQ ID NO: 1 or 12. However, the gene of the present invention is not limited thereto, and it includes homologues of the present gene.

The term "homologues of the present gene" is used herein to mean a series of associated genes, which have sequence homology with the gene of the present invention (or with gene products thereof) and are recognized to be members of the same gene family because of the aforementioned structural features and the above described similarity of biological functions. As a matter of course, alleles of the gene of the present invention are included therein.

The gene of the present invention is not limited to genes having the above specific nucleotide sequences, but it can also have a nucleotide sequence obtained by combining any given codon with respect to each amino acid residue and then selecting it therefrom. Codons can be selected by common methods. For example, codons are selected considering frequency in the use of codons in the used host. Moreover, as stated above, the gene of the present invention also includes DNA hybridizing with DNA having the nucleotide sequence shown in SEQ ID NO: 2 or 13 or a complementary sequence thereof, under stringent conditions. Such DNA has a certain degree of homology with DNA having the nucleotide sequence shown in SEQ ID NO: 2 or 13.

The above DNA having a certain degree of homology means a polynucleotide encoding a polypeptide comprising an amino acid sequence shown in SEQ ID NO: 1 or 12, or a polynucleotide or a complementary strand polynucleotide thereof, which has at least 50%, preferably at least 80%, and more preferably at least 90% homology with the nucleotide sequence shown in SEQ ID NO: 2 or 13.

An example of such a gene may include a gene having a nucleotide sequence hybridizing with the nucleotide sequence shown in SEQ ID NO: 2 or 13, or DNA having a sequence complementary thereto, under stringent conditions such as in 0.2×SSC containing 0.1% SDS at 50° C. or in 1×SSC containing 0.1% SDS at 60° C.

Furthermore, among the genes of the present invention, particularly those having the following nucleotide sequences (B) and (D) can be produced by any methods known to a person skilled in the art, such as chemical synthesis, genetic engineering techniques, or mutagenesis: (B) a nucleotide sequence encoding an amino acid sequence comprising a deletion, addition or substitution of one or several amino acids with respect to the amino acid sequence shown in SEQ NO: 1 or 12, and having an ability of synthesizing fatty acid having trans-11-, cis-13-conjugated double bonds from fatty acid having a double bond at position Δ12; and (D) a nucleotide sequence comprising a deletion, addition or substitution of one or several nucleotides with respect to the nucleotide sequence shown in SEQ ID NO: 2 or 13, and encoding a protein having an ability of synthesizing fatty acid having trans-11-, cis-13-conjugated double bonds from fatty acid having a double bond at position Δ12. Specifically, a mutant gene can be obtained by introducing mutation into DNA having the nucleotide sequence shown in SEQ ID NO: 2 or 13.

To obtain a mutant gene, known methods such as those using a random mutant, a targeted mutant, or a synthetic gene can be used (refer to Shin Idensi Kogaku Handbook (Handbook for New Genetic Engineering), Jikken Igaku (Experimental Medicine), supplementary volume, Yodosha Co., Ltd., 1996).

Specifically, such a mutant gene can be obtained by a method of bringing an agent as a mutagen into contact with the DNA having the nucleotide sequence shown in SEQ ID NO: 2 or 13 and reacting the agent therewith, a method of applying ultraviolet light, a genetic engineering technique, etc. One of genetic engineering techniques, a site-directed mutagenesis, is useful as a technique for introducing a specific mutation into a specific site. This technique can be carried out according to the method described in Molecular Cloning $2^{nd}$ Ed.

Using a part or the entire nucleotide sequence of the gene of the present invention, the presence of the gene of the present invention in a plant body or partial tissues thereof in which the presence of punicic acid has already been confirmed, and the presence or absence of the expression of the gene therein, can also be characteristically detected. Moreover, the gene of the present invention can also be used to confirm the presence of the gene of the present invention in a plant body or partial tissues thereof in which the presence of punicic acid has not yet been confirmed at present, and the presence or absence of the expression therein.

(2) Vector Comprising the Gene of the Present Invention Involved in Synthesis of Fatty Acid Having Trans-11-, Cis-13-Conjugated Double Bonds The gene of the present invention can be incorporated into a suitable vector and can be used as a recombinant vector. The type of the vector may be either an expression vector or non-expression vector, and can be selected depending on purposes.

As a cloning vector, a vector capable of autonomously replicating in *Escherichia coli* K12 is preferred. Either a phage vector or plasmid vector can be used as such a cloning vector. An expression vector for *Escherichia coli* may also be used as a cloning vector. Examples of such a vector may include ZAP Express [manufactured by Stratagene, Strategies, 5, 58 (1992)], pBluescript II SK(+) [Nucleic Acids Research, 17, 9494(1989)], Lambda ZAP II (manufactured by Stratagene), λgt10 and λgt11 [DNA Cloning, A Practical Approach, 1, 49 (1985)], λTriplEx (manufactured by Clontech), λExCell (manufactured by Pharmacia), pT7T318U (manufactured by Pharmacia), pcD2 [Mol. Cen. Biol., 3, 280 (1983)], pMW218 (Wako Pure Chemical Industries, Ltd.), pUC118 (manufactured by Takara Bio Inc.), pGEM-3Z (Manufactured by Promega), pGEM-T Easy (manufactured by Promega), pCR2.1 (manufactured by Invitrogen), pEG400 [J. Bacteriol., 172, 2392 (1990)], and pQE-30 (manufactured by QIAGEN).

An expression vector can be selected in consideration of a combination with a host. A vector capable of autonomously replicating in a host cell or being incorporated into a chromosome, and containing a promoter at a position which enables transcription of the gene of the present invention, can be preferably used.

Where bacteria are used as host cells, it is preferable that an expression vector for expressing DNA can autonomously replicate in the bacteria and that it is a recombinant vector comprising a promoter, a ribosome binding sequence, the above DNA and a transcription termination sequence. A gene for regulating a promoter may also be contained therein.

Examples of an expression vector for bacteria may include pBTrP2, pBTac1 and pBTac2 (all of which are commercially available from Boehringer Mannheim), pKK133-2 (manufactured by Pharmacia), pSE280 (manufactured by Invitrogen), pGEMEX-1 (Manufactured by Promega), pQE-8 (manufactured by QIAGEN), pQE-30 (manufactured by QIAGEN), pKYP10 (Japanese Patent Laid-Open No. 58-110600), pKYP200 [Agrc. Biol. Chem., 48, 669 (1984)], PLSA1 [Agrc. Biol. Chem., 53, 277 (1989)], pGEL1 [Proc. Natl. Acad. Sci. USA, 82, 4306 (1985)], pBluescript II SK(+), pBluescript II SK(−) (manufactured by Stratagene) pTrS30 (FERM BP-5407), pTrS32 (FERM BP-5408), pGEX (manufactured by Pharmacia), pRSET, pTrcHis and pTrcHis2 (all of which are manufactured by Invitrogen), pET-3 (manufactured by Novagen), pTerm2 (U.S. Pat. No. 4,686,191, U.S. Pat. No. 4,939,094, U.S. Pat. No. 5,160,735), pSupex, pUB110, pTP5, pC194, pUC18 [Gene, 33, 103(1985)], pUC19 [Gene, 33, 103(1985)], pSTV28 (manufactured by Takara Bio Inc.), pSTV29 (manufactured by Takara Bio Inc.), pUC118 (manufactured by Takara Bio Inc.), pPA1 (Japanese Patent Laid-Open No. 63-233798), pEG400 [J. Bacteriol., 172, 2392 (1990)], and pQE-30 (manufactured by QIAGEN).

Examples of a promoter for bacteria may include promoters derived from *Escherichia coli,* phage and others, such as a trp promoter (P trp), lac promoter (P lac), trc promoter (P trc), T7 promoter (P T7), PL promoter, PR promoter or PSE promoter; an SP01 promoter; an SP02 promoter; and a penP promoter.

Examples of an expression vector for yeast may include pYES2 (manufactured by Invitrogen), pESC and pESP (both of which are manufactured by Stratagene), pAUR (manufactured by Takara Bio Inc.), YEp13(ATCC37115), YEp24 (ATCC37051), Ycp50(ATCC37419), pHS19 and pHS15. Examples of a promoter for yeast may include a PH05 promoter, a PGK promoter, a GAP promoter, an ADH promoter, a gall promoter, a gal10 promoter, a heat shock protein promoter, an MFα1 promoter and a CUP1 promoter.

Examples of an expression vector for animal cells may include pcDNAI, pcDM8 (commercially available from Funakoshi Co., Ltd.), pAGE107 [Japanese Patent Laid-Open No. 3-22979; Cytotechnology, 3, 133, (1990)], pAS3-3 (Japanese Patent Laid-Open No. 2-227075), pCDM8 [Nature, 329, 840, (1987)], pcDNAI/AmP (manufactured by Invitrogen), pREP4 (manufactured by Invitrogen), pAGE103 [J. Blochem., 101, 1307 (1987)] and pAGE210. Examples of a promoter for animal cells may include a cytomegalovirus (human CMV) IE (immediate early) promoter, an SV40 early promoter, a retrovirus promoter, a metallothionein promoter, a heat shock promoter and an SRα promoter.

Examples of an expression vector for plant cells may include pIG121-Hm [Plant Cell Report, 15, 809-814 (1995)], and pBI121 [EMBO J. 6, 3901-3907 (1987)]. An example of a promoter for plant cells may include a cauliflower mosaic virus 35S promoter [Mol. Gen. Genet (1990) 220, 389-392]. The details will be described later in the specification.

(3) Transformant Having the Gene of the Present Invention

The transformant having the gene of the present invention (that is, a transformed host cell) can be prepared by introducing the above recombinant vector (preferably an expression vector) into a host.

Examples of bacterial host cells may include microorganisms belonging to *Escherichia, Corynebacterium, Brevibacterium, Bacillus, Microbacterium, Serratia, Pseudomonas, Agrobacterium, Alicyclobacillus, Anabaena, Anacystis, Arthrobacter, Azobacter, Chromatium, Erwinia, Methylobacterium, Phormidium, Rhodobacter, Rhodopseudomonas, Rhodospirillum, Scenedesmun, Streptomyces, Synnecoccus* or *Zymomonas*. Examples of a method of introducing a recombinant vector into bacterial host may include a method using a calcium ion, the electroporation, and the protoplast method.

Examples of yeast host may include *Saccharomyces cerevisiae, Schizosaccharomyces pombe, Kluyveromyces lactis, Trichosporon pullulans,* and *Schwanniomyces alluvius*.

To introduce a recombinant vector into yeast host, any method of introducing DNA into yeast can be used. Examples of such a method may include the electroporation, the spheroplast method, and the lithium acetate method.

Examples of an animal cell host may include a HeLa cell, a Namalva cell, a COS1 cell, a COS7 cell and a CHO cell.

To introduce a recombinant vector into an animal cell, any method of introducing DNA into an animal cell can be used. Examples of such a method may include the electroporation, the calcium phosphate method, and the lipofection method.

When a plant cell is transformed, a host can be freely selected depending on the intended use of the transformant (e.g., mass production of fatty acid having trans-11-, cis-13-conjugated double bonds, such as punicic acid).

According to the present invention, a plant body is transformed with the aforementioned gene, so that fatty acid having trans-11-, cis-13-conjugated double bonds can be accumulated in the plant.

The plant species into which the gene of the present invention can be introduced is not particularly limited. Examples of such a plant may include: oil-producing crops such as rapeseeds, soybeans, sunflower or palm; cereal crops such as rice, corn or wheat; various species of vegetables such as cabbage or lettuce; trees; and flowering plants.

In the present specification, examples of a plant source to be transformed may include seeds, seedlings, plantlet, callus, cultured cells, and plant bodies. As a person skilled in the art generally carries out, a preferred site may be appropriately selected from a target plant. For example, seedlings or protoplasts may be selected from rapeseed; seedlings, callus or cultured cells may be selected from soybean; seedlings may be selected from sunflower; callus or cultured cells may be selected from palm; seedlings, callus, cultured cells or protoplasts may be selected from rice; seedlings, plantlet, callus, cultured cells or protoplasts may be selected from corn; seedlings, callus or cultured cells may be selected from wheat; seedlings, callus, cultured cells or protoplasts may be selected from cabbage; and seedlings, callus, cultured cells or protoplasts may be selected from lettuce.

Plants can be transformed by common methods. Examples may include methods of directly introducing DNA into a cell, such as a method using *Agrobacterium,* the electroporation, the DEAE dextran method, the calcium lithium method, the polyethylene glycol method, or the particle gun. An expression cassette to be incorporated can be prepared by common methods, using known plasmids.

A vector used to introduce the gene of the present invention into a plant body for transformation preferably contains a promoter capable of expressing the gene in a tissue synthesizing lipids. Examples of a promoter may include a promoter for expression specific to seeds, and a promoter for expression in leaves. For seed-specific expression, there can be used promoters of genes encoding proteins accumulated in seeds, such as napin, cruciferin, glutelin, prolamin or glycine, or promoters of genes encoding proteins that constitutes oil body which accumulates proteins or lipids including enzymes associated with lipid synthesis. For example, a promoter of a gene encoding an acetyl CoA binding protein or oleosin can be used. For expression in leaves, promoters of genes which encode a cauliflower mosaic virus 35S protein or Rubisco small subunit can be used.

Nopaline synthetase terminator is an example of terminators used herein.

Moreover, two types of vectors are used herein depending on methods of introducing the above gene into a plant. Where the gene is introduced via *Agrobacterium,* there is used a binary vector comprising a selective marker for selecting a transformed plant, such as a kanamycin resistant gene or hygromycin resistant gene, and a 25-bp border sequence. On the other hand, where the gene is physically introduced, a plasmid derived from Escherichia coli containing the above resistant genes, for example, a vector such as pUC, is used.

The content of fatty acids in seeds is determined by common methods. For example, fatty acid methyl esters are prepared from leaves or seeds used as materials according to the method of Browse et al. (Anal. Biochem. 152, 141-145, 1985), and the obtained fatty acid methyl esters are extracted with hexane, followed by analysis by gas chromatography (Plan Physiol. Biochem. 30, 425-434, 1992).

Seeds obtained from the transformed plant cells obtained by the above described method, and seed oil obtained from the seeds are also included in the scope of the present invention.

Extraction of seed oil from seeds can be carried out by known methods. The origin of plant seeds as raw materials is not particularly limited. Examples of such an origin may include seeds of plants belonging to *Punicaceae*, *Compositae*, *Euphordiaceae*, *Cucuritaceae*, *Bignoniaceae*, *Balsaminaceae*, *Gramineae*, *Pedaliaceae*, *Leguminosae*, *Cruciferae*, *Malraceae*, or *Palmae*.

(4) Production of the Enzyme Protein of the Present Invention Involved in Synthesis of Fatty Acid Having Trans-11-, Cis-13-Conjugated Double Bonds The transformed host cell having the gene of the present invention involved in synthesis of fatty -acid having trans-11-, cis-13-conjugated double bonds is cultured, and an enzyme protein involved in synthesis of fatty acid having trans-11-, cis-13-conjugated double bonds is produced and accumulated in the culture. The protein is then collected from the culture, and thus the protein of the present invention can be obtained.

The transformed host cell having the gene of the present invention can be cultured by a method commonly used in culture of a host.

Where the transformed host cell of the present invention is prokaryote such as *Escherichia coli* or eukaryote such as yeast, a medium in which these microorganisms are cultured may be either a natural medium or synthetic medium, as long as it contains a carbon source that can be assimilated by the microorganisms, nitrogen source and inorganic salts, and the transformed host cell can be efficiently cultured therein. As a culture method, a shake culture or depth aeration agitation culture is preferably carried out under aerobic conditions. The culture temperature is generally between 15° C. and 40° C., and the culture time is generally between 16 hours and 7 days. The pH for culture is maintained between 3.0 and 9.0. The pH is adjusted using inorganic or organic acid, an alkali solution, urea, calcium carbonate, ammonia, etc. In addition, antibiotics such as ampicillin, tetracycline or aureobasidin may also be added, as necessary, to the medium during the culture.

Examples of a medium in which a transformed host cell obtained from an animal cell as a host cell is cultured may include an RPM11640 medium [The Journal of the American Medical Association, 199, 519 (1967)], an Eagle's MEM medium [Science, 122, 501 (1952)], a DMEM medium [Virology, 8, 396 (1959)], a 199 medium [Proceeding of the Society for the Biological Medicine, 73, 1 (1950)], all of which are commonly used, or a medium obtained by adding fetal bovine serum or the like to these medium. The culture is generally carried out for 1 to 7 days with conditions such as pH of 6 to 8, a temperature of 30° C. to 40° C., and 5% to 10% $CO_2$. In addition, antibiotics such as kanamycin or penicillin may also be added, as necessary, to the medium during the culture.

As a medium in which a transformed host cell obtained from a plant cell as a host cell is cultured, common mediums such as an MS medium or R2P medium are used depending on plant species. The culture is generally carried out for 1 to 21 days with conditions such as pH of 6 to 8 and a temperature of 15° C. to 35° C. In addition, antibiotics such as kanamycin or hygromycin may also be added, as necessary, to the medium during the culture.

In order to isolate and purify an enzyme protein involved in synthesis of fatty acid having trans-11-, cis-13-conjugated double bonds from the culture product of a transformed host cell, common methods of isolating and purifying protein may be used.

Where the protein of the present invention is expressed in a state dissolved in cells, for example, after completion of the culture, cells are recovered by centrifugal separation, and the obtained cells are suspended in a water type buffer. Thereafter, the cells are disintegrated using an ultrasonic disintegrator, French press, Manton Gaulin homogenizer or Dyno mill, so as to obtain a cell-free extract. A supernatant is obtained by centrifuging the cell-free extract, and then, a purified sample can be obtained from the supernatant by applying, singly or in combination, the following ordinary protein isolation and purification methods: the solvent extraction, the salting-out method using ammonium sulfate, the desalting method, the precipitation method using an organic solvent, the anion exchange chromatography using resins such as diethylaminoethyl (DEAE) sepharose or DIAION HPA-75 (manufactured by Mitsubishi Chemical Corp.), the cation exchange chromatography using resins such as S-Sepharose FF (manufactured by Pharmacia), the hydrophobic chromatography using resins such as butyl sepharose or phenyl sepharose, the gel filtration method using a molecular sieve, the affinity chromatography, the chromatofocusing method, and the electrophoresis such as isoelectric focusing.

Where the above protein is expressed with forming an insoluble form in cells, the cells are recovered and disintegrated in the same manner as described above, and precipitation fractions are then obtained by centrifugal separation. Thereafter, the above protein is recovered from the fractions by common method, and the insoluble form of the protein is solubilized using a protein denaturing agent. The obtained solubilized solution is diluted or dialyzed with a dilute solution, which contains no protein denaturing agents or in which the concentration of a protein denaturing agent is too thin to denature the protein. The protein is thus converted into a normal three-dimensional structure. Thereafter, the same above isolation and purification method is applied to the obtained protein, so as to obtain a purified sample.

Where the protein of the present invention or a derivative thereof such as a sugar-modified derivative is secreted outside the cells, the above protein or a derivative thereof such as a sugar chain added form can be recovered from a culture supernatant. This is to say, the culture is treated by the same above techniques such as centrifugal separation, so as to obtain soluble fractions. Thereafter, a purified sample can be obtained from the soluble fractions by the same above isolation and purification method.

Moreover, the protein of the present invention can be produced by chemical synthesis methods such as the Fmoc method (fluorenylmethyloxycarbonyl method) or the tBoc method (t-butyloxycarbonyl method). Furthermore, the protein of the present invention can also be synthesized using peptide synthesizers that are available from Sowa Trading Co., Inc. (manufactured by Advanced Chem Tech, USA), Perkin Elmer Japan (manufactured by Perkin-Elmer, USA), Pharmacia Biotech (manufactured by Pharmacia Biotech, Sweden), Aloka (manufactured by Protein Technology Instrument, USA), Kurabo Industries Ltd. (manufactured by Synthecell-Vega, USA), Japan PerSeptive Ltd. (manufactured by PerSeptive, USA), or Shimadzu Corporation.

(5) Method for Producing Fatty Acid Having Trans-11-, Cis-13-Conjugated Double Bonds, Using the Gene of the Present Invention, Method for Increasing the Production Amount of Fatty Acid Having Trans-11-, Cis-13-Conjugated Double Bonds, and Method for Producing Seed Oil The present invention relates to a method for producing fatty acid having trans-11-, cis-13-conjugated double bonds from fatty acid having a double bond at position Δ12, by using the above described enzyme protein of the present invention.

Specifically, the present invention relates to a production method by a common synthetic reaction using an enzyme reaction, such as a method for producing fatty acid having trans-11-, cis-13-conjugated double bonds which comprises immobilizing, as necessary, the enzyme protein isolated by the above described method onto a carrier such as polyacrylamide gel or carrageenan gel by common immobilization techniques, and then adding the thus obtained carrier into a solution containing fatty acid having a double bond at position Δ12. It also relates to a method for producing fatty acid having trans-11-, cis-13-conjugated double bonds, wherein the above described transformed host cell of the present invention is cultured and fatty acid having trans-11-, cis-13-conjugated double bonds produced by the transformed host cell is recovered.

As stated above, the transformed host cell having the gene of the present invention produces fatty acid having trans-11-, cis-13-conjugated double bonds in an amount larger than a non-transformed host cell does. Such a transformed host cell is selected, and fatty acid having trans-11-, cis-13-conjugated double bonds produced by the transformant is recovered. Thus, fatty acid having trans-11-, cis-13-conjugated double bonds can be relatively easily obtained in large quantity.

That is to say, the present invention also provides a method for increasing the content of fatty acids having trans-11-, cis-13-conjugated double bonds and/or a derivative thereof in a host cell, which comprises the steps of: (a) transforming a host cell with a gene encoding a protein having an ability of synthesizing fatty acid having trans-11-, cis-13-conjugated double bonds from fatty acid having a double bond at position Δ12; (b) allowing the host cell to grow under appropriate conditions to allow the gene to be expressed; and (c) selecting host cells comprising an increased amount of fatty acids having trans-11-, cis-13-conjugated double bonds and/or derivatives thereof.

The "gene encoding a protein having an ability of synthesizing fatty acid having trans-11-, cis-13-conjugated double bonds from fatty acid having a double bond at position Δ12" in the present specification may include a gene encoding a protein having an amino acid sequence shown in SEQ ID NO: 1 or 12, or amino acid sequence comprising a deletion, addition or substitution of one or several amino acids with respect to the amino acid sequence shown in SEQ NO: 1 or 12, and having an ability of synthesizing fatty acid having trans-11-, cis-13-conjugated double bonds from fatty acid having a double bond at position Δ12. The above gene in the present specification may also include any genes encoding proteins having amino acid sequences other than those as described above, as long as they encode proteins having an ability of synthesizing fatty acid having trans-11-, cis-13-conjugated double bonds from fatty acid having a double bond at position Δ12.

In the present specification, derivatives of fatty acid having trans-11-, cis-13-conjugated double bonds mean those having C chains increased by two or its multiples from the trans-11-, cis-13-conjugated double bonds by elongase. Examples of such a derivative may include cis-11-, trans-13-, cis-15-eicosatrienoic acid which is produced from punicic acid.

A method of recovering fatty acid having trans-11-, cis-13-conjugated double bonds is not particularly limited, and common methods of recovering such fatty acid from a medium can be used.

In the case of a transformed plant for example, the seeds of the transformant of the present invention or the plant body as a whole are ground, or they are compressed, so that oil-soluble components can be extracted.

When the components contain a large amount of oil, the oil is recovered by using a filter press or by centrifugal separation, and the recovered oil may be directly used as a plant oil component, which is added to cosmetics or the like. When the components contain a small amount of oil, or when the oil is used for foods or the like, they are extracted with an organic solvent such as hexane, followed by purification such as degumming, deacidification, decoloring or deodorization.

Otherwise, oil-soluble components containing fatty acids are separated and purified by using column chromatography or the like as necessary, so that only triene fatty acid components of interest are isolated and may be used as medicaments or the like.

That is to say, the present invention further provides a method for producing a seed oil, which comprises the steps of: (a) transforming a plant cell with a gene encoding a protein having an ability of synthesizing fatty acid having trans-11-, cis-13-conjugated double bonds from fatty acid having a double bond at position Δ12; (b) growing a fertile plant from the obtained transformed plant cell; (c) obtaining progeny seeds from the obtained fertile plant, and selecting from the obtained progeny seeds, those comprising an increased amount of fatty acids having trans-11-, cis-13-conjugated double bonds and/or a derivative thereof; and (d) obtaining oil comprising an increased amount of fatty acids having trans-11-, cis-13-conjugated double bonds and/or a derivative thereof from the obtained progeny seeds; and a seed oil produced by the above production method.

(6) Primer Set

A primer set consisting of a combination of a primer having a nucleotide sequence shown in SEQ ID NO: 3 or 4 and a primer having a nucleotide sequence shown in SEQ ID NO: 5, and a primer set consisting of a combination of two primers having nucleotide sequences shown in SEQ ID NOS: 6 and 7, are useful for synthesizing and amplifying the gene of the present invention, and these primers are included in the scope of the present invention.

Similarly, a primer set consisting of a combination of a primer having a nucleotide sequence shown in SEQ ID NO: 14 or 15 and a primer having a nucleotide sequence shown in SEQ ID NO: 16, and a primer set consisting of a combination of a primer having a nucleotide sequence shown in SEQ ID NO: 17 or 19 and a primer having a nucleotide sequence shown in SEQ ID NO: 18 or 20 are also useful for synthesizing and amplifying the gene of the present invention, and these primers are also included in the scope of the present invention.

These primers can be synthesized by common methods using a commercially available DNA synthesizer or the like.

(7) Oligonucleotide

Oligonucleotides selected from a group consisting of a sense oligonucleotide having the same sequence as a sequence corresponding to 5 to 100 contiguous nucleotides in any one of the nucleotide sequences (A) to (E) as described above (1) in the present specification; an antisense oligonucleotide having a sequence complementary to the above sense nucleotide; and an oligonucleotide derivative of the above sense or antisense oligonucleotide, are useful for detecting or amplifying the gene of the present invention, and these oligonucleotides are included in the scope of the present invention. These oligonucleotides can be synthesized by common methods using a DNA synthesizer or the like.

Where these oligonucleotides are used as sense and antisense primers, the used oligonucleotides preferably do not change so much the melting temperature (Tm) and the number of nucleotides of these primers. Moreover, the sequence consists of, generally 5 to 100 nucleotides in length, preferably 10 to 60 nucleotides in length, and more preferably 15 to 50 nucleotides in length.

Derivatives of these oligonucleotides can be used as the oligonucleotides of the present invention. Examples of such oligonucleotide derivatives may include oligonucleotide derivatives wherein the phosphate diester bond has been converted into a phosphorothioate bond, oligonucleotide derivatives wherein the phosphate diester bond has been converted into an N3'-P5' phosphamidate bond, oligonucleotide derivatives wherein the ribose and the phosphate diester bond have been converted into a peptide-nucleic acid bond, oligonucleotide derivatives wherein the uracil has been substituted with a C-5 propynyluracil, oligonucleotide derivatives wherein the uracil has been substituted with a C-5 thiazole uracil, oligonucleotide derivatives wherein the cytosine has been substituted with a C-5 propynylcytosine, oligonucleotide derivatives wherein the cytosine has been substituted with a phenoxazine-modified cytosine, oligonucleotide derivatives wherein the ribose has been substituted with a 2'-O-propyl ribose, and oligonucleotide derivatives wherein the ribose has been substituted with a 2'-methoxyethoxy ribose.

(8) Functional Health Beverage and Food, and Animal Feed

The present invention provides functional health beverage and food containing a seed, seed oil, or a treated product thereof, which is produced using the gene of the present invention, and animal feed containing a seed, seed oil, or a treated product thereof, which is produced using the gene of the present invention.

Seed oil produced using the gene of the present invention is characterized in that it contains an increased amount of fatty acid having trans-11-, cis-13-conjugated double bonds (e.g., punicic acid). It has been known that when humans or animals take in such seed oil, the intaken seed oil brings effects such as reduction in internal fat, reduction of accumulation of internal fat, prevention or improvement of disorder of lipid metabolism, prevention or improvement of disorder of carbohydrate metabolism, or prevention or treatment of cancers in their bodies (Japanese Patent Laid-Open No. 2000-355538).

Accordingly, functional health beverage and food can be produced by using a seed, seed oil or a treated product thereof, which is produced by using the gene of the present invention.

In the present invention, the above seed or seed oil can be directly used, but they may be processed into the form of fatty acid or a derivative thereof. In order to process the above seed or seed oil into fatty acid, a method comprising pretreating the above seed oil as necessary, hydrolyzing it to obtain fatty acid, and purifying the obtained fatty acid is preferably used. Examples of a method of pretreating seed oil may include: physical methods such as a method of leaving seed oil at a temperature higher than the melting point and then settling out and eliminating those with a high specific gravity, or method of eliminating those with a low specific gravity by centrifugal separation; and chemical methods such as a method of adding sulfuric acid or phosphoric acid to raw material fats and oils, stirring the mixture under heating to decompose proteins and organic pigments, and eliminating them by neutralization or washing, or a method of adding activated clay thereto, subjecting the mixture to heat treatment, and then adsorbing and eliminating decomposed products, coloring substances, resin substances, etc. Examples of hydrolysis may include: chemical methods such as a method of saponifying fats and oils with alkali such as potassium hydroxide, a medium pressure catalytic decomposition method of decomposing the above oil under medium pressure using zinc oxide, calcium oxide or magnesium oxide as a catalyst, or a continuous high pressure decomposition method of continuously decomposing the above oil under high pressure; and a biological hydrolysis using lipase or microorganisms. Examples of a method of separating and purifying fatty acid may include: a method of distilling and purifying fatty acid of interest using a batch-type, semicontinuous or continuous distillatory, or a precision distillatory; and a method of cooling a solution or fused product that is in a supersaturated state to a temperature that is suitable for fatty acid of interest, generating crystals, and collecting the generated crystals by the compression method, the Solexol method (U.S. Pat. No. 2,293,674, 1942), the Emersol method (U.S. Pat. No. 2,421,157, 1974), or the Henkel method (W. Stein et al., J. Am. Oil Chem. Soc., 45, 471, 1968).

Functional health beverage and food can be produced, directly from the seed, seed oil or treated product thereof of the present invention, or by mixing them with other substances as appropriate. The content of the seed, seed oil or treated product thereof of the present invention in such functional health beverage and food is not particularly limited, but it is preferably 0.01% to 99% by weight, and more preferably 0.1% to 90% by weight. In addition, various types of carriers and/or additives, which are acceptable as functional health beverage and food, may be appropriately added, as desired.

Examples of such a carrier may include carriers, extenders, diluents, fillers, dispersants, excipients such as glucose or lactose, binders such as hydroxypropylcellulose (HPC) or polyvinylpyrrolidone (PVP), solvents such as water, ethanol or vegetable oil, solubilizers, buffers such as sodium bicarbonate, dissolution promoters, gelatinizers such as sodium CMC, HPMC, agar or gelatin, and suspending agents such as sodium CMC or sodium alginate, but are not limited thereto.

Examples of such an additive may include flavor enhancers for improving edibility or palatability, such as glutamine soda or inosinic acid; aromatics such as vanilla, mint, rosemary, linalool or natural aromatic; vitamins such as vitamin A, vitamin B1, vitamin B2, vitamin B6, vitamin C, vitamin E, pantothenic acid or nicotinic acid; sweeteners such as stevia; organic acids such as citric acid, malic acid, fumaric acid, malonic acid, succinic acid, tartaric acid or lactic acid; coloring agents; moisture preventives; fibers; electrolytes; minerals; nutrients; antioxidants; preservatives; flavoring agents; moistening agents; natural plant extracts such as tea extracts, coffee extracts, cocoa extracts, and fruit extracts from oranges, grapes, apples, peaches, pineapples, pears, plums, cherries, papayas, tomatoes, melons, strawberries or raspberries, but are not limited thereto.

The type of the functional health beverage and food of the present invention is not particularly limited. Examples thereof may include: tea beverages such as coffee, black tea, green tea or oolong tea; fruit and vegetable beverages such as soy milk, green juice, fruit juice or vegetable juice; lactic acid bacteria beverages such as yogurt; milk beverages such as cow milk; carbonated beverages such as cola drink; and various types of sports beverages; as well as bakery products such as breads; boiled rice; noodles; soybean processed food such as bean curd; fish or meat processed food such as sausage or ham; confectionery such as cakes, cookies, steamed bean-jam bun, rice crackers, ice cream, pudding, faded black, candies or chocolates; dairy products such as butter, yogurt or cheese; processed fat and oil products such as margarine or shortening; condiments such as mayonnaise, dressing, soy sauce, bean paste or sauce; alimentary yam paste; and pickles.

The functional health beverage and food of the present invention can be used as beverage or food for health maintenance, health promotion, and physical strength enhancement. More specifically, the functional health beverage and food of the present invention can be used as food for improvement of an obese state or suppression of obesity, reduction in accumulated fat, especially internal fat, suppression of fat accumulation, especially suppression of accumulation of internal fat, improvement of disorder of lipid metabolism such as a tendency of hyperlipidemia or hypercholesterolemia, improvement of disorder of carbohydrate metabolism such as a tendency of diabetes or tendency of glycophilia after eating, improvement of a tendency of hypertension, or suppression of hyperplasia of the endarterium, or it can also be used as therapeutic diet at the time of treating cancers.

Moreover, animal feed can be produced from the seed, seed oil or a treated product thereof of the present invention, directly or by mixing them with flavors or aromatics for improving edibility or palatability, as appropriate. In this case, emulsifiers or stabilizers may also be mixed therewith, so as to maintain a certain level of physical properties. Furthermore, the seed, seed oil or a treated product thereof of the present invention may also be used as a raw material for various types of processed feeds or pet food that are industrially produced. Still further, the seed, seed oil or a treated product thereof of the present invention may be directly spread on animal feeds, and used. The content of the seed, seed oil or a treated product thereof of the present invention in animal feeds is not particularly limited. These are used, for example, within the range between 0.1% and 99.5% by weight, and preferably within the range between 0.5% and 90% by weight based on the total weight of animal feeds, at a solid content conversion.

Animal feeds containing the seed, seed oil or a treated product thereof of the present invention, can be used as feeds for preventing or improving obesity of livestocks or pets, for preventing or treating their diabetes, or for preventing or treating their cancers.

(9) Cis-11-, Trans-13-, Cis-15-Eicosatrienoic Acid

As described later in Example 1, two new peaks (FIG. 2B, arrow and arrow head) were detected in a transformed *Arabidopsis* T2 seed into which the gene of the present invention (TkFac) was introduced. As a result of GC-MS (EI) analysis, it was found that the one peak (FIG. 2B, an arrow head) was methyl ester of 20:3 fatty acid. Since this peak was not found in any of the seeds of non-transformants, it was assumed that 20:3 fatty acid containing a conjugated double bond was produced in the transformant by the expression of TkFac. It is considered that this 20:3 fatty acid was produced as a result of elongation of the chain length of fatty acid by using punicic acid as a substrate,, and that this fatty acid was cis-11-, trans-13-, cis-15-eicosatrienoic acid. In *Arabidopsis*, unsaturated very long chain fatty acid (C20 or greater) is produced from fatty acid having unsaturated C18 by a chain length elongating enzyme. For example, it has been known that a chain length elongating reaction occurs in 18:2 (9c, 12c) by one reaction and that the chain length is extended by two carbon atoms, so as to produce 20:2 (11c, 14c).

Moreover, as described later in Example 2, in transformed yeast into which the gene of the present invention (PgFac) was introduced, a new peak (indicated with arrow heads in FIGS. 6B and 7B) was detected. As a result of GC-MS (EI) analysis, it was found that this peak was methyl ester of 16:3 fatty acid. Since this peak was not found in pYES2 trans-formed yeast (FIGS. 6A and 7A), it was assumed that using 16:2 as a substrate, 16:3 fatty acid containing conjugated double bonds (cis-9-,trans-11-,cis-13-hexadecatrienoic acid) was produced in the yeast by the expression of PgFac.

Furthermore, as described later in Example 2, two new peaks (FIG. 9B, arrow and an arrow head) were detected in a transformed *Arabidopsis* T2 seed into which the gene of the present invention (PgFac) was introduced. As a result of GC-MS (EI) analysis, it was found that the one peak (FIG. 9B, an arrow head) was methyl ester of 20:3 fatty acid. Since this peak was not found in any of the seeds of non-transformants, it was assumed that 20:3 fatty acid containing conjugated double bonds was produced in the transformant by the expression of PgFac. It is considered that using punicic acid as a substrate, this 20:3 fatty acid was generated as a result of elongation of the chain length of fatty acid, and that it was cis-11-, trans-13-, cis-15-eicosatrienoic acid. In *Arabidopsis*, unsaturated very long chain fatty acids (C20 or greater) are produced from fatty acids having unsaturated C18 by a chain length elongating enzyme. For example, it has been known that a chain length elongating reaction occurs in 18:2 (9c, 12c) by one reaction and that the chain length is extended by two carbon atoms, so as to produce 20:2 (11c, 14c).

The present invention will be further specifically described in the following examples, but the present invention is not limited by the examples

EXAMPLES

Example 1

*Trichosanthes kirilowii* Conjugase (1) Isolation of RNA from *Trichosanthes kirilowii*

*Trichosanthes kirilowii* immature seeds that started to accumulate a conjugated triene fatty acid, punicic acid, were collected, and the seeds were used as materials for isolating total RNA. As described in Molecular Cloning, there are various methods of preparing total RNA, including the guanidine hydrochloride method. Of those methods, the phenol-chloroform method (*Arabidopsis* Protocols, Methods in Mol. Biol. 82, p. 85-89 Humana Press) was applied in the present example. That is, approximately 4 g of the immature seeds was added to liquid nitrogen in a mortar, and the mixture was fully crushed and then transferred into 50 ml tubes. 7 ml of an extract solution (0.4 M LiCl, 25 mM EDTA, 1% SDS, 0.2 M Tris buffer solution (pH 9.0)) and 7 ml of phenol saturated with water treated with diethylpyrocarbonate (DEPC) were added to each tube, followed by stirring with Vortex. The obtained mixture was centrifuged at 4° C. at 750 g for 5 minutes. Thereafter, each of the upper layers was transferred into a new 50 ml tube, with caution against suspended matters. 7 ml of phenol saturated with sterilized water was added thereto again, the mixture was fully stirred, and it was then centrifuged in the same manner as described above. The upper layer was transferred into a new tube. An equal amount of chloroform was added thereto and stirred, and the upper layer was recovered by centrifugal separation. This operation was repeated three times in the same manner as described above. A one-tenth amount of 3 M sodium acetate and 2 times amount of 95% ethanol were added to the recovered upper layer, followed by leaving at rest at −80° C. for 30 minutes. Thereafter, the obtained product was subjected to centrifugal separation at 4° C. at 14,000 g for 10 minutes, and 3 ml of 2 M lithium chloride was added to the obtained precipitate. The mixture was fully stirred to dissolve it, and it was then left at rest on ice for 30 minutes or longer, so that RNA was separated from DNA. The RNA was subjected to centrifugal separation at 4° C. at 14,000 g for 10 minutes, and the obtained precipitate was dissolved in 0.8 ml of sterilized water. A one-tenth amount of 3 M sodium acetate and 2 times amount of 95% ethanol were added thereto, and the obtained mixture was left at rest at −80° C. for 5 minutes. Thereafter, the mixture was subjected to centrifugal separation at 4° C. at 14,000 g for 5 minutes, so as to precipitate RNA. The obtained precipitate was washed with 70% ethanol, then centrifuged, and then dried. The dried product was dissolved in 100 µl of sterilized water, so as to obtain an RNA solution.

(2) Synthesis of cDNA

Using RNA as a template, cDNA synthesis is carried out with reverse transcriptase and primers which depend on purposes. In the present example, a first strand cDNA was synthesized by using reverse transcriptase, SuperScript II RNase H⁻ Reverse transcriptase manufactured by Gibco BRL, and oligo dT primers. Subsequently, a second strand cDNA was synthesized using a Marathon cDNA Amplification Kit manufactured by CLONTECH, so as to obtain a double strand cDNA. More specifically, oligo (dT) primer (0.5 µg) binding to a poly A sequence was added to the total RNA (10 µg) that was derived from the *Trichosanthes kirilowii* immature seeds obtained in (1) above and was to be used as a template to synthesize the first strand cDNA, and the obtained mixture was treated at 70° C. for 2 minutes and then cooled on ice. Thereafter, a first-strand buffer (final concentration: 50 mM Tris, 3 mM MgCl$_2$, 75 mM KCl, pH 8.3), a dNTP mixture (final concentration: 0.5mM each), dithiothreitol (final concentration: 10 mM), RNaseOUT Recombinant Ribonuclease Inhibitor (40 units, manufactured by Gibco BRL) were mixed with the above reaction product, and the obtained mixture was incubated at 48° C. for 2 minutes. Thereafter, reverse transcriptase (400 units) was further added thereto, so that the total 20 µl of a reaction solution was prepared, followed by incubation at 48° C. for 1 hour. After the reaction was terminated, the obtained reaction solution was cooled on ice. By this operation, the first strand cDNA was synthesized.

Subsequently, using a kit manufactured by CLONTECH, a second-strand buffer (final concentration: 20 mM Tris, 100 mM KCl, 10 mM ammonium acetate, 5 mM MgCl$_2$, 0.15 mM β-NAD, 0.05 mg/ml bovine serum albumin), a dNTP mixture (final concentration: 0.05 mM each), *E. coli* DNA polymerase I (12 units), *E. coli* RNase H (0.5 units) and sterilized water were added to 10 µl of the above synthesized first strand cDNA solution, so as to prepare the total 40 µl of solution. The obtained solution was blended and kept at 16° C. for 90 minutes. Thereafter, 10 units of T4 DNA Polymerase were added thereto and mixed, and the obtained mixture was further kept at 16° C. for 45 minutes. Thereafter, EDTA (final concentration: 10 mM) and glycogen (final concentration: 0.1 mg/ml) were added thereto to terminate the reaction. Phenol/chloroform/isoamyl alcohol (25:24:1) was added to the reaction solution, and the mixture was stirred and then subjected to centrifugal separation at 7,000 g for 10 minutes to recover a supernatant. Chloroform/isoamyl alcohol (24:1) was added to the obtained supernatant, and the mixture was stirred and then subjected to centrifugal separation under the same conditions as above. The supernatant was recovered, and 1.5 times amount of 4 M ammonium acetate was added thereto. 95% ethanol was further added thereto in an amount of 2.5 times of the mixture, and the thus obtained mixture was well blended. Thereafter, the mixture was centrifuged at 14,000 g for 20 minutes at room temperature, and the obtained precipitate was dissolved in 10 µl of sterilized water, so as to obtain a double stand cDNA solution.

(3) Setting of Primer Region

Homology comparison was performed on amino acid sequences of a Δ12 desaturase gene and other genes, which had been reported until then, so as to search for common sequences. With regard to Δ12 desaturase genes of *Arabidopsis* (accession No. L26296) and *Calendula officinalis* (accession No. AF343065), eleostearic acid-synthesizing conjugase genes of *Momordica charantia* (accession No. AF182521) and *Impatiens balsamica* (accession No. AF182520), and calendic acid-synthesizing conjugase genes of *Calendula officinalis* (accession Nos. AF343064, AF310155 and AF310156), their proteins were aligned to search for highly homologous regions. From among such regions, those which contained a region conserved among these membrane bound desaturase genes and were at maximum approximately 500 bp apart from each other, were selected regardless of the functions of the enzymes. Thereafter, primers were produced by the comparison of amino acid sequences and nucleotide sequences, considering the degeneracy of nucleotides having the nucleotide sequences shown in SEQ ID NOS: 3 to 5.

(4) Isolation of Partial Sequence of Punicic Acid Synthetase (Conjugase) cDNA by RT-PCR 1 µl of a solution obtained by diluting the first strand cDNA solution synthesized in (2) above with a TE buffer to 1/20, 1 µM each of primers shown in SEQ ID NOS: 3 and 5, and 2.5 units of Takara Ex Taq DNA polymerase (Takara Bio Inc.) were added to a PCR reaction solution so as to prepare the total 50 µl of a solution, which was then subjected to a PCR reaction under the following conditions. This is to say, after heating at 94° C. for 1 minute, a cycle consisting of denaturation at 94° C. for 30 seconds, annealing at 52° C. for 1 minute, and elongation at 72° C. for 40 seconds was repeated 30 times, and finally the reaction product was heated at 72° C. for 10 minutes. After completion of the reaction, an aliquot of the reaction solution was subjected to 1% agarose gel electrophoresis, and then stained with ethidium bromide. As a result, a band of the expected size was confirmed. Thus, the reaction solution was deproteinized with 50 µl of phenol/chloroform/isoamyl alcohol (25:24:1), and the upper layer was transferred into a new tube. 5 µl of a 3 M sodium acetate solution (pH 5.2) and 125 µl of ethanol were added thereto, and the mixture was left at rest at −80° C. for 15 minutes, and then subjected to centrifugal separation at 14,000 g for 10 minutes, so as to obtain a precipitate containing DNA fragments. This precipitate was dissolved in 10 µl of sterilized water, and the product was subjected to 0.8% agarose gel electrophoresis and then stained with ethidium bromide. Thereafter, a band of a size of interest was cut out of the gel, and a solution containing amplified fragments was recovered using SUPREC-01 (manufactured by Takara Bio Inc.), followed by ethanol precipitation. Thereafter, the purified DNA fragments were dissolved in 10 µl of sterilized water. 4.5 µl from the obtained solution was mixed with 0.5 µl (25 ng) of a plasmid vector pGEM-T Easy (manufactured by Promega), and the obtained mixture was then subjected to a ligation reaction at 16° C. overnight, using a DNA ligation kit (manufactured by Takara Bio Inc.) Using 2 µl from the reaction solution, *Escherichia coli* (DH5α) was transformed by Hanahan's method (DNA cloning, vol. 1, pp. 109-136 (1985)), so as to obtain white colonies that were formed on an LB medium containing ampicillin (50 µg/ml) and X-gal.

(5) Screening of cDNA Clone 8 clones were randomly picked up from the clones obtained in (4) above. A portion was scraped off from each colony, and the portion was added to 20 µL of a PCR reaction solution containing 1 µM each of the primers shown in SEQ ID NOS:

4 and 5, followed by performing a PCR reaction under the same conditions as in (4) above. After completion of the reaction, an aliquot of the reaction solution was subjected to 1% agarose gel electrophoresis, and then stained with ethidium bromide. As a result, a band of the expected size was confirmed. Thus, plasmid DNA was prepared from these clones, and the sequences of cDNA inserted therein were analyzed using SP6 primers (ABI Prism BigDye Terminator Cycle Sequencing Ready Reaction Kit, ABI Prism 310 Genetic Analyzer: manufactured by PE Applied Biosystems). The obtained nucleotide sequences were translated into amino acid sequences, using GENETYX (manufactured by Software Development), and the obtained sequences were compared with one another. As a result, the 8 clones were classified into 2 types of cDNA, and it was determined that the one type is highly likely to be a partial sequence of a *Trichosanthes kirilowii* conjugase gene. Thus, based on this information, primers specific for the cDNA sequences shown in SEQ ID NOS: 8 to 11 were synthesized, and clones containing 5' and 3' regions of the cDNA sequences were obtained according to the method mentioned below.

(6) Isolation of *Trichosanthes kirilowii* Conjugase Gene by 5' and 3' RACE Method 5 µl of the double strand cDNA solution prepared in (2) above was reacted at 16° C. overnight in a ligation buffer (final concentration: 50 mM Tris-HCl, 10 mM $MgCl_2$, 1 mM DTT, 1 mM ATP, 5% polyethylene glycol, pH7.8) containing 400 units of T4 DNA ligase, using a Marathon cDNA Amplification Kit manufactured by CLONTECH, so that adaptors were bound to the both ends of the double strand cDNA. The reaction solution was diluted with a dilution buffer (10 mM Tricine-KOH, 0.1 mM EDTA, pH8.5) to 1/50 to 1/250. The thus diluted solution was used as a template. With regard to 5' RACE, using API that is a primer to the adaptor and a primer shown in SEQ ID NO: 8, the same PCR reaction solution as in (4) above was prepared, and a PCR reaction was carried out under the following conditions. That is, after heating at 94° C. for 1 minute, a cycle consisting of denaturation at 94° C. for 30 seconds, annealing at 55° C. for 1 minute, and elongation at 72° C. for 1 minute was repeated 30 times, and finally the reaction product was heated at 72° C. for 10 minutes. With regard to 3' RACE, using the API and a primer shown in SEQ ID NO: 10, the same PCR reaction solution as in (4) above was prepared, and a PCR reaction was carried out under the following conditions. That is, after heating at 94° C. for 1 minute, a cycle consisting of denaturation at 94° C. for 30 seconds, annealing at 55° C. for 1 minute, and elongation at 72° C. for 1.5 minutes was repeated 30 times, and finally the reaction product was heated at 72° C. for 10 minutes. When an aliquot of each of the reaction solutions was subjected to 1% agarose gel electrophoresis, a single band was detected in each aliquot. In order to confirm whether these bands contained the cDNA, 1 µl was taken out of each of the reaction products of 5' and 3' RACE, and it was subjected to nested PCR This is to say, with regard to 5' RACE, using AP2 that is a primer to the adaptor and a primer shown in SEQ ID NO: 9, PCR was carried out under the same above conditions. With regard to 3' RACE, using the AP2 and a primer shown in SEQ ID NO: 11, PCR was carried out under the same above conditions. After completion of the reactions, an aliquot was taken out of each of the reaction products, and it was subjected to agarose gel electrophoresis. As a result, a single band of the expected size was detected in each aliquot. These bands were cut out of the agarose gel, and DNA fragments were purified by the same method as in (4) above. The fragments were ligated to pGEM-T Easy, and DH5α was transformed therewith, so as to obtain white colonies that were formed on an LB medium containing ampicillin (50 µg/ml) and X-gal.

8 clones each were randomly picked up from the clones obtained in (6) above. A portion was scraped off from each colony, and it was then added to 20 µl of a PCR reaction solution, followed by performing a PCR reaction under the same conditions as for nested PCR in (6) above. After completion of the reaction, an aliquot of the reaction solution was subjected to 1% agarose gel electrophoresis, and then stained with ethidium bromide. 4 clones each were selected from clones in which a band of the expected size was confirmed, and plasmid DNA was prepared from these clones. Thereafter, the cDNA inserted into the plasmid was sequenced using T7 and SP6 primers. The obtained nucleotide sequences were translated into amino acid sequences, using GENETYX (manufactured by Software Development), and the obtained sequences were compared with one another. As a result, it was confirmed that all the nucleotide sequences contained the partial sequence of the 5'- or 3'-end of the cDNA.

(7) Isolation of Full-Length cDNA of *Trichosanthes kirilowii* Conjugase

Based on the information on the nucleotide sequences of the 5'- and 3'-ends regions of the conjugase cDNA obtained in (6) above, primers were prepared to isolate the full-length cDNA of *Trichosanthes kirilowii* conjugase. That is, a 5' primer was obtained by adding a BamHI site to the 5' side of 22 nucleotides containing a translation initiation codon ATG of the *Trichosanthes kirilowii* conjugase shown in SEQ ID NO: 6. On the other hand, a 3' primer was obtained by adding a SacI site to the 5' side of a sequence complementary to 5 to 27 nucleotides downstream of a translation termination codon TGA of the conjugase gene shown in SEQ ID NO: 7. The double strand cDNA solution prepared in (2) above was diluted with a TE buffer to 1/30. Using 2.5 or 5 µl of the diluted solution and 1 µM each of the above primers, the total 4 samples, each of which consisted of 50 µl of a PCR reaction solution containing 5 units of Pyrobest DNA polymerase (manufactured by Takara Bio Inc.), were prepared. Using these samples, PCR was carried out under the following conditions. That is, after heating at 94° C. for 1 minute, a cycle consisting of denaturation at 94° C. for 30 seconds, annealing at 55° C. for 1 minute, and elongation at 72° C. for 2.5 minutes was repeated 25 times, and finally the reaction product was heated at 72° C. for 10 minutes. 5 units of Takara Ex Taq was further added to the reaction product, followed by heating at 72° C. for 10 minutes. An aliquot of the reaction solution was subjected to 1% agarose gel electrophoresis, and then stained with ethidium bromide. As a result, a band of the expected size was confirmed in all of the 4 samples. Thus, the amplified DNA fragments were purified by the same method as in (4) above. Each of the fragments was then ligated to pGEM-T Easy, and DH5α was transformed therewith, so as to obtain white colonies that were formed on an LB medium containing ampicillin (50 µg/ml) and X-gal.

4 clones each were randomly picked up from the obtained clones. A portion was scraped off from each colony, and it was then added to 20 µl of a PCR reaction solution, followed by performing a PCR reaction under the same conditions as in (7) above. After completion of the reaction, an aliquot of the reaction solution was subjected to 1% agarose gel electrophoresis, and then stained with ethidium bromide. 2 clones each were selected from the clones, in which a band of the expected size was confirmed, and plasmid DNA was prepared from these clones. Thereafter, the cDNA inserted into the plasmid was sequenced using gene specific primers. The obtained nucleotide sequences were translated into amino acid sequences, using GENETYX (manufactured by Software Development), and the obtained sequences were compared with one another. As a result, it was confirmed that all the nucleotide sequences contained the full length of the cDNA.

(8) Structural Analysis of *Trichosanthes kirilowii* Conjugase cDNA

The isolated *Trichosanthes kirilowii* conjugase (TkFac) cDNA was 1,287 bp and it encoded 387 amino acids. The amino acid sequence encoded by the isolated conjugase cDNA is shown in SEQ ID NO: 1, and its nucleotide sequence is shown in SEQ ID NO: 2.

It was confirmed by homology comparison with database that the *Trichosanthes kirilowii* conjugase cDNA had 80% homology with *Momordica charantia* conjugase cDNA, 63% homology with Impatiens balsamica conjugase cDNA, and 57% homology with *Calendula officinalis* conjugase cDNA, among genes whose functions had been analyzed. When the amino acid sequence of TkFac was compared with the existing conjugases, it was found that the amino acid sequence had 75% homology with *Momordica charantia,* 58% homology with *Impatiens balsamica,* and 47% homology with *Calendula officinalis,* and that it contained a region conserved among these existing conjugases. Accordingly, it was assumed that this gene was a conjugase.

(9) Construction of Yeast Protein Expression Shuttle Vector Containing *Trichosanthes kirilowii* Conjugase cDNA The plasmid DNA containing the *Trichosanthes kirilowii* conjugase full-length cDNA obtained in (7) above was cleaved with restriction enzymes BamHI and SacI. The obtained cDNA fragment was purified by the same method as in (4) above and then ligated to a plasmid vector pGEM-3Z, and DH5α was transformed therewith, so as to obtain white colonies that were formed on an LB medium containing ampicillin (50 μg/ml) and X-gal. Plasmid DNA was extracted from the transformants, and those containing the cDNA were selected and cleaved with restriction enzymes BamHI and EcoRI. A fragment containing the cDNA was purified by the same above method, and it was then ligated to the BamHI-EcoRI site of a protein expression shuttle vector pYES2 (manufactured by Invitrogen). DH5α was transformed with the vector, so as to obtain colonies formed on an LB medium containing ampicillin (50 μg/ml). Plasmid DNA was extracted from these transformants, and those containing the cDNA (pYES2/TkFac) were selected, which was then used in the following transformation of yeast.

(10) Preparation of Transformed Yeast

Using *Saccharomyces cerevisiae* D452-2 and INVSc-1, yeast competent cells were prepared using S.c. EasyComp Transformation Kit (manufactured by Invitrogen), and they were then transformed. This is to say, yeast was streaked onto a YPD agar medium (1% yeast extract, 2% peptone, 2% D-glucose, 2% agar) and cultured at 28° C. for 2 days, so as to obtain colonies. A single colony was transferred into 10 ml of a YPD medium (1% yeast extract, 2% peptone, 2% D-glucose) and then subjected to shake culture at 28° C. overnight. Thereafter, the culture solution was diluted with a YPD medium, so as to prepare 10 ml of a culture solution having $OD_{600}$ of 0.2 to 0.4. The obtained culture solution was further subjected to shake culture at 28° C. until $OD_{600}$ became 0.6 to 1.0. Thereafter, the solution was centrifuged at 500 g for 5 minutes at room temperature to recover cells, and the cells were suspended in 10 ml of washing solution. The suspension was centrifuged again under the same above conditions to recover cells. 1 ml of a lithium solution was added thereto, and the cells were suspended, and the suspension was divided into 50 μl each, which was then stored at −80° C.

50 μl of the yeast competent cells was melted at room temperature. 1 μg of pYES2 or the plasmid DNA (pYES2/TkFac) containing *Trichosanthes kirilowii* conjugase full-length cDNA obtained in (9) above was added thereto, and the mixture was blended. 500 μl of a transformation solution was added thereto, and the mixture was well blended. The mixture was incubated at 30° C. for 1 hour while stirring every 15 minutes. Thereafter, 1 ml of a YPD medium was added thereto, and the mixture was subjected to shake culture at 30° C. for 1 hour and then centrifuged at room temperature at 3,000 g for 5 minutes, so as to recover cells. The cells were suspended in 250 μl of an SC minimal medium (−Ura/2% glucose), and the suspension was dispersed on the same agar medium, followed by culture at 30° C. for 3 or 4 days. The 6 grown colonies were selected, and a portion of them was transferred into 3 ml of an SC minimal medium (−Ura/2% glucose), followed by culture at 28° C. overnight. Thereafter, sterilized glycerol (final concentration: 15%) was added to the culture, and the mixture was well blended and stored at −80° C. At the same time, an aliquot of the culture solution was dispersed on an SC minimal medium (−Ura/2% glucose), followed by culture at 30° C. for 2 days. Thereafter, a portion of the obtained colonies was taken, and the portion was added to 20 μl of a PCR reaction solution containing 1 μM each of primers shown in SEQ ID NOS: 6 and 7, and PCR was carried out under the same conditions as in (7) above. As a result, it was confirmed that all of the colonies obtained by transformation with pYES2/TkFac were transformants containing *Trichosanthes kirilowii* conjugase cDNA.

(11) Analysis of Fatty Acid in Yeast Transformant

The yeast transformant prepared in (10) above was transferred into 3 ml of an SC minimal medium (−Ura/2% glucose), followed by culture at 28° C. overnight. Cells recovered by centrifugal separation were washed with sterilized water, and were then suspended in an SC-Gal minimal medium (−Ura/2% galactose). The suspension was then added to 50 ml of an SC-Gal minimal medium (−Ura/2% galactose) containing 0.1% (W/V) Tergitol type NP-40 (Sigma) and 0.3 mM linoleic acid, such that $OD_{600}$ became 0.2. The mixture was subjected to shake culture at 20° C. at 200 rpm for 3 days, and it was further cultured at 15° C. for 3 days. The yeast culture solution as a whole was transferred into a glass tube, and it was centrifuged at 1,700 g for 5 minutes to precipitate yeast. Then, 40 ml of 1% (W/V) Tergitol type NP-40 (Sigma) was added thereto, and the mixture was suspended by Vortex. The suspension was centrifuged at 2,000 g for 10 minutes, so that yeast was precipitated again and washed. The obtained precipitate was washed with Tergitol again, and then washed with 40 ml of sterilized water 3 times in the same manner as above. 25 ml of sterilized water was added to the washed precipitate, and the mixture was suspended by Vortex. 5 ml each of the suspension was poured into a glass tube, and it was then centrifuged at 2,000 g for 10 minutes, so as to obtain a precipitate again. The obtained precipitate was frozen at −80° C., and then freeze-dried for 4 hours. Thereafter, 1 ml of 0.5 M sodium methoxide/methanol was added to each glass tube (5 ml in total), and a methylation reaction was carried out at 50° C. for 1 hour. In some cases, during the methylation reaction, 50 nmol of pentadecanoic acid ($C_{15:0}$) methyl was added to the sample. The reaction solution was returned to room temperature, and thereafter, 7.5 ml 0.9 M NaCl and 5 ml of hexane were added thereto and suspended. The obtained mixture was centrifuged at 1,700 g for 5 minutes, and the obtained supernatant was then subjected to vacuum drying. Thereafter, 20 µl of hexane was added to and dissolved in fatty acid methyl ester extracted by the above operation, and 1 µl of the mixed solution was analyzed by gas chromatography (GC) using GC18A (Shimadzu). For this analysis, using a capillary column (GL Science) with TC-70, 60 m×0.25 mm and a 0.25 µm ID, the temperature was raised from 150° C. to 240° C. at a speed of 3° C./min, and then an isothermal analysis was carried out at 240° C. for 6 minutes.

When fatty acid composition was compared between pYES2 and pYES2TkFac transformed yeasts by GC analysis (FIGS. 1A and B), a new peak was detected in the pYES2/TkFac transformed yeast (FIG. 1B, arrow). In order to examine whether this peak was derived from punicic acid, fatty acid of *Trichosanthes kirilowii* immature seeds accumulating punicic acid was subjected to GC analysis for comparison. Hard hulls were removed from three *Trichosanthes kirilowii* immature seeds. The remained seed portions were completely ground with a pestle in a mortar that was cooled on ice, and 1 ml of 0.5 M sodium methoxide/methanol was added thereto. The mixture was stirred and suspended with a pestle, and then transferred into a glass tube. This was subjected to a methylation reaction at 50° C. for 1 hour, and thereafter, 1.5 ml of 0.9 M NaCl and 1 ml of hexane were added to the reaction product, followed by stirring and extraction. The extract was centrifuged at 2,000 g for 5 minutes, and the obtained supernatant was subjected to vacuum drying. To the thus extracted fatty acid methyl esters, 20 µl of hexane was added and dissolved. 1 µl of the obtained solution was subjected to GC analysis in the same manner as described above, so as to examine the detection time of punicic acid methyl ester (FIG. 1c, arrow). As a result, the above detection time matched the detection time of a peak (FIG. 1B, arrow) that was newly detected in the pYES2TkFac transformed yeast. Moreover, when a mixture of the *Trichosanthes kirilowii*-derived fatty acid GC sample and the above yeast-derived fatty acid GC sample was subjected to GC analysis, the peak of punicic acid methyl ester contained in *Trichosanthes kirilowii* and the new peak of the yeast were detected at the same time. Furthermore, the peak indicated with the arrow in FIG. 1B was subjected to GC-MS (EI) analysis in EI mode, using an Agilent 6890 Series gas chromatograph, a JEOL JMS-600H Msroute mass spectrometer, and the above-described column. From the results that an M+ ion peak appeared at m/z=292, and that the above peak was similar to the spectrum of a 18:3 (9c, 12c, 15c) methyl ester sample analyzed in the same manner, in terms of appeared peak and intensity ratio, it was found that the above peak was 18:3 fatty acid methyl ester. From these results, it was shown that punicic acid was produced in yeast in which *Trichosanthes kirilowii*-derived conjugase TkFac was expressed, and accordingly it became clear that TkFac was a conjugase involved in synthesis of punicic acid. The peaks indicated with the values in FIG. 1 show 16:0 (palmitic acid), 16:1 (9c) (palmitoleic acid), 18:0 (stearic acid), 18:1 (9c) (oleic acid), 18:2 (9c, 12c) (linoleic acid), and 18:3 (9c, 11t, 13c) (punicic acid). The first value represents the number of carbon atoms, the second value represents the number of unsaturated bonds, the value immediately after the number of unsaturated bonds in the parenthesis represents the position of the unsaturated bond, and c and t represent cis and trans, respectively.

From the above results, it became clear that the conjugase gene obtained in (6) above is a gene encoding a protein having an ability of synthesizing fatty acid having trans-11-, cis-13-conjugated double bonds from fatty acid having a double bond at position Δ12.

(12) Construction of Plant Transformation Vector Containing *Trichosanthes kirilowii* Conjugase cDNA The plasmid DNA containing the *Trichosanthes kirilowii* conjugase full-length cDNA obtained in (7) above was cleaved with restriction enzymes BamHI and SacI. The obtained DNA fragment was purified by the same method as in (4) above. The DNA fragment was then ligated to the BamHI-SacI site of a plasmid vector pGEM-3Z, and DH5α was transformed therewith, so as to obtain white colonies that were formed on an LB medium containing ampicillin (50 µg/ml). Plasmid DNA containing the cDNA was extracted from the colonies, and it was then cleaved with restriction enzymes XbaI and SacI. The XbaI-SacI fragment containing the cDNA was purified by the same above method. At the same time, a binary vector pLAN421 [Plant Cell Reports, 10, 286-290 (1991)] was cleaved with restriction enzymes XbaI and SacI, so as to prepare a plasmid fragment of approximately 15 kb that did not contain a β-glucuronidase (GUS) gene of 1.8 kb by the same method as in (4) above. This fragment was ligated to the above XbaI-SacI fragment containing the cDNA, so as to prepare a binary vector pKS-TkFac, in which the cDNA was inserted between a cauliflower mosaic virus (CaMV) 35S promoter sequence and an *Agrobacterium* nopaline synthase gene terminator sequence. Moreover, a binary vector [Plant Molecular Biology, 26, 1115-1124 (1994)] in which a Napin gene promoter sequence [The Journal of Biological Chemistry, 262, 12196-12201 (1987)] was ligated to the GUS gene of pLAN421, was cleaved with restriction enzymes XbaI and SacI, and a plasmid fragment that did not contain the GUS gene as described above was ligated to the above-described cDNA fragment, so as to prepare a binary vector pKN-TkFac, in which the cDNA was inserted between a Napin promoter sequence and an Agrobacterium nopaline synthase gene terminator sequence. DH5α was transformed with these plasmids, so as to obtain colonies formed on an LB medium containing spectinomycin (50 µg/ml) and tetracycline (12.5 µg/ml). pKN-TkFac and pKS-TkFac plasmids DNAs were purified from the colonies, and using these, *Agrobacterium* EHA101 was transformed by the electroporation method, so as to obtain colonies that were formed on a YEB agar medium (0.5% Peptone, 0.5% Beef extract, 0.1% Yeast extract, 0.5% sucrose, 1.5% agarose) containing spectinomycin (50 µg/ml), tetracycline (2.5 µg/ml), chloramphenicol (25 µg/ml) and kanamycin (50 µg/ml). A portion was scraped off from the colonies, and the portion was added to 20 µL of a PCR reaction solution containing and 1 µM each of the primers shown in SEQ ID NOS: 6 and 7, followed by performing a PCR reaction under the same conditions as in (7) above. The reaction product was subjected to electrophoresis, and as a result, a band of the expected size was observed. From these results, it was confirmed that the obtained colonies were *Agrobacterium* transformants containing pKN-TkFac or pKS-TkFac.

(13) Production of *Arabidopsis* Transformant

Transformation of *Arabidopsis* (*Arabidopsis thariana* ecotype Columbia) was carried out by the vacuum infiltration method applied onto its flower bud. This is to say, an *Agrobacterium* transformant containing pKN-TkFac or pKS-TkFac as described in (12) was grown in a YEB medium (0.5% Peptone, 0.5% Beef extract, 0.1% Yeast extract, 0.5% sucrose). Cells were collected by centrifugal separation at 4,000 g for 15 minutes, and they were then resuspended in an infiltration medium (1/2 MS-B5, 5% sucrose, 0.05% MES, 0.044 µM BAP, 0.08% Silwet L-77). *Arabidopsis* with a rachis approximately 2 to 10 cm long was infiltrated in this suspension under reduced pressure (5 to 10 cmHg) for approximately 15 minutes. Thereafter, the *Arabidopsis* was grown and fructified in an incubator as usual, and the seeds were collected. The thus obtained seeds (T1) were sterilized and then were inoculated in a medium containing kanamycin (30 µg/ml) as a selective marker, followed by selection.

(14) Analysis of Fatty Acid of *Arabidopsis* Transformant

Self-pollinated seeds (T2) attached to the selected T1 individual were pooled, and fatty acids were extracted therefrom. The obtained fatty acids were subjected to GC analysis. This is to say, approximately 2 mg of the seeds was subjected to a methylation reaction at 50° C. for 1 hour in 1 ml of a 0.5 M sodium methoxide/methanol solution. Thereafter, 1.5 ml of 0.9% NaCl and 1 ml of hexane were added to the reaction solution followed by shaking for 1 minute, and then the mixture was centrifuged at 1,000 g for 5 minutes. The obtained hexane layer was transferred into a new test tube, followed by vacuum drying. The extract was dissolved in 20 µl of hexane, and 1 µl of the solution was then subjected to lipid analysis by GC. For this analysis, using GC-18A (Shimadzu) and a capillary column (GL Science) with TC-70, 60 m×0.25 mm and ID of 0.25 µm, the temperature was raised from 150° C. to 240° C. at a speed of 3° C./min, and then an isothermal analysis was carried out at 240° C. for 6 minutes. When fatty acid composition was compared between a non-transformed *Arabidopsis* seed (FIG. 2A) and the transformed *Arabidopsis* T2 seed (FIG. 2B) by GC analysis, two new peaks were detected in the transformed T2 seed (FIG. 2B, arrow and tip). The one peak (FIG. 2B, arrow) was detected at the same time when the peak (FIG. 2C, arrow) of punicic acid methyl ester contained in the *Trichosanthes kirilowii* seed fatty acid GC sample was detected. In order to confirm that this peak was not derived from other conjugated linoleic acids such as α-eleostearic acid or calendic acid, but was derived from punicic acid, their methyl esters were separated by gas chromatography, and these were then compared with the fatty acid methyl ester sample extracted from *Arabidopsis* (FIG. 3). That is, from each of *Trichosanthes kirilowii* seeds accumulating punicic acid, *Momordica charantia* seeds accumulating α-eleostearic acid, and *Calendula officinalis* seeds accumulating calendic acid, fatty acid methyl esters were prepared by the method described in (11) above. Subsequently, the obtained fatty acid methyl esters were mixed at an appropriate amount ratio to prepare a sample. The obtained sample was then subjected to GC analysis (FIG. 3A). For the analysis, using the same above device and column, the temperature was raised from 150° C. to 210° C. at a speed of 3° C./min, the temperature was kept at 210° C. for 13 minutes, and the temperature was then raised to 240° C. at a speed of 10° C./min. At the same time, the GC sample prepared from *Arabidopsis* seeds expressing TkFac was analyzed under the above conditions (FIG. 3B). As a result, the detection time of a new peak (FIG. 3B, arrow) detected in the transformed *Arabidopsis* seeds matched that of a punicic acid-derived peak shown in FIG. 3A. This peak was subjected to GC-MS (EI) analysis by the method described in (11) above. From the results that an M+ ion peak appeared at m/z=292, and that the above peak was similar to the spectrum of a 18:3 (9c, 12c, 15c) methyl ester sample analyzed in the same manner, in terms of appeared peak and intensity ratio, it was concluded that the above peak was 18:3 fatty acid methyl ester. From these results, it was shown that punicic acid was produced in *Arabidopsis* seeds expressing TkFac. On the other hand, the other peak (FIGS. 2B and 3B, tip) was also subjected to GC-MS (EI) analysis in the same above manner. From the results that an M+ ion peak appeared at m/z=320, and that the above peak was similar to the spectrums of the 20:3 (5c, 8c, 11c), 20:3 (7c, 10c, 13c), 20:3 (8c, 11c, 14c) and 20:3 (11c, 14c, 17c) methyl ester samples analyzed in the same manner, in terms of appeared peak and intensity ratio, it was concluded that the above peak was 20:3 fatty acid methyl ester (FIG. 4). Since this new peak was not found in any of the non-transformant seeds, it was assumed that 20:3 fatty acid containing a conjugated double bond was produced in the transformant seeds by the expression of TkFac. It was considered that 20:2 (11c, 14c) existing in *Arabidopsis* seeds was unlikely to be a substrate of TkFac. Accordingly, it was considered that 20:3 fatty acid newly produced in *Arabidopsis* seeds expressing TkFac was highly likely to be 20:3 (11c, 13t, 15c) (cis-11, trans-13, cis-15-eicosatrienoic acid) that was produced as a result of the elongation of the chain length of punicic acid produced by TkFac, with the activity of a chain length-elongating enzyme existing in *Arabidopsis* seeds.

6 individuals of each of non-transformants, pKS-TkFac transformants and pKN-TkFac transformants were compared in terms of fatty acid composition of the seeds (Table 1). In pKS-TkFac, punicic acid was accumulated at a ratio of 0.4% on average and 1.2% at maximum. On the other hand, in pKN-TkFac, punicic acid was accumulated at a ratio of 3.5% on average and 10.2% at maximum.

Figure 2:
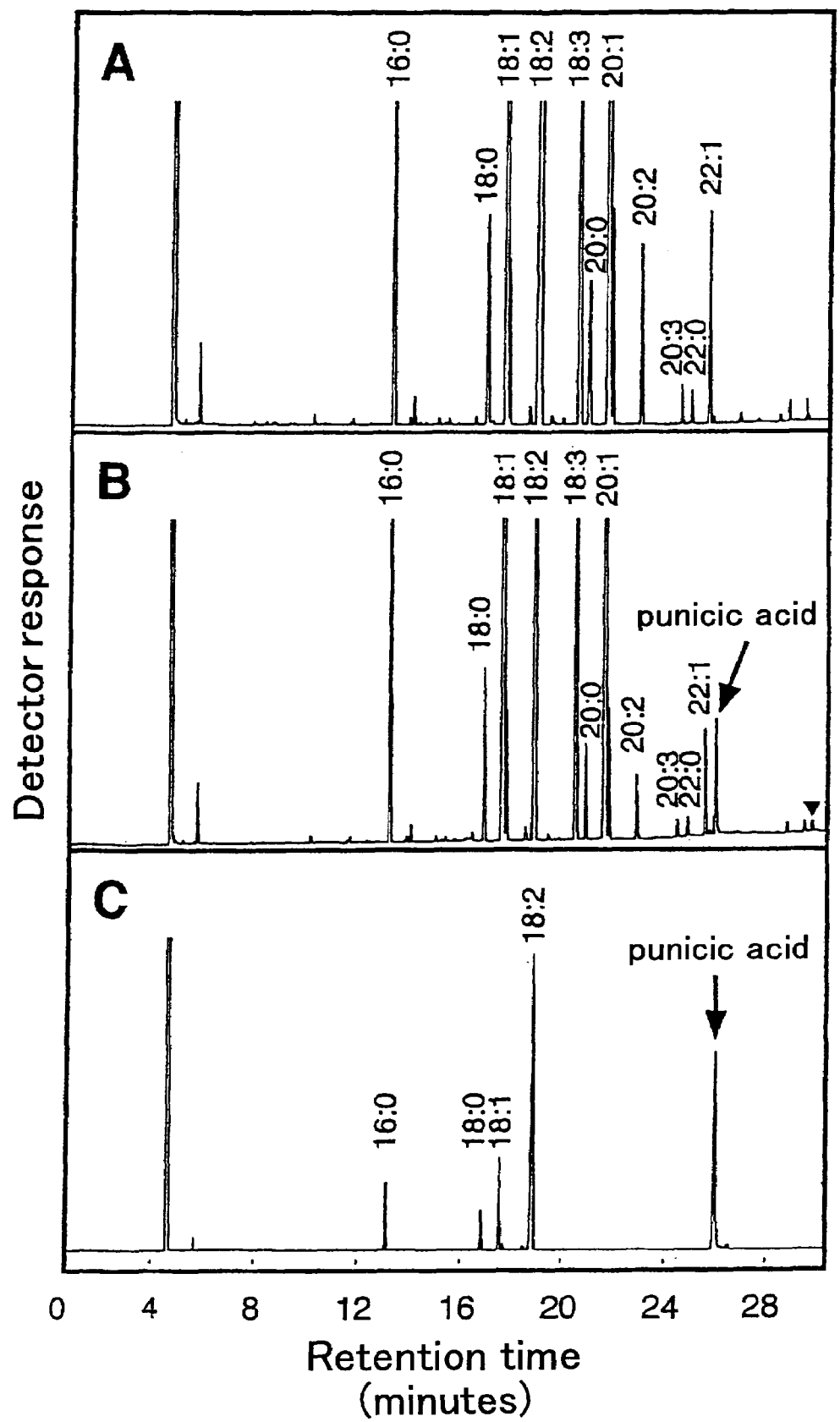
FIG. 2 shows results obtained by GC analyses of fatty acid methyl esters prepared from each of seeds (A) of non-transformed *Arabidopsis,* seeds (B) of *Arabidopsis* transformed with pKN/TkFac, and immature seeds (C) of *Trichosanthes kirilowii*.
Figure 3:
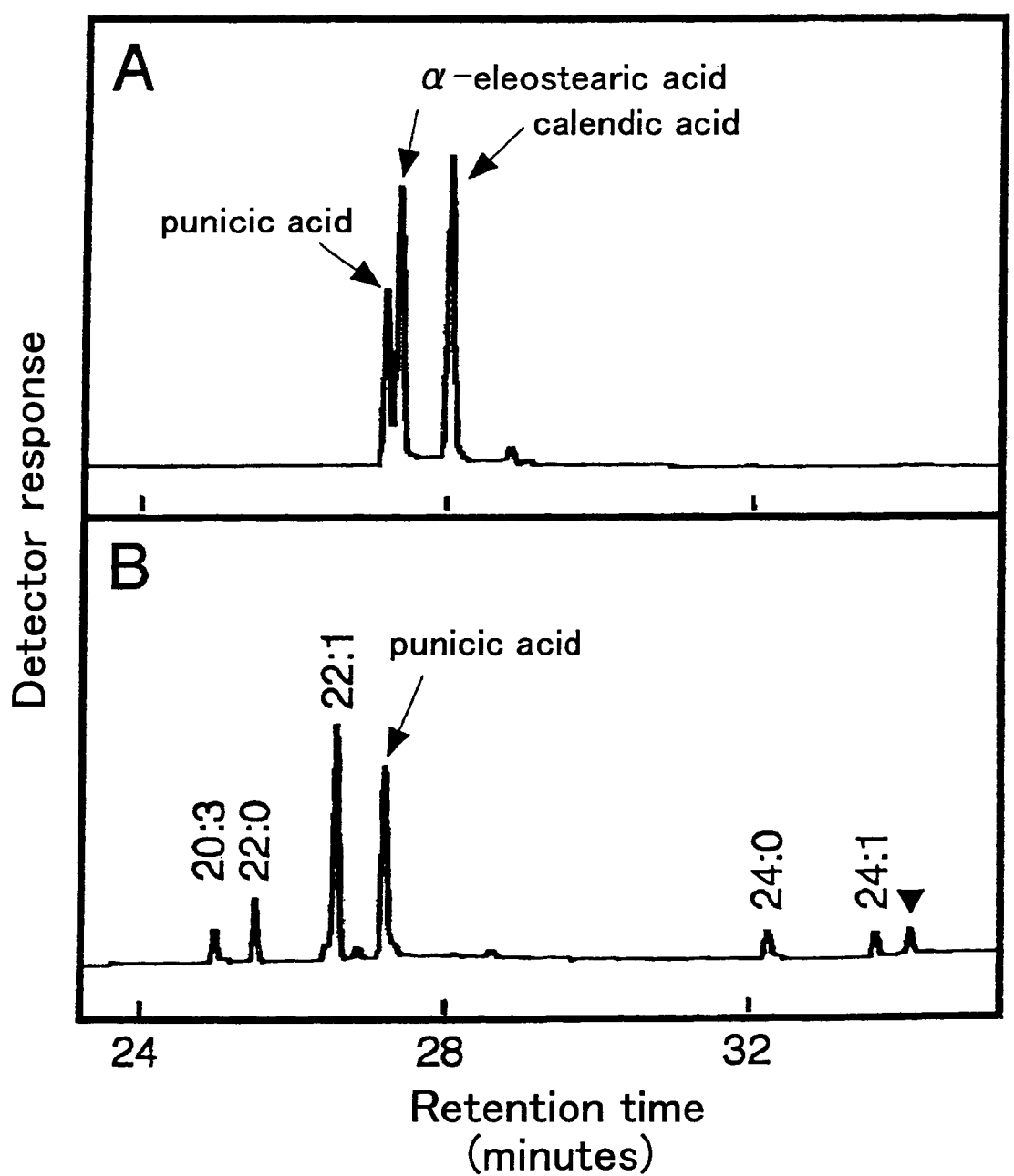
FIG. 3 shows results obtained by GC analyses of a mixture (A) of fatty acid methyl esters samples prepared from seeds of *Trichosanthes kirilowii, Momordica charantia* and *Calendula officinalis,* which contain punicic acid, α-eleostearic acid and calendic acid, respectively, and fatty acid methyl esters (B) prepared from seeds of *Arabidopsis* transformed with pKN/TkFac.
Figure 4:
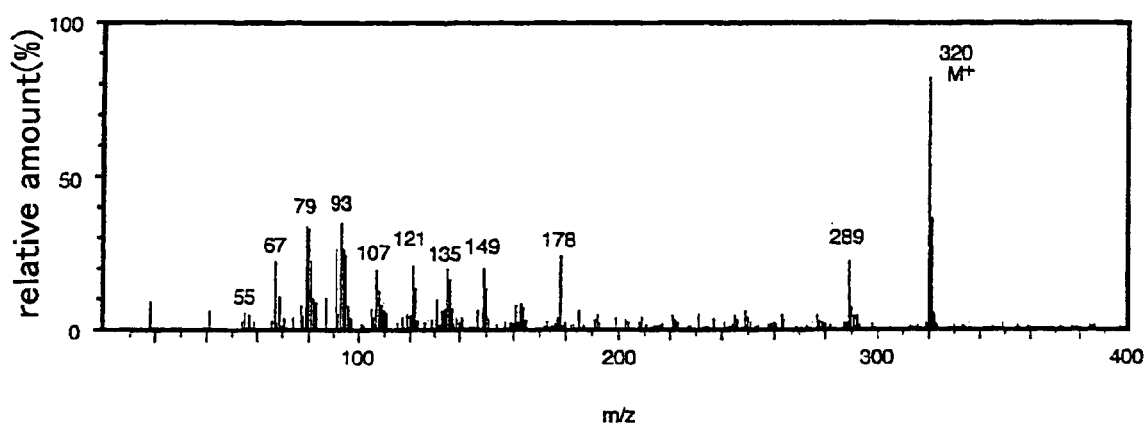
FIG. 4 shows results obtained by comparing a mass spectrum (A) obtained by GC-MS (EI) analysis of the peak indicated with an arrow head in FIG. 4B, with a mass spectrum (B) of 20:3 (7,10,13-eicosatrienoic acid) methyl ester analyzed in the same manner.
Figure 4:
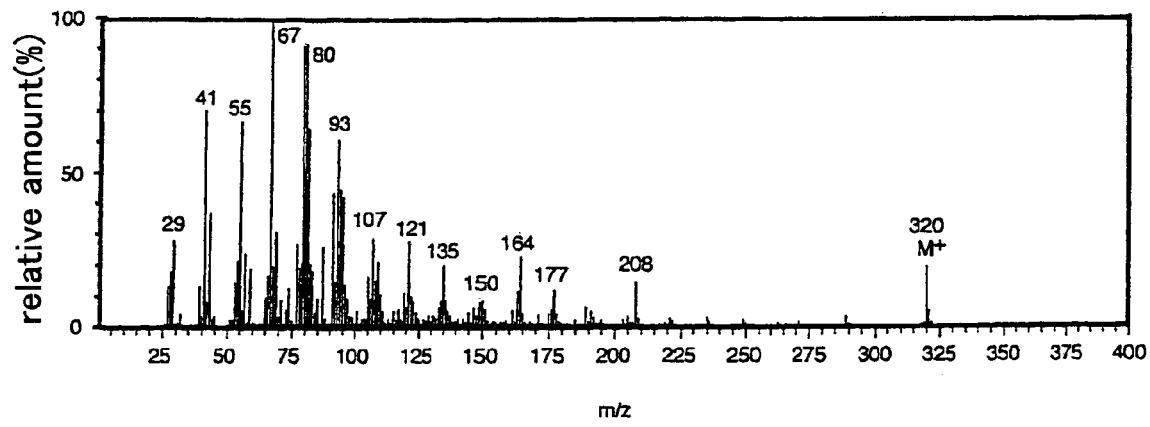

The peaks indicated with the values in FIGS. 2 and 3 show various fatty acid methyl esters, and they specifically represent 16:0 (palmitic acid), 18:0 (stearic acid), 18:1 (9c) (oleic acid), 18:2 (9c, 12c) (linoleic acid), 18:3 (9c, 12c, 15c) (α-linolenic acid), 20:0 (arachidic acid), 20:1 (11c) (gondoic acid), 20:2 (11c, 14c) (11,14-eicosadienoic acid), 20:3 (11c, 14c, 17c) (11,14,17-eicosatrienoic acid), 22:0 (behenic acid), 22:1 (13c) (erucic acid), 24:0 (tetracosanoic acid), 24:1 (15c) (15-tetracosenoic acid) and 18:3 (9c, 11t, 13c) (punicic acid). The first value represents the number of carbon atoms, the second value represents the number of unsaturated bonds, the value immediately after the number of unsaturated bonds in the parenthesis represents the position of the unsaturated bond, and c and t represent cis and trans, respectively.

TABLE 1

Fatty acid composition of *Arabidopsis* transformant (T1) seeds expressing *Trichosanthes kirilowii*-derived conjugase (TkFac)

| Fatty acid weight %[1] | Non-transformant (n = 6) | PKS-TkFac (n = 6) | PKN-TkFac (n = 6) |
|---|---|---|---|
| 16:0 | 7.6 ± 0.5 | 7.6 ± 0.2 | 7.2 ± 0.3 |
| 18:0 | 2.6 ± 0.4 | 2.9 ± 0.1 | 3.2 ± 0.1 |
| 18:1 (9c) | 15.2 ± 1.5 | 16.2 ± 1.9 | 22.8 ± 3.7 |
| 18:2 (9c, 12c) | 30.3 ± 1.0 | 28.4 ± 1.3 | 23.3 ± 2.5 |
| 18:3 (9c, 12c, 15c) | 19.4 ± 1.5 | 20.0 ± 1.0 | 14.6 ± 3.6 |
| 20:0 | 1.8 ± 0.3 | 1.9 ± 0.1 | 1.7 ± 0.2 |
| 20:1 (11c) | 16.8 ± 0.9 | 17.8 ± 0.6 | 18.7 ± 0.8 |
| 20:2 (11c, 14c) | 1.8 ± 0.2 | 1.7 ± 0.2 | 1.1 ± 0.3 |
| 20:3 (11c, 14c, 17c) | 0.4 ± 0.1 | 0.5 ± 0.1 | 0.3 ± 0.1 |
| 22:1 (13c) | 1.7 ± 0.3 | 1.7 ± 0.1 | 1.5 ± 0.1 |
| Punicic (9c, 11t, 13c) | N.D.[2] | 0.4 ± 0.4 | 3.5 ± 3.3 |
| 20:3[3] | N.D. | 0.1 ± 0.1 | 0.4 ± 0.3 |
| Others[4] | <3.0 | <2.0 | <2.0 |

[1]Fatty acid composition is expressed by % with respect to the total weight of lipids.
[2]N.D. = not detected
[3]20:3 isomer predicted to contain a conjugated double bond
[4]Others mainly include 18:1 and 20:1 isomers, and also include 22:0, etc.

(15) Production of *Brassica napus* Transformant

*Brassica napus* (*Brassica napus* cv. Westar) was transformed by the method described in Plant Mol. Biol. 26, 1115-1124, 1996. This is to say, *Brassica napus* was aseptically germinated on an MS medium containing 3% sucrose, and the lower hypocotyl was cut out into a 2 to 5 mm section. The section was then precultured overnight on a preculture medium (B5 medium containing 0.2 µg/ml 2,4-D and 3% sucrose). The same *Agrobacterium* as used for *Arabidopsis* was grown in a YEB medium. Cells were collected by centrifugal separation at 4,000 g for 10 minutes, and they were resuspended in an MS medium containing 3% sucrose. The above *Brassica napus* lower hypocotyls were added to the suspension, followed by shaking for 20 minutes. The lower hypocotyls were taken out and air-dried on a sterilized filter. Then, they were returned to the previous preculture medium and cocultured with *Agrobacterium* for 3 days. Thereafter, the hypocotyls were transferred into a selective medium (B5 medium containing 2 µg/ml Zeatin, 3 µg/ml BAP, 1 to 2% sucrose, and 500 µg/ml carbenicillin) containing kanamycin (30 µg/ml), followed by selection. The thus obtained green regeneration buds were cultured in a regeneration medium (B5 medium containing 0.5 µg/ml BAP, 3% sucrose, 500 µg/ml carbenicillin, and 30 µg/ml kanamycin) and in a rooting medium (MS medium containing 0.01 µg/ml NAA, 0.4 µg/ml BAP, 1% sucrose, and 250 µg/ml carbenicillin), so as to obtain regenerated individuals. From the leaves of these regenerated individuals, DNA was extracted using Dneasy Plant Mini (manufactured by Qiagen). 3 µl of the extracted DNA was added to 20 µl of a PCR reaction solution containing 1 µM each of the primers shown in SEQ ID NOS: 6 and 7, followed by performing a PCR reaction under the same conditions as in (7) above. Thereafter, the reaction product was subjected to electrophoresis. As a result, bands of the expected size were observed, and it was confirmed that they were transformants. These transformants were acclimated, and their self-pollinated seeds (T1 seeds) were collected.

Figure 5:
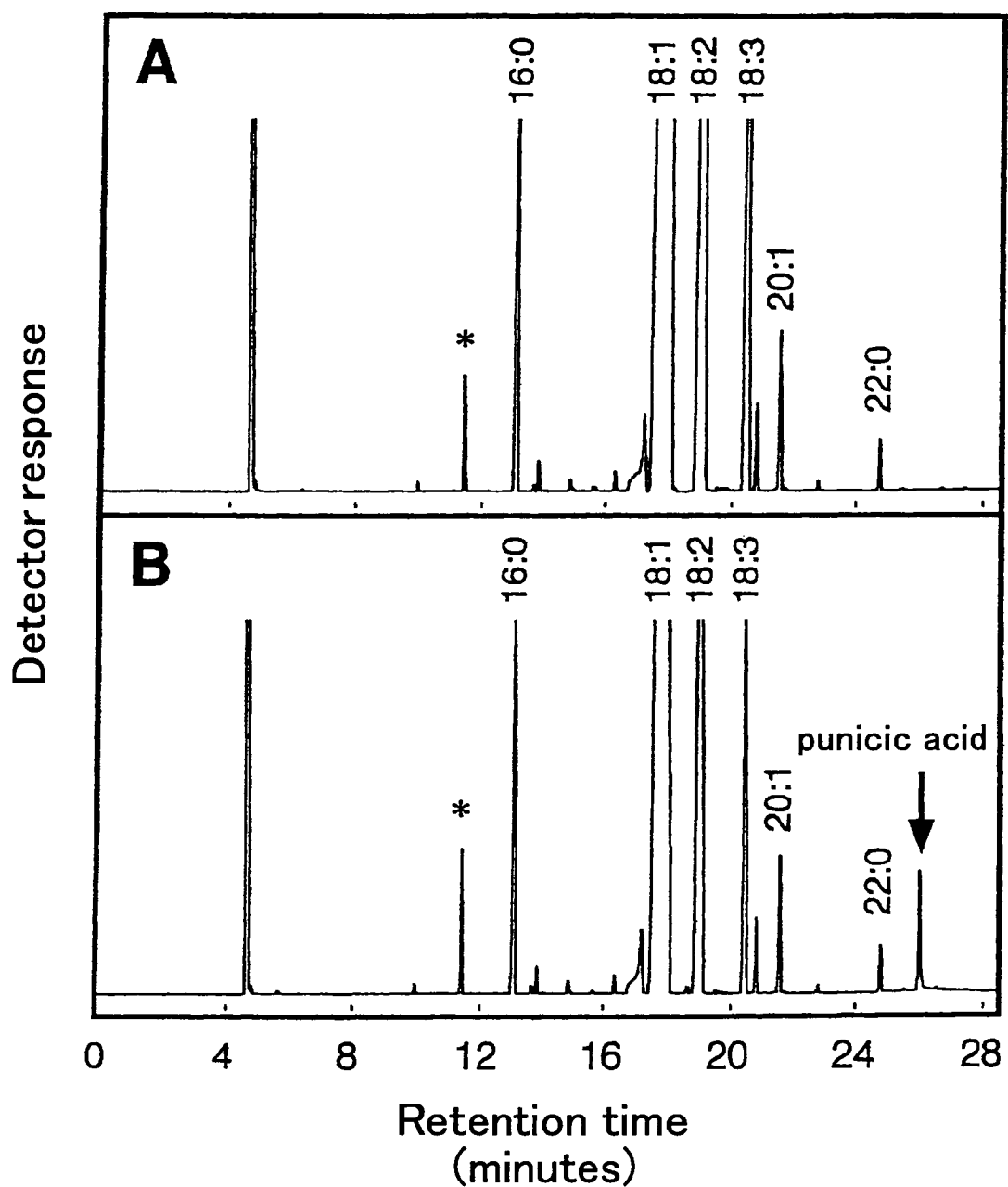
FIG. 5 shows results obtained by GC analyses of fatty acid methyl esters prepared from each of seeds (A) of non-transformed rapeseed and seeds (B) of rapeseed transformed with pKN-TkFac. The mark * in the figure represents a peak corresponding to pentadecanoic acid methyl ester added to the samples.

(16) Fatty Acid Analysis of *Brassica napus* Transformant 5 grains from the obtained T1 seeds were ground with a pestle in a mortar, and 1 ml of 0.5 M sodium methoxide/methanol was added thereto and suspended. The suspension was then transferred into a glass tube, followed by a methylation reaction at 50° C. for 1 hour. Thereafter, lipid analysis was carried out in the same manner as for the lipid analysis of the *Arabidopsis* transformant described in (14) above. When fatty acid composition was compared between a non-transformant seeds and the transformant T1 seeds by GC analysis, a new peak was detected in the transformant T1 seeds (FIG. 5B). This peak was not detected in the non-transformant seeds (FIG. 5A). This peak (FIG. 5B, arrow) was detected at the same time when the peak of punicic acid methyl ester contained in the *Trichosanthes kirilowii* seed fatty acid GC sample was detected. Accordingly, it became clear that the *Trichosanthes kirilowii*-derived conjugase produced punicic acid in *Brassica napus* seeds. The peaks indicated with the values in FIG. 5 show various fatty acid methyl esters, and they specifically represent 16:0 (palmitic acid), 18:1 (9c) (oleic acid), 18:2 (9c, 12c) (linoleic acid), 18:3 (9c, 12c, 15c) (α-linolenic acid), 20:1 (11c) (gondoic acid), 22:0 (behenic acid) and 18:3 (9c, 11t, 13c) (punicic acid). The first value represents the number of carbon atoms, the second value represents the number of unsaturated bonds, the value immediately after the number of unsaturated bonds in the parenthesis represents the position of the unsaturated bond, and c and t represent cis and trans, respectively.

Example 2

*Punica granatum* Conjugase (1) Isolation of RNA from *Punica granatum*

*Punica granatum* immature seeds that started to accumulate conjugated triene fatty acid, punicic acid, were collected, and the seeds were used as materials for isolating total RNA. As described in Molecular Cloning, there are various methods of preparing total RNA, including the guanidine hydrochloride method. Of those methods, the phenol-chloroform method (*Arabidopsis* Protocols, Methods in Mol. Biol. 82, p. 85-89 Humana Press) was applied in the present example. That is, approximately 0.6 g of the immature seeds from which the seed coats were removed was mixed with liquid nitrogen in a mortar, and the mixture was fully crushed and then transferred into 15 ml tubes. 1.8 ml of an extract solution (0.4 M LiCl, 25 mM EDTA, 1% SDS, 0.2 M Tris buffer solution (pH 9.0)) and 1.8 ml of phenol saturated with water treated with diethylpyrocarbonate (DEPC) were added to each tube, followed by stirring by Vortex. The obtained mixture was centrifuged at 4° C. at 750 g for 5 minutes. Thereafter, each of the upper layers was transferred into a new 15 ml tube, with caution against suspended matters. 1.8 ml of phenol saturated with sterilized water was added thereto again, the mixture was fully stirred, and it was then centrifuged in the same manner as described above. The upper layer was transferred into a new tube. An equal amount of chloroform was added thereto and stirred, and the upper layer was recovered by centrifugal separation. This operation was repeated three times in the same manner as described above. A one-tenth amount of 3 M sodium acetate and 2 times amount of 95% ethanol were added to the recovered upper layer, followed by leaving at rest at −80° C. for 30 minutes. Thereafter, the obtained product was subjected to centrifugal separation at 4° C. at 14,000 g for 10 minutes, and 1.4 ml of 2 M lithium chloride was added to the obtained precipitate. The mixture was fully stirred to dissolve it, and it was then left at rest on ice for 30 minutes or longer, so that RNA was separated from DNA. The RNA was subjected to centrifugal separation at 4° C. at 14,000 g for 10 minutes, and the obtained precipitate was dissolved in 0.8 ml of 2M lithium chloride again. The solution was left at rest on ice for 30 minutes and then subjected to centrifugal separation to recover RNA. The obtained RNA was dissolved in 0.8 ml of sterilized water. A one-tenth amount of 3 M sodium acetate and 2 times amount of 95% ethanol were added thereto, and the obtained mixture was left at rest at −80° C. for 5 minutes. Thereafter, the mixture was subjected to centrifugal separation at 4° C. at 14,000 g for 5 minutes, so as to precipitate RNA. The obtained precipitate was washed with 70% ethanol, and then dried. The dried product was dissolved in 100 µl of sterilized water, so as to obtain an RNA solution.

(2) Synthesis of cDNA

Using RNA as a template, cDNA synthesis is carried out with reverse transcriptase and primers, which depend on purposes. In the present example, first strand cDNA was synthesized, using reverse transcriptase, SuperScript II RNase H− Reverse transcriptase manufactured by Gibco BRL, and oligo dT primers. Subsequently, the second strand cDNA was synthesized using a Marathon cDNA Amplification Kit manufactured by CLONTECH, so as to obtain a double strand cDNA. More specifically, oligo (dT) primers (0.5 µg) binding to a poly A sequence was added to the total RNA (10 µg) that was derived from the *Punica granatum* immature seeds obtained in (1) above and was to be used as a template to synthesize the first strand cDNA, and the obtained mixture was treated at 70° C. for 2 minutes and then cooled on ice. Thereafter, a first-strand buffer (final concentration: 50 mM Tris, 3 mM $MgCl_2$, 75 mM KCl, pH 8.3), a dNTP mixture (final concentration: 0.5 mM each), dithiothreitol (final concentration: 10 mM), RNaseOUT Recombinant Ribonuclease Inhibitor (40 units, manufactured by Gibco BRL) were mixed with the above reaction product, and the obtained mixture was incubated at 48° C. for 2 minutes. Thereafter, reverse transcriptase (400 units) was further added thereto, so that the total 20 μl of a reaction solution was prepared and then incubated at 48° C. for 1 hour. After the reaction was terminated, the obtained reaction solution was cooled on ice. By this operation, the first strand cDNA was synthesized.

Subsequently, using a kit manufactured by CLONTECH, a second-strand buffer (final concentration: 20 mM Tris, 100 mM KCl, 10 mM ammonium acetate, 5 mM $MgCl_2$, 0.15 mM β-NAD, 0.05 mg/ml bovine serum albumin), a dNTP mixture (final concentration: 0.05 mM each), *E. coli* DNA polymerase 1 (12 units), *E. coli* RNase H (0.5 units) and sterilized water were added to 10 μl of the above synthesized first strand cDNA solution, so as to prepare the total 40 μl of solution. The obtained solution was mixed and incubated at 16° C. for 90 minutes. Thereafter, 10 units of T4 DNA Polymerase were added thereto and mixed, and the obtained mixture was further incubated at 16° C. for 45 minutes. Thereafter, EDTA (final concentration: 10 mM) and glycogen (final concentration: 0.1 mg/ml) were added thereto, and the reaction was terminated. Phenol/chloroform/isoamyl alcohol (25:24:1) was added to the reaction solution, and the mixture was stirred and then subjected to centrifugal separation at 7,000 g for 10 minutes to recover a supernatant. Chloroform/isoamyl alcohol (24:1) was added to the recovered supernatant, and the mixture was stirred and then subjected to centrifugal separation under the same conditions as above. The supernatant was recovered, and 1.5 times amount of 4 M ammonium acetate was added thereto. 95% ethanol was further added thereto in an amount of 2.5 times of the mixture, and the thus obtained mixture was well mixed. Thereafter, the mixture was centrifuged at 14,000 g for 20 minutes at room temperature, and the obtained precipitate was dissolved in 10 μl of sterilized water, so as to obtain a double stand cDNA solution.

(3) Setting of Primer Region

Homology comparison was performed on amino acid sequences of a Δ12-desaturase gene and other genes, which had been reported until then, so as to search for common sequences. With regard to Δ12 desaturase genes of *Arabidopsis* (accession No. L26296) and *Calendula officinalis* (accession No. AF343065), eleostearic acid-synthesizing conjugase genes of *Momordica charantia* (accession No. AF182521) and *Impatiens balsamica* (accession No. AF182520), calendic acid-synthesizing conjugase genes of *Calendula officinalis* (accession Nos. AF343064, AF310155 and AF310156), and a conjugase of *Trichosanthes kirilowii* (Japanese Patent Application No. 2001-28639), their proteins were aligned to search for highly homologous regions. From among such regions, those, which contained a region conserved among these membrane localized desaturase genes and were approximately 500 bp apart from each other, were selected regardless of the functions of the enzymes. Thereafter, primers were produced by the comparison of amino acid sequences and nucleotide sequences, considering the degeneracy of nucleotides having the nucleotide sequences shown in SEQ ID NOS: 14 to 16.

(4) Isolation of Partial Sequence of Punicic Acid Synthetase (Conjugase) cDNA by RT-PCR 1 μl of a solution obtained by diluting the first strand cDNA solution synthesized in (2) above with a TE buffer to 1/20, 1 μM each of primers shown in SEQ ID NOS: 14 and 16, and 2.5 units of Takara Ex Taq DNA polymerase (Takara Bio Inc.) were added to a PCR reaction solution so as to prepare the total 50 μl of a solution, which was then subjected to a PCR reaction under the following conditions. This is to say, after heating at 94° C. for 1 minute, a cycle consisting of denaturation at 94° C. for 30 seconds, annealing at 52° C. for 1 minute, and elongation at 72° C. for 40 seconds was repeated 30 times, and finally the reaction product was heated at 72° C. for 10 minutes. After completion of the reaction, an aliquot of the reaction solution was subjected to 1% agarose gel electrophoresis, and then stained with ethidium bromide. As a result, a band of the expected size was confirmed. Thus, the reaction solution was deproteinized with 50 μl of phenol/chloroform/isoamyl alcohol (25:24:1), and the upper layer was transferred into a new tube. 5 μl of a 3 M-sodium acetate solution (pH 5.2) and 125 μl of ethanol were added thereto, and the mixture was left at rest at −80° C. for 15 minutes, and then subjected to centrifugal separation at 14,000 g for 10 minutes, so as to obtain a precipitate containing DNA fragments. This precipitate was dissolved in 10 μl of sterilized water, and the product was subjected to 0.8% agarose gel electrophoresis and then stained with ethidium bromide. Thereafter, a band of a size of interest was cut out of the gel, and a solution containing amplified fragments was recovered using SUPREC-01 (manufactured by Takara Bio Inc.), followed by ethanol precipitation. Thereafter, the purified DNA fragment was dissolved in 10 μl of sterilized water. 4.5 μl from the obtained solution was mixed with 0.5 μl (25 ng) of a plasmid vector pGEM-T Easy (manufactured by Promega), and the obtained mixture was then subjected to a ligation reaction at 16° C. overnight, using a DNA ligation kit (manufactured by Takara Bio Inc.) Using 2 μl from the reaction solution, *Escherichia coli* (DH5α) was transformed by Hanahan's method (DNA cloning, vol. 1, pp. 109-136 (1985)), so as to obtain white colonies that were formed on an LB medium containing ampicillin (50 μg/ml) and X-gal.

(5) Screening of cDNA Clone 6 clones were randomly picked up from the clones obtained in (4) above. A portion was scraped off from each colony, and the portion was added to 20 PL of a PCR reaction solution containing 1 μM each of the primers shown in SEQ ID NOS: 15 and 16, followed by performing a PCR reaction under the same conditions as in (4) above. After completion of the reaction, an aliquot of the reaction solution was subjected to 1% agarose gel electrophoresis, and then stained with ethidium bromide. As a result, a band of the expected size was confirmed. Thus, plasmid DNA was prepared from these clones, and the sequences of cDNA inserted therein were analyzed using SP6 primers (ABI Prism BigDye Terminator Cycle Sequencing Ready Reaction Kit, ABI Prism 310 Genetic Analyzer: manufactured by PE Applied Biosystems). The obtained nucleotide sequences were translated into amino acid sequences, using GENETYX (manufactured by Software Development), and the obtained sequences were compared with one another. As a result, the 6 clones were classified into 2 types of cDNA, and it was determined that the one type is highly likely to be a partial sequence of a *Punica granatum* conjugase gene. Thus, based on this information, primers specific for the cDNA sequences shown in SEQ ID NOS: 19 to 22 were synthesized, and clones containing 5' and 3' regions of the cDNA sequences were obtained according to the method mentioned below.

(6) Isolation of *Punica granatum* Conjugase cDNA by 5' and 3' RACE Method 2.5 μl of the double strand cDNA solution prepared in (2) above was reacted at 16° C. overnight using a ligation kit (manufactured by Takara Bio Inc.), so that adaptors were ligated to the both ends of the double strand cDNA. The reaction solution was diluted with a dilution buffer (10 mM Tricine-KOH, 0.1 mM EDTA, pH8.5) to 1/50 to 1/250. The thus diluted solution was used as a template. With regard to 5' RACE, using AP1 that is a primer to the adaptor and a primer shown in SEQ ID NO: 21, the same PCR reaction solution as in (4) above was prepared, and a PCR reaction was carried out under the following conditions. That is, after heating at 94° C. for 1 minute, a cycle consisting of denaturation at 94° C. for 30 seconds, annealing at 55° C. for 1 minute, and elongation at 72° C. for 1 minute was repeated 30 times, and finally the reaction product was heated at 72° C. for 10 minutes. With regard to 3' RACE, using the AP1 and a primer shown in SEQ ID NO: 23, the same PCR reaction solution as in (4) above was prepared, and a PCR reaction was carried out under the following conditions. That is, after heating at 94° C. for 1 minute, a cycle consisting of denaturation at 94° C. for 30 seconds, annealing at 55° C. for 1 minute, and elongation at 72° C. for 1.5 minutes was repeated 30 times, and finally the reaction product was heated at 72° C. for 10 minutes. An aliquot of each of the reaction solutions was subjected to agarose gel electrophoresis. As a result, one band with an expected size was detected in each aliquot. In order to confirm whether these bands contained the cDNA, 1 µl was taken out of each of the reaction products of 5' and 3' RACE, and it was subjected to nested PCR. This is to say, with regard to 5' RACE, using AP2 that is a primer to the adaptor and a primer shown in SEQ ID NO: 22, PCR was carried out under the same above conditions. With regard to 3' RACE, using the AP2 and a primer shown in SEQ ID NO: 24, PCR was carried out under the same above conditions. After completion of the reactions, an aliquot was taken out of each of the reaction products, and it was subjected to agarose gel electrophoresis. As a result, a single band of the expected size was detected in each aliquot. These bands were cut out of the agarose gel, and DNA fragments were purified by the same method as in (4) above. The fragments were ligated to pGEM-T Easy, and DH5α was transformed therewith, so as to obtain white colonies that were formed on an LB medium containing ampicillin (50 µg/ml) and X-gal.

Multiple clones were randomly picked up from the clones obtained in (6) above. A portion was scraped off from each colony, and it was then added to 20 µl of a reaction solution, followed by performing a PCR reaction under the same conditions as for the nested PCR in (6) above. After completion of the reaction, an aliquot of the reaction solution was subjected to 1% agarose gel electrophoresis, and then stained with ethidium bromide. Multiple clones were selected from the clones, in which a band of the expected size was confirmed, and plasmid DNA was prepared from these clones. Thereafter, the cDNA inserted into the plasmid was sequenced using T7 and SP6 primers. The obtained nucleotide sequences were translated into amino acid sequences, using GENETYX (manufactured by Software Development), and the obtained sequences were compared with one another. As a result, it was confirmed that all the nucleotide sequences contained the partial sequence of the 5'- or 3'-end of the cDNA.

(7) Isolation of Full-Length cDNA of *Punica granatum* Conjugase

Based on the information on the nucleotide sequences of the 5'- and 3'-ends regions of the conjugase cDNA obtained in (6) above, 2 sets of primers were prepared to isolate the full-length cDNA of *Punica granatum* conjugase. That is, a 5' primer of the first set was obtained by adding an EcoRV/XbaI site to the 5' side of 25 nucleotides containing a translation initiation codon ATG of the *Punica granatum* conjugase shown in SEQ ID NO: 17. On the other hand, a 3' primer of the first set was obtained by adding a SacI site to the 5' side of a sequence complementary to 7 to 33 nucleotides downstream of a translation termination codon TGA of the conjugase gene shown in SEQ ID NO: 18. The second set consisted of a 5' primer shown in SEQ ID NO: 19 corresponding to the 5' non-translation region of the cDNA of *Punica granatum* conjugase and a 3' primer shown in SEQ ID NO: 20 corresponding to the 3' non-translation region thereof. The double strand cDNA solution prepared in (2) above was diluted with a TE buffer to 1/30. Using 2.5 or 5 µl of the diluted solution and 1 µM each of the above 5' primer and 3' primer of either one of the above primer sets, 2 samples were prepared from each primer set. Each sample consisted of 50 µl of a PCR reaction solution containing 5 units of Pyrobest DNA polymerase (manufactured by Takara Bio Inc.). Using these samples, PCR was carried out under the following conditions. That is, after heating at 94° C. for 1 minute, a cycle consisting of denaturation at 94° C. for 30 seconds, annealing at 55° C. for 1 minute, and elongation at 72° C. for 2.5 minutes was repeated 25 times, and finally the reaction product was heated at 72° C. for 10 minutes. 5 units of Takara Ex Taq were further added to the reaction product, followed by heating at 72° C. for 10 minutes. An aliquot of the reaction solution was subjected to 1% agarose gel electrophoresis, and then stained with ethidium bromide. As a result, a band of the expected size was confirmed in all of the 4 samples. Thus, the amplified DNA fragments were purified by the same method as in (4) above. Each of the fragments was then ligated to pGEM-T Easy, and DH5α was transformed therewith, so as to obtain white colonies that were formed on an LB medium containing ampicillin (50 µg/ml) and X-gal.

1 clone was randomly picked up from the obtained clones. A portion was scraped off from each colony, and it was then added to 20 µl of a PCR reaction solution, followed by performing a PCR reaction under the same conditions as in (7) above. After completion of the reaction, an aliquot of the reaction solution was subjected to 1% agarose gel electrophoresis, and then stained with ethidium bromide. 2 clones each were selected from the clones, in which a band of the expected size was confirmed, and plasmid DNA was prepared from these clones. Thereafter, the cDNA inserted into the plasmid was sequenced using gene specific primers. The obtained nucleotide sequences were translated into amino acid sequences, using GENETYX (manufactured by Software Development), and the obtained sequences were compared with one another. As a result, it was confirmed that all the nucleotide sequences contained the full length of the cDNA.

(8) Structural Analysis of *Punica granatum* Conjugase cDNA

The isolated *Punica granatum* conjugase cDNA (PgFac) was 1,374 bp and it encoded 395 amino acids. The amino acid sequence encoded by the isolated conjugase cDNA is shown in SEQ ID NO: 12, and its nucleotide sequence is shown in SEQ ID NO: 13.

It was confirmed by homology comparison with database that the *Punica granatum* conjugase cDNA had 62% homology with *Momordica charantia* conjugase cDNA, 60% homology with Impatiens balsamica conjugase cDNA, 57% homology with *Calendula officinalis* conjugase cDNA, and 64% homology with *Trichosanthes kirilowii* conjugase cDNA, among genes whose functions had been analyzed. When the amino acid sequence of PgFac was compared with the existing conjugases, it was found that the amino acid sequence had 56% homology with Momordica charantia, 56% homology with *Impatiens balsamica,* 46% homology with *Calendula officinalis* and 56% homology with *Trichosanthes kirilowii,* and that it contained a region conserved among these existing conjugases. Accordingly, it was assumed that the present gene was a conjugase.

(9) Construction of Yeast Protein Expression Shuttle Vector Containing *Punica granatum* Conjugase cDNA The plasmid DNA containing the *Punica granatum* conjugase full-length cDNA obtained in (7) above was cleaved with restriction enzymes EcoRV and SacI. The obtained cDNA fragment was purified by the same method as in (4) above and then ligated to a plasmid vector pBluescript II SK+ (manufactured by STRATAGENE), and DH5α was transformed therewith, so as to obtain white colonies that were formed on an LB medium containing ampicillin (50 μg/ml) and X-gal. Plasmid DNA was extracted from the colonies containing the cDNA fragments, and then cleaved with restriction enzymes HindIII and SacI. A fragment containing the cDNA was purified by the same above method, and it was then ligated to the HindIII-SacI site of a protein expression shuttle vector pYES2. DH5α was transformed with the vector, so as to obtain colonies formed on an LB medium containing ampicillin (50 μg/ml). Plasmid DNA was extracted from these transformants, and those containing the cDNA (pYES2/PgFac) were selected, which was then used in the following transformation of yeast.

(10) Preparation of Transformed Yeast

Using *Saccharomyces cerevisiae* D452-2, yeast competent cells were prepared using S.c. EasyComp Transformation Kit (manufactured by Invitrogen), and they were then transformed. This is to say, yeast was streaked onto a YPD agar medium (1% yeast extract, 2% peptone, 2% D-glucose, 2% Agar) and cultured at 28° C. for 2 days, so as to obtain colonies. A single colony was transferred into 10 ml of a YPD medium (1% yeast extract, 2% peptone, 2% D-glucose) and then subjected to shake culture at 28° C. overnight. Thereafter, the culture solution was diluted with a YPD medium, so as to prepare 10 ml of a culture solution having $OD_{600}$ of 0.2 to 0.4. The obtained culture solution was further subjected to shake culture at 28° C. until $OD_{600}$ became 0.6 to 1.0. Thereafter, the solution was centrifuged at 500 g for 5 minutes at room temperature to recover cells, and the cells were suspended in 10 ml of washing solution. The suspension was centrifuged again under the same above conditions to recover cells. 1 ml of a lithium solution was added thereto, and the cells were suspended therein, and the suspension was divided into 50 μl each, which was then stored at −80° C.

50 μl of the yeast competent cells was melted at room temperature. 1 μg of pYES2 or the plasmid DNA (pYES2/PgFac) containing *Punica granatum* conjugase full-length cDNA obtained in (9) above was added thereto, and the mixture was blended. 500 μl of a transformation solution was added thereto, and the mixture was well blended. The mixture was incubated at 30° C. for 1 hour while stirring every 15 minutes. Thereafter, 1 ml of a YPD medium was added thereto, and the mixture was subjected to shake culture at 30° C. for 1 hour and then centrifuged at room temperature at 3,000 g for 5 minutes, so as to recover cells. The cells were suspended in 250 μl of an SC minimal medium (−Ura/2% glucose), and the suspension was dispersed on the same agar medium, followed by culture at 30° C. for 3 or 4 days. The 6 grown colonies were selected, and a portion of them was transferred into 3 ml of an SC minimal medium (−Ura/2% glucose), followed by culture at 28° C. overnight. Thereafter, sterilized glycerol (final concentration: 15%) was added to the culture, and the mixture was well blended and conversed at −80° C. On the other hand, an aliquot of the culture solution was dispersed on an SC minimal medium (−Ura/2% glucose), followed by culture at 30° C. for 2 days. Thereafter, a portion of the obtained colonies was taken, and the portion was added to 20 μl of a PCR reaction solution containing 1 μM each of primers shown in SEQ ID NOS: 17 and 18, and PCR was carried out under the same conditions as in (7) above. As a result, it was confirmed that all of the colonies obtained by transformation with pYES2/PgFac were transformants containing *Punica granatum* conjugase cDNA.

(11) Analysis of Fatty Acid in Yeast Transformant

The yeast transformant prepared in (10) above was transferred into 3 ml of an SC minimal medium (−Ura/2% glucose), followed by culture at 28° C. overnight. Cells recovered by centrifugal separation were washed with sterilized water, and they were then suspended in an SC-Gal minimal medium (−Ura/2% galactose). The suspension was then added to 50 ml of an SC-Gal minimal medium (−Ura/2% galactose) containing or not containing 0.1% (W/V) Tergitol type NP-40 (Sigma) and 0.3 mM linoleic acid, such that $OD_{600}$ became 0.2. The mixture was subjected to shake culture at 20° C. at 200 rpm for 3 days, and it was further cultured at 15° C. for 3 days. The yeast culture solution as a whole was transferred into a glass tube, and it was centrifuged at 1,700 g for 5 minutes to precipitate yeast. Then, 40 ml of 1% (W/V) Tergitol type NP-40 (Sigma) was added thereto, and the mixture was suspended by Vortex. The suspension was centrifuged at 2,000 g for 10 minutes, so that yeast was precipitated again and washed. The obtained precipitate was washed with Tergitol again, and then washed with 40 ml of sterilized water 3 times in the same manner as above. 25 ml of sterilized water was added to the washed precipitate, and the mixture was suspended by Vortex. 5 ml each of the suspension was poured into a glass tube, and it was then centrifuged at 2,000 g for 10 minutes, so as to obtain a precipitate again. The obtained precipitate was frozen at −80° C., and then freeze-dried for 4 hours. Thereafter, 1 ml of 0.5 M sodium methoxide/methanol was added to each glass tube (5 ml in total), and a methylation reaction was carried out at 50° C. for 1 hour. In some cases, during the methylation reaction, 50 nmol of pentadecanoic acid ($C_{15:0}$) methyl was added to the sample as an internal standard. The reaction solution was returned to room temperature, and thereafter, 7.5 ml 0.9 M NaCl and 5 ml of hexane were added thereto and suspended. The obtained mixture was centrifuged at 1,700 g for 5 minutes, and the obtained supernatant was then subjected to vacuum drying. Thereafter, 20 μl of hexane was added to and dissolved in fatty acid methyl esters extracted by the above operation, and 1 μl of the mixed solution was analyzed by gas chromatography (GC) using GC18A (Shimadzu). For this analysis, using a capillary column (GL Science) with TC-70, 60 m×0.25 mm and a 0.25 μm ID, the temperature was raised from 150° C. to 240° C. at a speed of 3° C./min, and then an isothermal analysis was carried out at 240° C. for 6 minutes.

Figure 6:
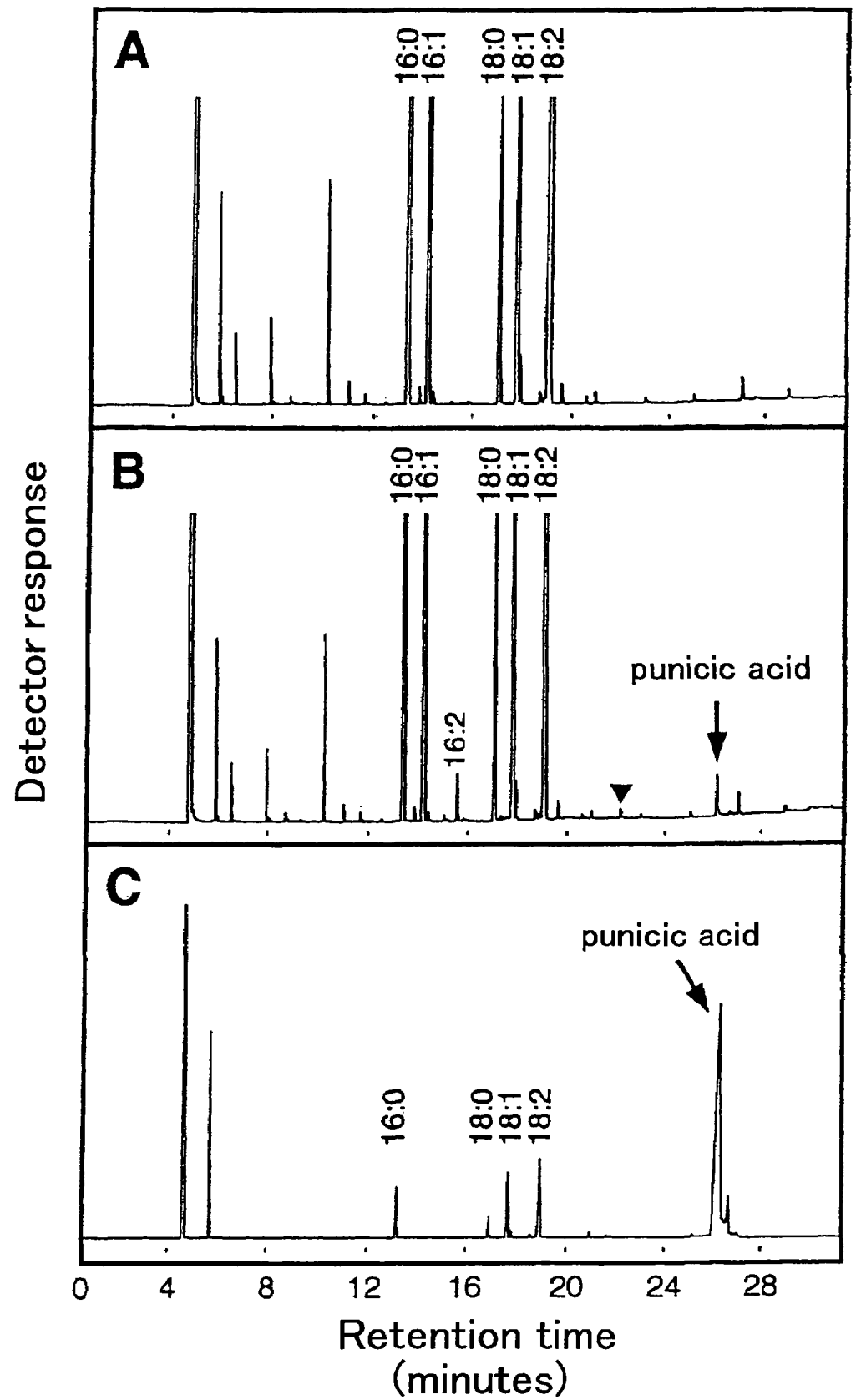
FIG. 6 shows results obtained by GC analyses of fatty acid methyl esters prepared from each of yeast cells (A) into which pYES2 was introduced, yeast cells (B) into which pYES2/PgFac was introduced, and immature seeds (C) of *Punica granatum.* The yeast cells were cultured in a medium to which linoleic acid was added.
Figure 7:
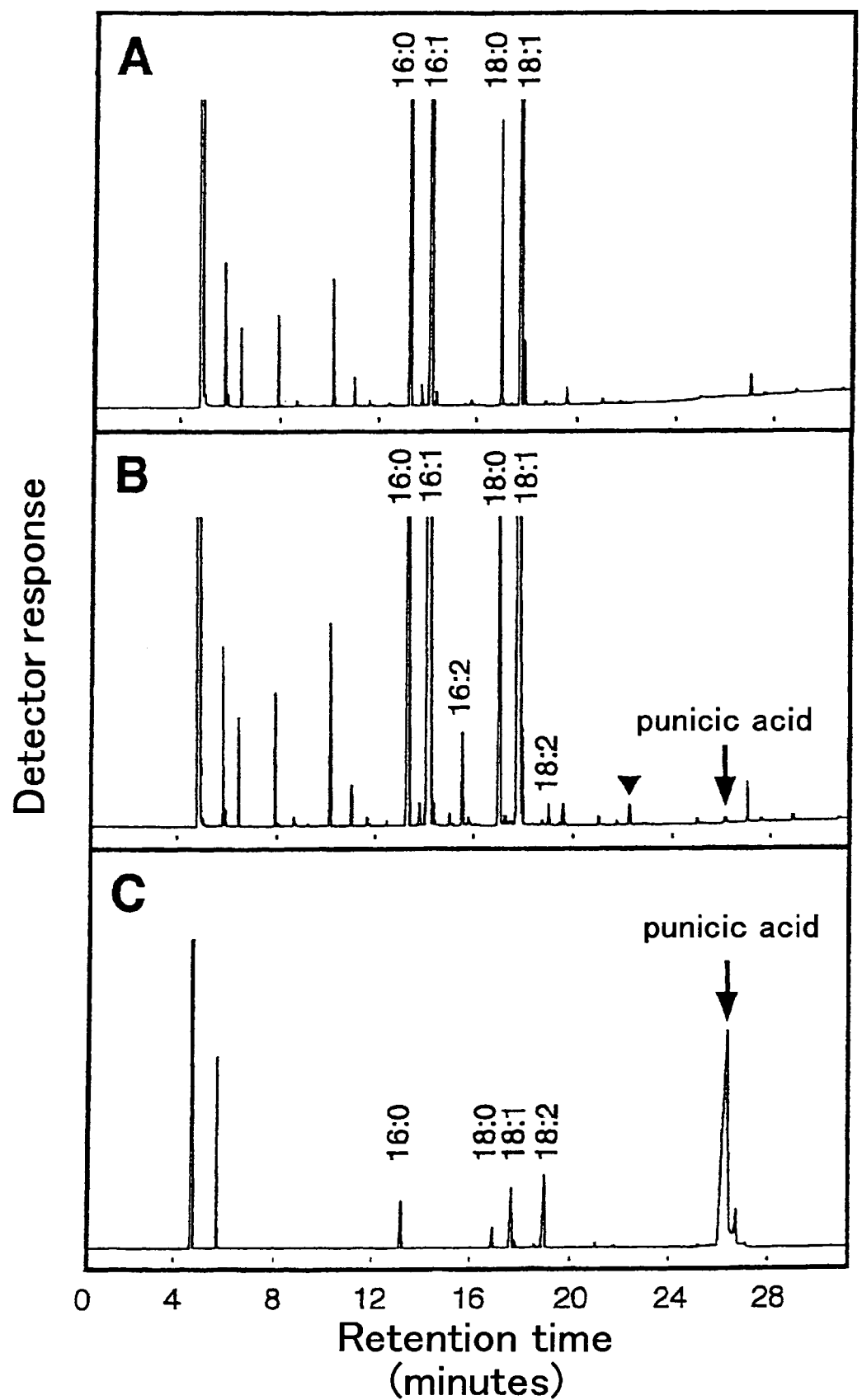
FIG. 7 shows results obtained by GC analyses of fatty acid methyl esters prepared from each of yeast cells (A) into which pYES2 was introduced, yeast cells (B) into which pYES2/PgFac was introduced, and immature seeds (C) of *Punica granatum.* The yeasts were cultured in a medium to which linoleic acid was not added.

Transformed yeasts were cultured in a medium which contained or did not contain 0.3 mM linoleic acid, and the obtained fatty acids as a whole were then analyzed by GC. As a result, a new peak was detected in the pYES2/PgFac transformed yeast (FIGS. 6 and 7). This peak was not observed in the pYES2 transformed yeast. In order to examine whether this peak was derived from punicic acid, the fatty acids of *Punica granatum* seeds accumulating punicic acid was subjected to GC analysis for comparison. Hard hulls were removed from three *Punica granatum* seeds. The remained seed portions were completely ground with a pestle in a mortar that was cooled on ice, and 1 ml of 0.5 M sodium methoxide/methanol was added thereto. The mixture was stirred and suspended with a pestle, and then transferred into a glass tube. This was subjected to a methylation reaction at 50° C. for 1 hour, and thereafter, 1.5 ml of 0.9 M NaCl and 1 ml of hexane were added to the reaction product, followed by stirring and extraction. The extract was centrifuged at 2,000 g for 5 minutes, and the obtained supernatant was subjected to vacuum drying. To the thus extracted fatty acid methyl esters, 20 μl of hexane was added and dissolved. 1 μl of the obtained solution was subjected to GC analysis in the same manner as described above, so as to examine the detection time of punicic acid methyl ester contained in *Punica granatum* seeds (FIGS. 6C and 7C, arrow). As a result, the above detection time matched the detection time of a peak (FIG. 6B and 7B, arrow) that was newly detected in the pYES2/PgFac transformed yeast. Moreover, a mixture consisting of the *Punica granatum* seeds-derived fatty acid GC sample and the above yeast-derived fatty acid sample was subjected to GC analysis, and as a result, it was confirmed that the peak of punicic acid methyl ester contained in the *Punica granatum* seeds and the peak of the yeast indicated with the arrow were detected at the same time. Furthermore, the peaks indicated with the arrows in FIGS. 6B and 7B was subjected to GC-MS analysis in EI mode, using an Agilent 6890 Series gas chromatograph, a JEOL JMS-600H Msroute mass spectrometer, and the above-described column. As a result of the GC-MS (EI) analysis, it was found that an $M^+$ ion peak appeared at m/z=292, and that the above peak was similar to the spectrum of a 18:3 (9c, 12c, 15c) methyl ester sample analyzed in the same manner, in terms of appeared peak and intensity ratio. Thus, it was concluded that the above peak was 18:3 fatty acid methyl ester.

Figure 8:
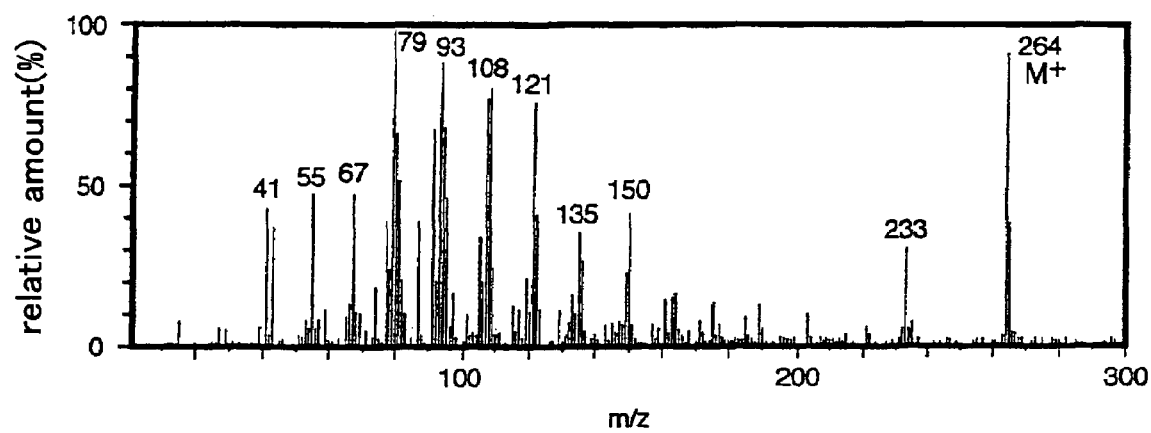
FIG. 8 shows results obtained by comparing a mass spectrum (A) obtained by GC-MS (EI) analysis of the peak indicated with a tip in FIG. 7B, with a mass spectrum (B) of 16:3 (7,10,13-hexadecatrienoic acid) methyl ester analyzed in the same manner.
Figure 8:
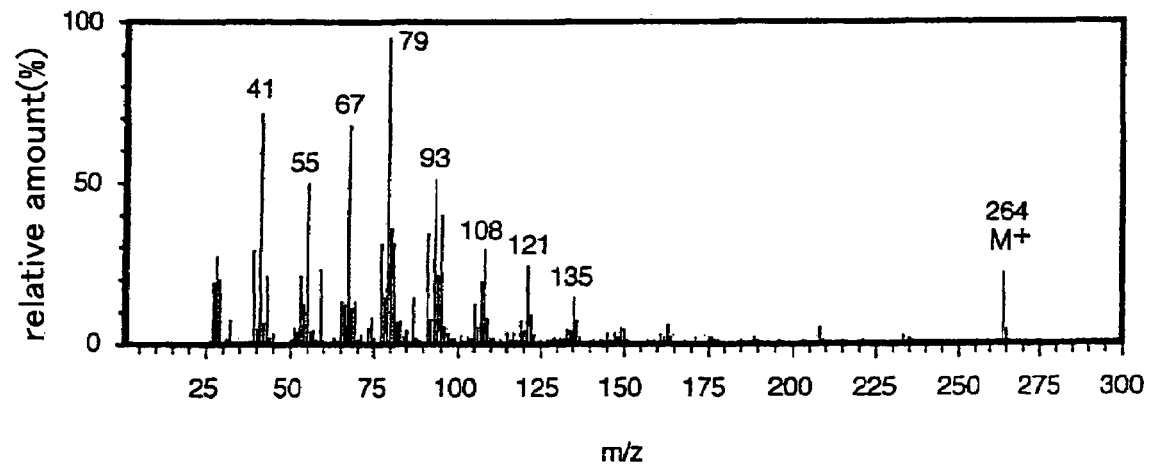

From these results, it was shown that punicic acid was produced in yeast in which PgFac was expressed, and accordingly it became clear that PgFac was a conjugase involved in synthesis of punicic acid. Moreover, several peaks were detected in the pYES2/PgFac transformed yeast cultured in a medium to which linoleic acid was not added (FIG. 7B). These peaks were not observed in the pYES transformed yeast cultured in the same manner (FIG. 7A). From their detection time and the results of GC-MS (EI) analysis performed in the same above manner, it was found that two peaks out of these detected peaks were 16:2 (9c, 12c) methyl ester and 18:2 (9c, 12c) methyl ester (FIG. 7B). From these results, it was assumed that PgFac was an enzyme having both a conjugase activity and a Δ12 desaturase activity. On the other hand, the peak indicated with the arrow heads in FIGS. 6B and 7B was subjected to GC-MS (EI) analysis in the same manner as described above. From the results that an $M^+$ ion peak appeared at m/z=264, and that the above peak was similar to the spectrums of the 16:3 (4c, 7c, 10c) and 16:3 (7c, 10c, 13c) methyl ester samples that were analyzed in the same manner, in terms of appeared peak and intensity ratio, it was concluded that the above peak was 16:3 fatty acid methyl ester (FIG. 8). From the fact that this peak was not observed in the pYES2 transformed yeast (FIGS. 6A and 7A), it was assumed that when PgFac was expressed in yeast, 16:2 (9c, 12c) was produced by the Δ12 desaturase activity of PgFac, and 16:3 (9c, 11t, 13c) (cis-9-, trans-11-, cis-13-hexadecatrienoic acid) containing a conjugated double bond was then produced from the above produced 16:2 (9c, 12c) as a substrate by the conjugase activity of PgFac. The peaks indicated with the values in FIGS. 6 and 7 show various fatty acid methyl esters, and they specifically represent 16:0 (palmitic acid), 16:1 (9c) (palmitoleic acid), 16:2 (9c, 12c) (9, 12-hexadecadienoic acid), 18:0 (stearic acid), 18:1 (9c) (oleic acid), 18:2 (9c, 12c) (linoleic acid), and 18:3 (9c, 11t, 13c) (punicic acid). The first value represents the number of carbon atoms, the second value represents the number of unsaturated bonds, the value immediately after the number of unsaturated bonds in the parenthesis represents the position of the unsaturated bond, and c and t represent cis and trans, respectively.

From the above results, it became clear that the conjugase gene obtained in (6) above is a gene encoding a protein having an ability of synthesizing fatty acid having trans-11-, cis-13-conjugated double bonds from fatty acid having a double bond at position Δ12.

(12) Construction of Plant Transformation Vector Containing *Punica granatum* Conjugase cDNA The plasmid DNA containing the *Punica granatum* conjugase full-length cDNA obtained in (7) above was cleaved with restriction enzymes XbaI and SacI. The obtained DNA fragment was purified by the same method as in (4) above. On the other hand, a binary vector pLAN421 [Plant Cell Reports, 10, 286-290 (1991)] was cleaved with restriction enzymes XbaI and SacI, so as to prepare a plasmid fragment of approximately 15 kb that did not contain a β-glucuronidase (GUS) gene of 1.8 kb by the same method as in (4) above. This fragment was ligated to the above cDNA fragment, so as to prepare a binary vector pKS-PgFac, in which the cDNA was inserted between a cauliflower mosaic virus (CaMV) 35S promoter sequence and an *Agrobacterium* nopaline synthase (Nos) gene terminator sequence. Moreover, a binary vector [Plant Molecular Biology, 26, 1115-1124 (1994)], which was ligated to the GUS gene of a Napin gene promoter sequence of a rapeseed [The Journal of Biological Chemistry, 262, 12196-12201 (1987)], was cleaved with restriction enzymes XbaI and SacI, and a plasmid fragment that did not contain the GUS gene was ligated to the above-described cDNA, so as to prepare a binary vector pKN-PgFac, in which the cDNA was inserted between a Napin promoter sequence and an *Agrobacterium* nopaline synthase gene terminator sequence. DH5α was transformed with these plasmids, so as to obtain colonies formed on an LB medium containing spectinomycin (50 μg/ml) and tetracycline (12.5 μg/ml). pKN-PgFac and pKS-PgFac plasmids DNAs were purified from the colonies, and using these, *Agrobacterium* EHA101 was transformed by the electroporation method, so as to obtain colonies that were formed on a YEB agar medium (0.5% Peptone, 0.5% Beef extract, 0.1% Yeast extract, 0.5% sucrose, 1.5% agarose) containing spectinomycin (50 μg/ml), tetracycline (2.5 μg/ml), chloramphenicol (25 μg/ml) and kanamycin (50 μg/ml). A portion was scraped off from the colonies, and the portion was added to 20 μl of a PCR reaction solution containing 1 μM each of the primers shown in SEQ ID NOS: 17 and 18, followed by performing a PCR reaction under the same conditions as in (7) above. The reaction product was subjected to electrophoresis, and as a result, a band of the expected size was observed. From these results, it was confirmed that the obtained colonies were *Agrobacterium* transformants containing pKN-PgFac or pKS-PgFac.

(13) Production of *Arabidopsis* Transformant

Transformation of *Arabidopsis* (*Arabidopsis thariana* ecotype Columbia) was carried out by the vacuum infiltration method applied onto its flower bud. This is to say, the *Agrobacterium* transformant containing pKN-PgFac or pKS-PgFac as described in (12) was grown in a YEB medium (0.5% Peptone, 0.5% Beef extract, 0.1% Yeast extract, 0.5% sucrose). Cells were collected by centrifugal separation at 4,000 g for 15 minutes, and they were then resuspended in an infiltration medium (1/2 MS-B5, 5% sucrose, 0.05% MES, 0.044 μM BAP, 0.08% Silwet L-77). *Arabidopsis* with a rachis approximately 2 to 10 cm long was infiltrated in this suspension under reduced pressure (5 to 10 cmHg) for approximately 15 minutes. Thereafter, the *Arabidopsis* was grown and fructified in an incubator as usual, and the seeds were collected. The thus obtained seeds (T1) were sterilized and then were inoculated in a medium containing kanamycin (30 μg/ml) as a selective marker, followed by selection.

(14) Analysis of Fatty Acid of *Arabidopsis* Transformant

Self-pollinated seeds (T2) attached to the selected T1 individual were pooled, and fatty acids were extracted therefrom. The obtained fatty acids were subjected to GC analysis. This is to say, approximately 2 mg of the seeds was subjected to a methylation reaction at 50° C. for 1 hour in 1 ml of a 0.5 M sodium methoxide/methanol solution. Thereafter, 1.5 ml of 0.9% NaCl and 1 ml of hexane were added to the reaction solution followed by shaking for 1 minute, and then the mixture was centrifuged at 1,000 g for 5 minutes. The obtained hexane layer was transferred into a new glass tube, followed by vacuum drying. The extract was dissolved in 20 μl of hexane, and 1 μl of the solution was then subjected to lipid analysis by GC. For this analysis, using GC-18A (Shimadzu) and a capillary column (GL Science) with TC-70, 60 m×0.25 mm and ID of 0.25 μm, the temperature was raised from 150° C. to 240° C. at a speed of 3° C./min, and then an isothermal analysis was carried out at 240° C. for 6 minutes. When fatty acid composition was compared between a non-transformed *Arabidopsis* seed (FIG. 9A) and the transformed *Arabidopsis* T2 seeds (FIG. 9B) by GC analysis, two new peaks were detected in the transformed T2 seeds (FIG. 9B, arrow and tip). The one peak (FIG. 9B, arrow) was detected at the same time when the peak (FIG. 9C, arrow) of punicic acid methyl ester contained in the *Punica granatum* seed fatty acid GC sample was detected. In order to confirm that this peak was not derived from other conjugated linoleic acids such as a-eleostearic acid or calendic acid, but was derived from punicic acid, their methyl esters were separated by gas chromatography, and these were then compared with the fatty acid methyl ester sample extracted from *Arabidopsis* (FIG. 10). That is, from each of *Trichosanthes kirilowii* seeds accumulating punicic acid, *Momordica charantia* seeds accumulating α-eleostearic acid, and *Calendula officinalis* seeds accumulating calendic acid, fatty acid methyl esters were prepared by the method described in (11) above. Subsequently, the obtained fatty acid methyl esters were mixed at an appropriate amount ratio to prepare a sample. The obtained sample was then subjected to GC analysis (FIG. 10A). For the analysis, using the same above device and column, the temperature was raised from 150° C. to 210° C. at a speed of 3° C./min, the temperature was kept at 210° C. for 13 minutes, and the temperature was then raised to 240° C. at a speed of 10° C./min. At the same time, the GC sample prepared from *Arabidopsis* seeds expressing PgFac was analyzed under the above conditions (FIG. 10B). As a result, the detection time of a new peak (FIG. 10B, arrow) detected in the transformed *Arabidopsis* seeds matched that of a punicic acid-derived peak shown in FIG. 10A. This peak (FIG. 9B, arrow) was analyzed by GC-MS (EI) described in (11) above. From the results that an M+ ion peak appeared at m/z=292, and that the above peak was similar to the spectrum of a 18:3 (9c, 12c, 15c) methyl ester sample analyzed in the same manner, in terms of appeared peak and intensity ratio, it was concluded that the above peak was 18:3 fatty acid methyl ester. From these results, it was shown that punicic acid was produced in *Arabidopsis* seeds expressing PgFac. On the other hand, the other peak (FIGS. 9B and 10B, tip) was also subjected to GC-MS (EI) analysis in the same above manner. From the results that an M+ ion peak appeared at m/z=320, and that the above peak was similar to the spectrums of the 20:3 (5c, 8c, 11c), 20:3 (7c, 10c, 13c), 20: 3 (8c, 11-11c, 14c) and 20:3 (11c, 14c, 17c) methyl ester samples analyzed in the same manner, in terms of appeared peak and intensity ratio, it was concluded that the above peak was 20:3 fatty acid methyl ester (FIG. 11). Since this new peak was not found in any of the non-transformant seeds, it was assumed that 20:3 fatty acid containing conjugated double bonds was produced in the transformant seeds by the expression of PgFac.

In order to examine whether or not the 20:3 fatty acid newly produced in *Arabidopsis* seeds expressing PgFac was produced from 20:2 (11c, 14c) (11,14-eicosadienoic acid) as a substrate existing in the seeds by the action of PgFac, an experiment was carried out using yeast expressing PgFac. That is, yeasts transformed with pYES2 and pYES2/PgFac were cultured in a medium containing 0.3 mM 20: 2 (11c, 14c) by the method described in (11) above, and the fatty acids as a whole were analyzed by GC. As shown in FIG. 12B, methyl ester peaks of 16:2 (9c, 12c), 18:2 (9c, 12c), punicic acid and 16:3 (9c, 11t, 13c) (FIG. 12B, tip) were detected in the pYES2/PgFac transformed yeast. These peaks were not observed in the pYES2 transformed yeast (FIG. 12A). However, a peak corresponding to 20:3 fatty acid methyl ester that was newly produced in a *Arabidopsis* seed expressing PgFac in FIG. 9B was not detected. From these results, it was considered that 20:2 (11c, 14c) existing in *Arabidopsis* seeds was unlikely to be a substrate of PgFac. Accordingly, it was considered that 20:3 fatty acid newly produced in *Arabidopsis* seeds expressing PgFac was highly likely to be 20:3 (11t, 15c) (cis-11, trans-13, cis-15-eicosatrienoic acid) that was produvced as a result of the elongation of the chain length of punicic acid produced by PgFac, with the activity of a chain length-elongating enzyme existing in *Arabidopsis* seeds. 6 individuals of non-transformants and 9 individuals of each of pKS-PgFac transformants and pKN-PgFac transformants were compared in terms of fatty acid composition of the seeds (Table 2). In pKS-PgFac, punicic acid was accumulated at a ratio of 0.4% on average and 0.8% at maximum. On the other hand, in pKN-PgFac, punicic acid was accumulated at a ratio of 2.3% on average and 4.4% at maximum.

Figure 9:
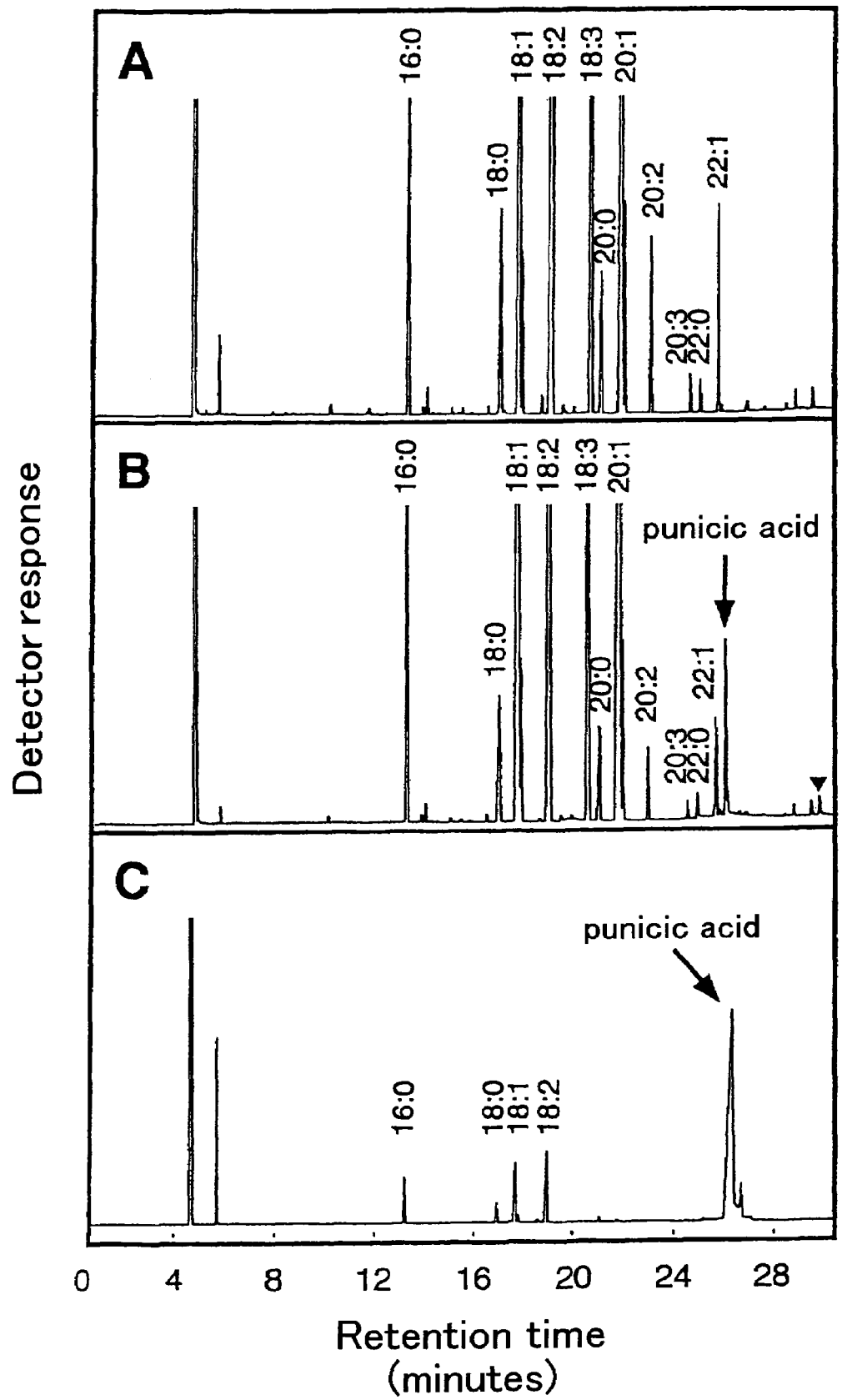
FIG. 9 shows results obtained by GC analyses of fatty acid methyl esters prepared from each of seeds (A) of non-transformed *Arabidopsis,* seeds (B) of *Arabidopsis* transformed with pKN-PgFac, and immature seeds (C) of *Punica granatum.*
Figure 10:
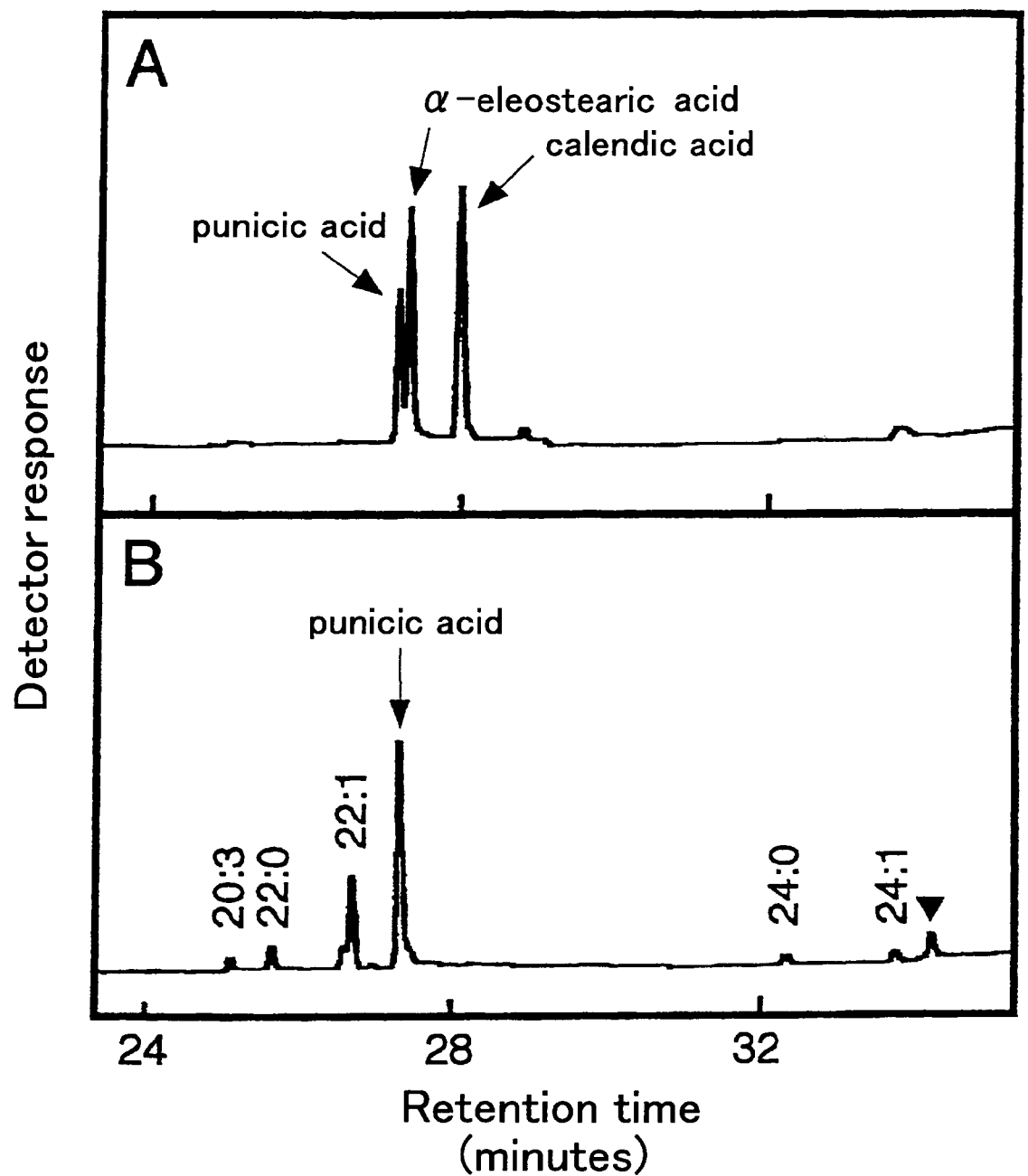
FIG. 10 shows results obtained by GC analyses of a mixture (A) of fatty acid methyl ester samples prepared from seeds of *Trichosanthes kirilowii, Momordica charantia* and *Calendula officinalis,* which contain punicic acid, α-eleostearic acid and calendic acid, respectively, and fatty acid methyl esters (B) prepared from seeds of *Arabidopsis* transformed with pKN-PgFac.
Figure 11:
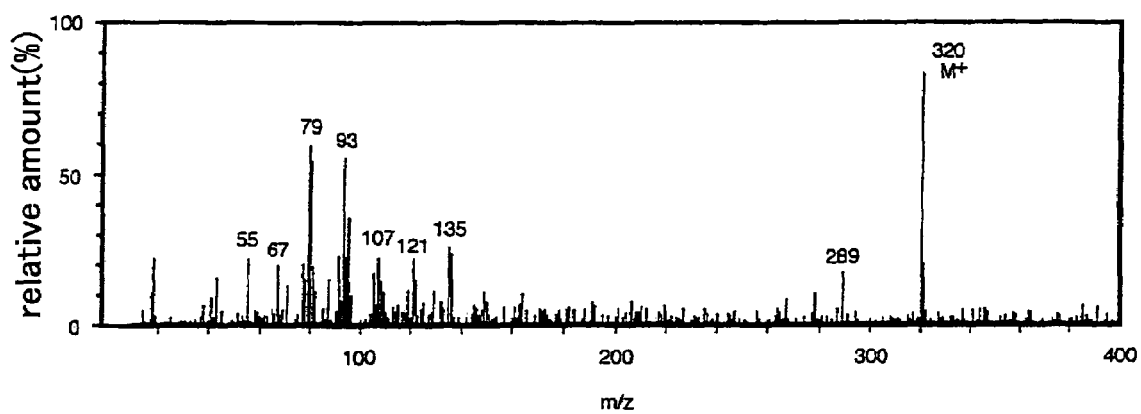
FIG. 11 shows results obtained by comparing a mass spectrum (A) obtained by GC-MS (EI) analysis of the peak indicated with a tip in FIG. 9B, with a mass spectrum (B) of 20:3 (7,10,13-eicosatrienoic acid) methyl ester analyzed in the same manner.
Figure 11:
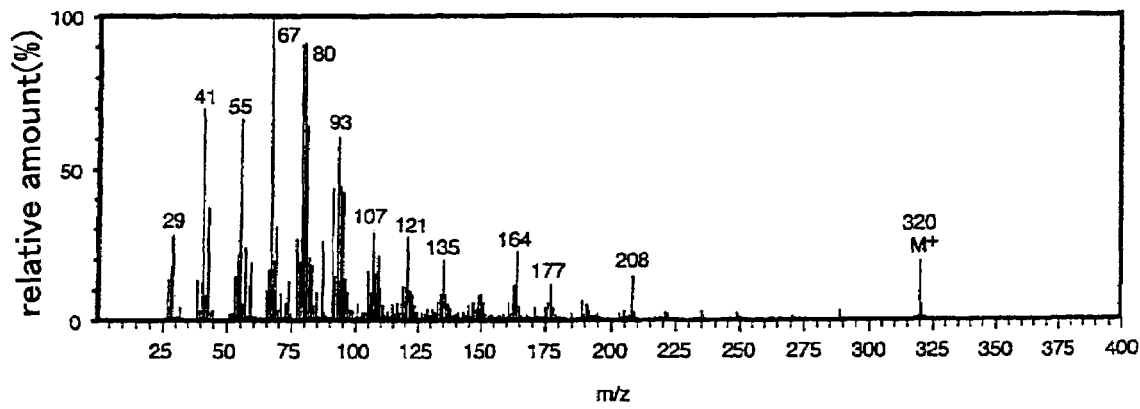
Figure 12:
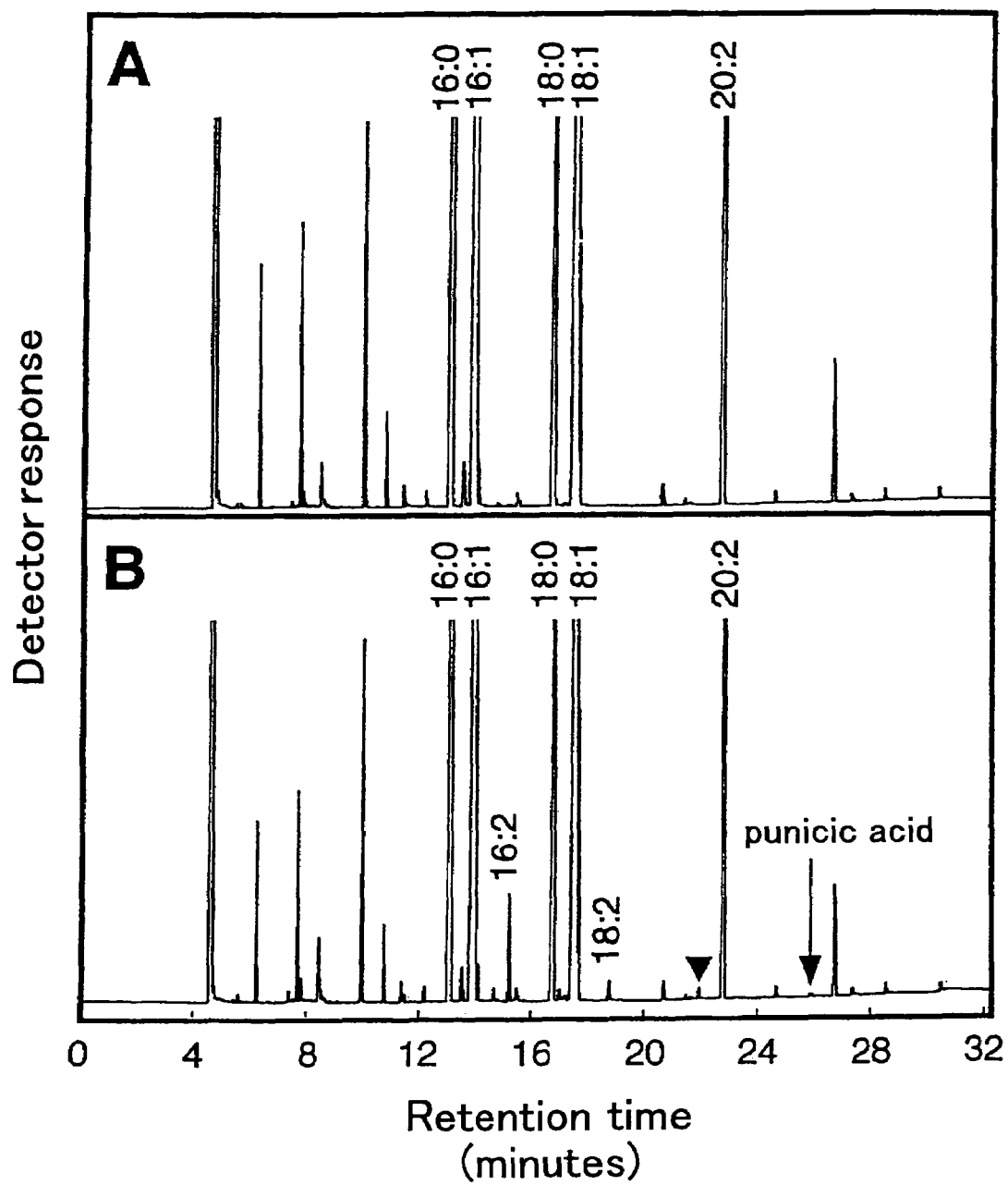
FIG. 12 shows results obtained by GC analyses of fatty acid methyl esters prepared from each of yeast cells (A) into which pYES2 was introduced, and yeast cells (B) into which pYES2/PgFac was introduced. The yeast cells were cultured in a medium to which 20:2 (11c, 14c) was added.

The peaks indicated with the values in FIGS. 9, 10 and 12 show various fatty acid methyl esters, and they specifically represent 16:0 (palmitic acid), 18:0 (stearic acid), 18:1 (9c) (oleic acid), 18:2 (9c, 12c) (linoleic acid), 18:3 (9c, 12c, 15c) (α-linolenic acid), 20:0 (arachidic acid), 20:1 (11c) (gondoic acid), 20:2 (11c, 14c) (11,14-eicosadienoic acid), 20:3 (11c, 14c, 17c) (11,14,17-eicosatrienoic acid), 22:0 (behenic acid), 22:1 (13c) (erucic acid), 24:0 (tetracosanoic acid), 24:1 (15c) (15-tetracosenoic acid) and 18:3 (9c, 11t, 13c) (punicic acid). The first value represents the number of carbon atoms, the second value represents the number of unsaturated bonds, the value immediately after the number of unsaturated bonds in the parenthesis represents the position of the unsaturated bond, and c and t represent cis and trans, respectively.

TABLE 2

Fatty acid composition of *Arabidopsis* transformant (T1) seeds expressing *Punica granatum*-derived conjugase (PgFac)

| Fatty acid weight %[1] | Non-transformant (n = 6) | PKS-PgFac (n = 9) | PKN-PgFac (n = 9) |
|---|---|---|---|
| 16:0 | 7.6 ± 0.5 | 7.3 ± 0.3 | 6.9 ± 0.3 |
| 18:0 | 2.6 ± 0.4 | 2.7 ± 0.1 | 2.9 ± 0.1 |
| 18:1 (9c) | 15.2 ± 1.5 | 19.1 ± 1.8 | 26.4 ± 4.2 |
| 18:2 (9c, 12c) | 30.3 ± 1.0 | 28.9 ± 1.2 | 24.2 ± 2.9 |
| 18:3 (9c, 12c, 15c) | 19.4 ± 1.5 | 16.1 ± 1.4 | 11.5 ± 2.4 |
| 20:0 | 1.8 ± 0.3 | 1.7 ± 0.1 | 1.5 ± 0.1 |
| 20:1 (11c) | 16.8 ± 0.9 | 17.0 ± 0.9 | 17.3 ± 1.0 |
| 20:2 (11c, 14c) | 1.8 ± 0.2 | 1.3 ± 0.2 | 0.9 ± 0.2 |
| 20:3 (11c, 14c, 17c) | 0.4 ± 0.1 | 0.3 ± 0.1 | 0.2 ± 0.1 |

TABLE 2-continued

Fatty acid composition of *Arabidopsis* transformant (T1) seeds expressing *Punica granatum*-derived conjugase (PgFac)

| Fatty acid weight %[1] | Non-transformant (n = 6) | PKS-PgFac (n = 9) | PKN-PgFac (n = 9) |
|---|---|---|---|
| 22:1 (13c) | 1.7 ± 0.3 | 1.4 ± 0.1 | 1.2 ± 0.2 |
| Punicic (9c, 11t, 13c) | N.D.[2] | 0.4 ± 0.3 | 2.3 ± 1.1 |
| 20:3[3] | N.D. | 0.1 ± 0.1 | 0.2 ± 0.1 |
| Others[4] | <3.0 | <4.0 | <5.0 |

[1]Fatty acid composition is expressed by % with respect to the total weight of lipids.
[2]N.D. = not detected
[3]20:3 isomer predicted to contain conjugated double bonds
[4]Others mainly include 18:1 and 20:1 isomers, and also include 22:0, etc.

INDUSTRIAL APPLICABILITY

By the present invention, a new gene involved in synthesis of fatty acid having trans-11-, cis-13-conjugated double bonds, such as punicic acid, was cloned. Using the gene of the present invention, it becomes possible to produce and accumulate in a plant body, fatty acid having trans-11-, cis-13-conjugated double bonds, such as punicic acid, thereby enabling the industrial application of this conjugated fatty acid.

All the contents disclosed in Japanese Patent Application Nos. 2001-286390, 2002-127810, 2002-226386, and 2002-226387, which the present application claims priorities based on, are incorporated in the present specification as a part of the disclosure of this specification.

---

The invention claimed is:

1. An isolated or purified gene selected from the group consisting of:
   (A) a nucleotide sequence encoding the amino acid sequence shown in SEQ ID NO: 1 or 12;
   (B) a nucleotide sequence encoding an amino acid sequence comprising a deletion, addition or substitution of one to twenty amino acids in the amino acid sequence shown in SEQ NO: 1 or 12, wherein said amino acid sequence has the ability to catalyze the synthesis of fatty acids having trans-11-, cis-13-conjugated double bonds from a fatty acid having a double bond at position 12;
   (C) the nucleotide sequence shown in SEQ ID NO: 2 or 13; and
   (D) a nucleotide sequence comprising a deletion, addition or substitution of one to sixty nucleotides in the nucleotide sequence shown in SEQ ID NO: 2 or 13, wherein said nucleotide sequence encodes a protein having the ability to catalyze the synthesis of fatty acids having trans-11-, cis-13-conjugated double bonds from a fatty acid having a double bond at position 12.

2. An isolated or purified protein selected from the group consisting of:
(A) the amino acid sequence shown in SEQ ID NO: 1 or 12;
(B) an amino acid sequence comprising a deletion, addition or substitution of one to twenty amino acids in the amino acid sequence shown in SEQ ID NO: 1 or 12, wherein said amino acid sequence has the ability to catalyze the synthesis of fatty acids having trans-11-, cis-13-conjugated double bonds from a fatty acid having a double bond at position 12.

3. The isolated or purified gene according to claim 1 wherein the ability to catalyze the synthesis of fatty acids having trans-11-, cis-13-conjugated double bonds from a fatty acid having a double bond at position 12 is the ability to catalyze the synthesis of punicic acid from linoleic acid.

4. The isolated or purified protein according to claim 2 wherein the ability to catalyze the synthesis of fatty acids having trans-11-, cis-13-conjugated double bonds from a fatty acid having a double bond at position 12 is the ability to catalyze the synthesis of punicic acid from linoleic acid.

5. A vector comprising a gene according to claim 1.

6. A vector comprising the gene according to claim 1 wherein the ability to catalyze the synthesis of fatty acid having trans-11-, cis-13-conjugated double bonds from fatty acid having a double bond at position 12 is the ability to catalyze the synthesis of punicic acid from linoleic acid.

7. A host cell comprising a bacteria, yeast, or plant that naturally produces fatty acids having a double bond at position 12 wherein said host cell is transformed with the vector according to claim 5 or the gene according to claim 1 wherein the ability to catalyze the synthesis of fatty acids having trans-11-, cis-13-conjugated double bonds from fatty acids having a double bond at position 12 is the ability to catalyze the synthesis of punicic acid from linoleic acid.

8. The transformed host cell according to claim 7 which is a transformed plant cell.

9. A method for producing fatty acid having trans-11-, cis-13-conjugated double bonds from a fatty acid having a double bond at position 12, wherein said method comprises contacting the protein according to claim 2 with a fatty acid having a double bond at position 12.

10. A method for producing fatty acid having trans-11-, cis-13-conjugated double bonds, wherein the method comprises culturing the transformed host cell according to claim 7, and collecting the fatty acids having trans-11-, cis-13-conjugated double bonds.

11. A method of claim 10 further comprising selecting the transformed host cell producing an increased amount of fatty acid having trans-11-, cis-13- conjugated double bonds as compared with the untransformed host cell is selected.

12. A primer set consisting of a combination of a primer having the nucleotide sequence shown in SEQ ID NO: 3 or 4 and a primer having the nucleotide sequence shown in SEQ ID NO: 5.

13. A primer set consisting of a combination of primers having the nucleotide sequences shown in SEQ ID NOS: 6 and 7.

14. A primer set consisting of a combination of a primer having the nucleotide sequence shown in SEQ ID NO: 14 or 15 and a primer having the nucleotide sequence shown in SEQ ID NO: 16.

15. A primer set consisting of a combination of a primer having the nucleotide sequence shown in SEQ ID NO: 17 or 19 and a primer having the nucleotide sequence shown in SEQ ID NO: 18 or 20.

16. A seed obtained from the transformed plant cell according to claim 8.

17. A method for increasing the content of fatty acids having trans-11-, cis-13-conjugated double bonds in a host cell of comprising the steps of: (a) transforming a host cell of bacteria, yeast, or a polynucleotide encoding the protein according to claim 2 wherein the ability to catalyze the synthesis of fatty acid having trans-11-, cis-13-conjugated double bonds from fatty acid having a double bond at position 12 is an ability to catalyze the synthesis of punicic acid from linoleic acid; (b) allowing the host cell to grow under appropriate conditions to allow said gene to be expressed; and (c) selecting host cells comprising an increased amount of fatty acid having trans-11-, cis-13-conjugated double bonds, wherein the transformed host cell naturally produces a fatty acid having a double bond at position 12.

18. A method for producing a seed oil, which comprises the steps of: (a) transforming a plant cell with a gene encoding the protein according to claim 2 wherein the ability to catalyze the synthesis of fatty acids having trans-11-, cis-13-conjugated double bonds from fatty acid having a double bond at position 12 is an ability to catalyze the synthesis of punicic acid from linoleic acid; (b) growing a plant from the obtained transformed plant cell; (c) obtaining progeny seeds from the obtained plant; and (d) obtaining oil comprising fatty acids having trans-11-, cis-13-conjugated double bonds from the obtained progeny seeds.

19. The method of claim 18 further comprising selecting the transformed plant producing an increased amount of fatty acid having trans-11-, cis-13-conjugated double bonds as compared with the untransformed host plant.

20. The seed according to claim 16, wherein the amount of fatty acid having trans-11-, cis-13-conjugated double bonds is increased relative to a non-transformed seed by transformation.

* * * * *

UNITED STATES PATENT AND TRADEMARK OFFICE
CERTIFICATE OF CORRECTION

PATENT NO. : 7,402,418 B2
APPLICATION NO. : 10/490299
DATED : July 22, 2008
INVENTOR(S) : M. Osumi et al.

It is certified that error appears in the above-identified patent and that said Letters Patent is hereby corrected as shown below:

At Column 61, Line 20 (Claim 4, Line 2), "acids" should be --acid--.

At Column 61, Line 21 (Claim 4, Line 3), delete "a".

At Column 61, Line 45 (Claim 10, Line 1), "acid" should be --acids--.

At Column 62, Line 21 (Claim 17, Line 1), delete "of" before the word comprising.

Signed and Sealed this

Third Day of March, 2009

JOHN DOLL
*Acting Director of the United States Patent and Trademark Office*